US011389803B2

United States Patent
Cai et al.

(10) Patent No.: US 11,389,803 B2
(45) Date of Patent: Jul. 19, 2022

(54) LIQUID SENDING METHOD AND LIQUID SENDING APPARATUS

(71) Applicant: SYSMEX CORPORATION, Kobe (JP)

(72) Inventors: Kunpeng Cai, Kobe (JP); Koya Yamawaki, Kobe (JP); Yasuko Kawamoto, Kobe (JP); Katsumi Nakanishi, Kobe (JP); Ayato Tagawa, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 458 days.

(21) Appl. No.: 15/905,034

(22) Filed: Feb. 26, 2018

(65) Prior Publication Data

US 2018/0243744 A1 Aug. 30, 2018

(30) Foreign Application Priority Data

Feb. 27, 2017 (JP) .............................. JP2017-035564

(51) Int. Cl.
*B01L 3/00* (2006.01)
*B01L 3/02* (2006.01)
(Continued)

(52) U.S. Cl.
CPC ............... *B01L 3/56* (2013.01); *B01L 3/0293* (2013.01); *C12Q 1/6806* (2013.01);
(Continued)

(58) Field of Classification Search
CPC .. B01L 3/56; B01L 3/0293; B01L 2200/0673; B01L 2400/0487;
(Continued)

(56) References Cited

U.S. PATENT DOCUMENTS 5,294,023 A * 3/1994 Ioannides ............. B01L 3/0293
222/61
6,086,740 A 7/2000 Kennedy
(Continued)

FOREIGN PATENT DOCUMENTS

| CN | 1975434 A | 6/2007 |
| CN | 101151535 A | 3/2008 |

(Continued)

OTHER PUBLICATIONS

Extended European search report dated Jun. 27, 2018 in a counterpart European patent application No. 18157866.7.
(Continued)

*Primary Examiner* — Lore R Jarrett
(74) *Attorney, Agent, or Firm* — Crowell & Moring LLP

(57) ABSTRACT

Disclosed is a liquid sending method for sending liquid to a sample processing chip having a flow path formed therein, the method including: measuring a flow of a second liquid which is different from a first liquid which is introduced into the flow path in the sample processing chip; controlling the flow of the second liquid on the basis of the measured flow; and introducing the first liquid into the flow path in the sample processing chip by means of the second liquid of which flow is controlled.

13 Claims, 29 Drawing Sheets

(51) Int. Cl.
*C12Q 1/6806* (2018.01)
*G01N 33/53* (2006.01)

(52) U.S. Cl.
CPC .... *G01N 33/5302* (2013.01); *B01L 3/502784* (2013.01); *B01L 2200/0605* (2013.01); *B01L 2200/0647* (2013.01); *B01L 2200/0673* (2013.01); *B01L 2300/0663* (2013.01); *B01L 2400/0487* (2013.01); *B01L 2400/082* (2013.01)

(58) Field of Classification Search
CPC ....... B01L 2200/0647; B01L 3/502784; B01L 2300/0663; B01L 2400/082; B01L 2200/0605; C12Q 1/6806; G01N 33/5302; G01N 35/10
See application file for complete search history.

(56) References Cited

U.S. PATENT DOCUMENTS

| | | | |
|---|---|---|---|
| 7,307,104 B2 * | 12/2007 | Qiu | A61P 33/00 516/54 |
| 8,528,589 B2 | 9/2013 | Miller et al. | |
| 2003/0012697 A1 | 1/2003 | Hahn et al. | |
| 2006/0228812 A1 | 10/2006 | Higashino et al. | |
| 2006/0263914 A1 * | 11/2006 | Sando | B01L 3/50273 438/14 |
| 2007/0054119 A1 * | 3/2007 | Garstecki | B22F 1/0007 428/402 |
| 2007/0116601 A1 | 5/2007 | Patton | |
| 2008/0003142 A1 | 1/2008 | Link et al. | |
| 2008/0118369 A1 * | 5/2008 | Sando | G05D 7/0694 417/36 |
| 2011/0000560 A1 | 1/2011 | Miller et al. | |
| 2011/0059556 A1 | 3/2011 | Strey et al. | |
| 2014/0220350 A1 * | 8/2014 | Kim | B01F 3/0811 428/402.21 |
| 2016/0271576 A1 * | 9/2016 | Arab | B01F 3/0807 |

FOREIGN PATENT DOCUMENTS

| | | |
|---|---|---|
| CN | 101187669 A | 5/2008 |
| EP | 0477811 A2 | 4/1992 |
| EP | 1568715 A1 | 8/2005 |
| JP | H4-253693 A | 9/1992 |
| JP | 2004-61320 A | 2/2004 |
| JP | 2008-128869 A | 6/2008 |
| JP | 2010-506136 A | 2/2010 |
| JP | 2014-522718 A | 9/2014 |
| WO | 2006/123578 A1 | 11/2006 |
| WO | 2008/063227 A2 | 5/2008 |
| WO | WO 2009/069449 A1 | 6/2009 |
| WO | 2010/009365 A1 | 1/2010 |
| WO | 2013/006661 A2 | 1/2013 |

OTHER PUBLICATIONS

Communication pursuant to Article 94(3) EPC dated Jan. 29, 2020 in a counterpart European patent application No. 18157866.7.
Autebert, J. et al., "Convection-Enhanced Biopatterning with Recirculation of Hydrodynamically Confined Nanoliter Volumes of Reagents", *Analytical Chemistry*, vol. 88, 2016, pp. 3235-3242.
Herricks, T. et al., "A Microfluidic System to Study Ctyoadhesion of Plasmodium Falciparum Infected Erythrocytes to Primary Brain Microvascularendothelial Cells", *Lab Chip*, vol. 11, No. 7, Sep. 7, 2011, 14 pages.
Yun, H. et al., "Sequential Multi-Molecule Delivery Using Vortex-Assisted Electroporation", *Lab on a Chip*, 2013, pp. 2764-2772.
Yun, H. et al., "Sequential Multi-Molecule Delivery Using Vortex-Assisted Electroporation", *Electronic Supplementary Information-Lab on a Chip (The Royal Society of Chemistry)*, 2013, 9 pages.
Communication pursuant to Article 94(3) EPC dated Oct. 7, 2020 in a counterpart European patent application No. 18157866.7.
Decision of Refusal dated Mar. 30, 2021 in a counterpart Japanese patent application No. 2017-035564.
Japanese Office Action dated Jan. 12, 2021 in a counterpart Japanese patent application No. 2017-035564.
Chinese Office Action dated Oct. 29, 2021 in a counterpart Chinese patent application No. 201810156373.6.
Japanese Office Action dated Dec. 14, 2021 in a counterpart Japanese patent application No. 2017-035564.
Office Action No. 2 in China Application No. 201810156373.6, dated May 9, 2022, including English translation, 13 pages.

* cited by examiner

FIG. 48

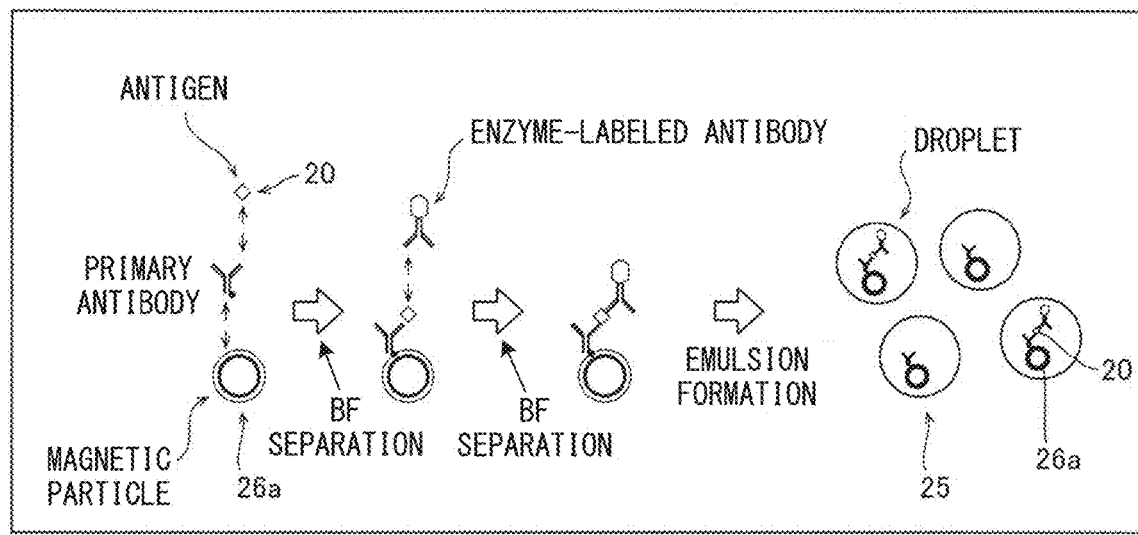

FIG. 49

| STEP<br>LIQUID | Pre-PCR | EMULSION FORMATION<br>EMULSION PCR | EMULSION BREAKING<br>HYBRIDIZATION |
|---|---|---|---|
| FIRST<br>LIQUID | MIXTURE THAT CONTAINS<br>DNA SAMPLE AND<br>PCR AMPLIFICATION<br>REAGENT<br>(2 μL/minute) | MIXTURE THAT CONTAINS<br>DNA AMPLIFIED THROUGH<br>Pre-PCR, MAGNETIC<br>PARTICLE, AND<br>PCR AMPLIFICATION<br>REAGENT<br>(2 μL/minute) | MIXTURE OF DROPLETS<br>CONTAINING DNA SAMPLE<br>AMPLIFIED THROUGH<br>EMULSION PCR<br>(2 μL/minute)<br>REAGENT THAT CONTAINS<br>LABELED PROBE<br>(20 μL/minute) |
| SECOND<br>LIQUID | MIXTURE THAT CONTAINS<br>MINERAL OIL | MIXTURE THAT CONTAINS<br>MINERAL OIL | MIXTURE THAT CONTAINS<br>MINERAL OIL |

FIG. 50

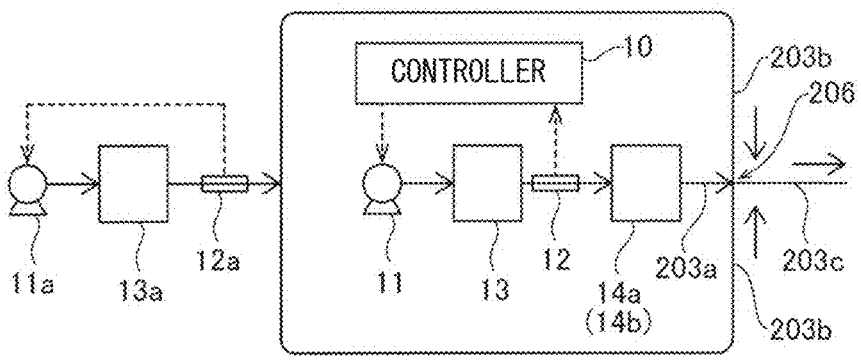

FIG. 51

EXAMPLE 1  SUPPLY OF FIRST LIQUID FROM SAMPLE CONTAINER

|  | FIRST LIQUID | SECOND LIQUID | CONTINUOUS PHASE |
|---|---|---|---|
| COMPONENT | MIXTURE THAT CONTAINS DNA AMPLIFIED THROUGH Pre-PCR, MAGNETIC PARTICLE, AND PCR AMPLIFICATION REAGENT | MIXTURE THAT CONTAINS MINERAL OIL | MIXTURE THAT CONTAINS MINERAL OIL |
| FLOW RATE | 3.25 $\mu$L/minute | 3.25 $\mu$L/minute | 6.5 $\mu$L/minute |

CROSS-SECTIONAL AREA OF CROSSING PART: 400 $\mu m^2$ (20 $\mu$m × 20 $\mu$m)

FIG. 52

EXAMPLE 2  SUPPLY OF FIRST LIQUID FROM RESERVOIR ON SAMPLE PROCESSING CHIP

|  | FIRST LIQUID | SECOND LIQUID | CONTINUOUS PHASE |
|---|---|---|---|
| COMPONENT | MIXTURE THAT CONTAINS DNA AMPLIFIED THROUGH Pre-PCR, MAGNETIC PARTICLE, AND PCR AMPLIFICATION REAGENT | MIXTURE THAT CONTAINS MINERAL OIL | MIXTURE THAT CONTAINS MINERAL OIL |
| FLOW RATE | 3.6 $\mu$L/minute | 3.6 $\mu$L/minute | 3.9 $\mu$L/minute |

CROSS-SECTIONAL AREA OF CROSSING PART: 400 $\mu m^2$ (20 $\mu$m × 20 $\mu$m)

FIG. 55

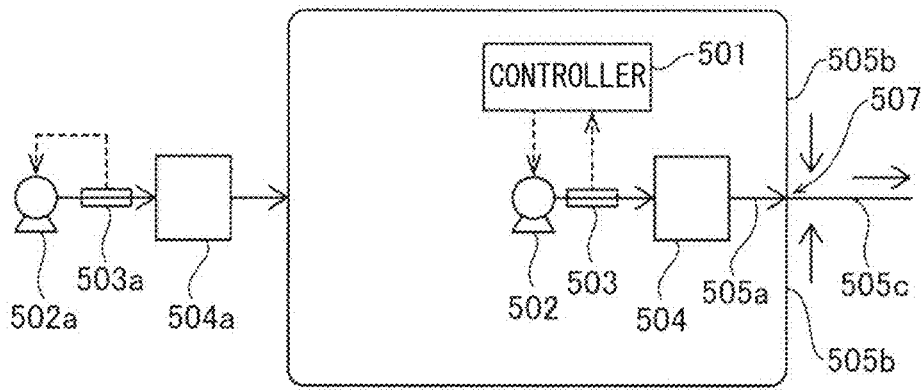

FIG. 56

COMPARATIVE EXAMPLE 1   SUPPLY OF FIRST LIQUID FROM SAMPLE CONTAINER

|  | FIRST LIQUID | CONTINUOUS PHASE |
|---|---|---|
| COMPONENT | MIXTURE THAT CONTAINS DNA AMPLIFIED THROUGH Pre-PCR, MAGNETIC PARTICLE, AND PCR AMPLIFICATION REAGENT | MIXTURE THAT CONTAINS MINERAL OIL |
| PRESSURE | 1500mbar | 1500mbar |

CROSS-SECTIONAL AREA OF CROSSING PART: 400 $\mu m^2$ (20 $\mu m$ × 20 $\mu m$)

FIG. 57

COMPARATIVE EXAMPLE 2   SUPPLY OF FIRST LIQUID FROM SAMPLE CONTAINER

|  | FIRST LIQUID | CONTINUOUS PHASE |
|---|---|---|
| COMPONENT | MIXTURE THAT CONTAINS DNA AMPLIFIED THROUGH Pre-PCR, MAGNETIC PARTICLE, AND PCR AMPLIFICATION REAGENT | MIXTURE THAT CONTAINS MINERAL OIL |
| PRESSURE | 1000mbar | 1500mbar |

CROSS-SECTIONAL AREA OF CROSSING PART: 400 $\mu m^2$ (20 $\mu m$ × 20 $\mu m$)

COMPARATIVE EXAMPLE 1

COMPARATIVE EXAMPLE 2

LIQUID SENDING METHOD AND LIQUID SENDING APPARATUS

CROSS REFERENCE TO RELATED APPLICATIONS

This application claims priority from prior Japanese Patent Application No. 2017-035564, filed on Feb. 27, 2017, entitled "liquid sending method and liquid sending apparatus", the entire content of which is incorporated herein by reference.

FIELD OF THE INVENTION

The present invention relates to a liquid sending method and a liquid sending apparatus for sending liquid to a sample processing chip having a flow path formed therein.

BACKGROUND

In order to perform accurate processing by use of a sample processing chip having a micro flow path formed therein, it is necessary to accurately control the flow rate of liquid flowing in the flow path. Conventionally, a method is known in which: a flow rate sensor is set at a flow path; and a sample solution to be introduced into the flow path is sent (for example, see AUTEBERT, Julien, et al., Convection-Enhanced Biopatterning with Recirculation of Hydrodynamically Confined Nanoliter Volumes of Reagents. Analytical chemistry, 2016, 88.6: 3235-3242. Hereinafter, this literature will be referred to as Non-Patent Literature 1). As shown in FIG. 60, in the liquid sending method according to Non-Patent Literature 1, the flow rate of a sample solution is measured by a sensor 506, and the measured flow rate of the sample solution is feedback-controlled by a controller 501, whereby the flow rate of the sample solution to a flow path 505 is controlled.

In such a liquid sending method as in Non-Patent Literature 1, when a plurality of samples are to be processed, it is necessary to take, every time a sample is changed, a countermeasure such as: sufficiently washing the sample introduction system including the flow rate sensor; or replacing the sample introduction system including the flow rate sensor with an unused sample introduction system, (i.e., using a disposable sample introduction system). If the washing is insufficient, a problem of occurrence of contamination could be caused.

Thus, a method is known in which an air pressure is caused to act on liquid that is introduced into a flow path, thereby sending the liquid (for example, see YUN, Hoyoung, et al., Sequential Multi-Molecule Delivery Using Vortex-Assisted Electroporation. Lab on a Chip 2013.13.14: 2764-2772. Hereinafter, this literature will be referred to as Non-Patent Literature 2). In the liquid sending method according to Non-Patent Literature 2, as shown in FIG. 61, the air pressure outputted by a pump 502 is measured by a sensor 503, and the measured air pressure is feedback-controlled by the controller 501, whereby the flow rate of the liquid to be introduced into the flow path 505 is controlled.

In the liquid sending method according to Non-Patent Literature 2, without taking a countermeasure such as: sufficiently washing the sample introduction system including the flow rate sensor; or replacing the sample introduction system including the flow rate sensor with an unused sample introduction system (i.e., using a disposable sample introduction system) every time a sample is changed, occurrence of contamination can be prevented. However, since the fluid of which flow rate is to be measured is gas, the volume thereof changes due to a slight change in pressure. Thus, there is a problem that it is difficult to accurately control the flow of the liquid that is introduced into the flow path.

The present invention is directed to providing a liquid sending method and a liquid sending apparatus in which, when processing of a liquid is performed by use of a sample processing chip having a flow path formed therein, the flow of a liquid, such as a sample specimen or a reagent, that is introduced into a flow path in a chip is accurately controlled while occurrence of sample contamination when a plurality of samples are processed is prevented.

SUMMARY OF THE INVENTION

The scope of the present invention is defined solely by the appended claims, and is not affected to any degree by the statements within this summary.

A liquid sending method according to a first aspect of the present invention is a method for sending liquid to a sample processing chip (200) having a flow path (201) formed therein, the method including: measuring a flow of a second liquid (22) which is different from a first liquid (21) which is introduced into the flow path (201) in the sample processing chip (200); controlling the flow of the second liquid (22) on the basis of the measured flow; and introducing the first liquid (21) into the flow path (201) in the sample processing chip (200) by means of the second liquid (22) of which flow is controlled.

In the liquid sending method according to the first aspect, as described above, the flow of the second liquid (22) is controlled on the basis of the measured flow of the second liquid (22), and the first liquid (21) is introduced into the flow path (201) in the sample processing chip (200) by means of the second liquid (22) of which flow is controlled. Thus, since the first liquid (21) is sent by means of the second liquid (22), the second liquid (22) can be inhibited from being compressed, different from a case where the first liquid (21) is sent by causing the pressure of gas to act thereon. Accordingly, the flow of the first liquid (21) can be accurately controlled. In addition, since feedback-control can be performed by measuring the flow of the second liquid (22), there is no need to provide a sensor in the flow path for the first liquid (21). Thus, also when a plurality of the first liquids (21) are each processed by use of the sample processing chip (200), there is no need to wash or replace the flow path provided with a sensor, for each processing. As a result, the problem of sample contamination when a plurality of samples are processed can be effectively solved. Thus, when processing of a liquid is performed by use of the sample processing chip (200) having the flow path (201) formed therein, the flow of the liquid, such as a sample specimen or a reagent, that is introduced into the flow path (201) in the chip can be accurately controlled while occurrence of sample contamination when a plurality of samples are processed is prevented. This effect is especially advantageous when the first liquid (21) is supplied to and processed in a micro flow path where fine flow control is performed.

In the liquid sending method according to the first aspect described above, preferably, a flow of the first liquid (21) which is introduced into the flow path (201) in the sample processing chip (200) is controlled by the controlling of the flow of the second liquid (22). With this configuration, since the flow of the first liquid (21) can be controlled through the control of the flow of the second liquid (22), which is liquid being less likely to be compressed when compared with gas, it is possible to accurately control the flow of the first liquid (21) without providing a sensor for measuring the flow to the flow path (201) for the first liquid (21).

In the liquid sending method according to the first aspect described above, preferably, the measuring of the flow is measuring at least one of flow rate, flow velocity, and pressure. The flow rate is the volume or the mass of a liquid that passes per unit time. The flow velocity is a representative linear velocity of the liquid. The representative linear velocity is the mean velocity, the maximum velocity, or the like, for example. The pressure is the pressure of the liquid. With this configuration, by controlling the flow including at least one of the flow rate, the flow velocity, and the pressure of the second liquid (22), it is possible to accurately control the flow including at least one of the flow rate, the flow velocity, and the pressure of the first liquid (21).

In the liquid sending method according to the first aspect described above, preferably, the second liquid (22) is a liquid having immiscibility with the first liquid (21). In a case where the second liquid (22) has immiscibility with the first liquid (21), when the second liquid (22) comes into contact with the first liquid (21), a boundary is generated therebetween, and two phases are formed. For example, the second liquid (22) has solubility of less than 1 percent by volume with respect to the first liquid (21). That is, immiscibility encompasses not only a property of a substance allowing no portion thereof to be mixed with another substance at all but also a property of a substance allowing substantially no portion thereof to be mixed with another substance. That is, the second liquid (22) may be slightly mixed with the first liquid (21). With this configuration, even when the second liquid (22) is brought into contact with the first liquid (21), it is possible to suppress mixing of the second liquid (22) into the first liquid (21) to cause dilution of the first liquid (21), and mixing of impurities into the first liquid (21).

In this case, preferably, the first liquid (21) is a liquid serving as one of an aqueous phase and an oil phase, and the second liquid (22) is a liquid serving as another of the aqueous phase and the oil phase. With this configuration, if one of the first liquid (21) and the second liquid (22) is set as an oil phase, and the other of the first liquid (21) and the second liquid (22) is set as an aqueous phase, the first liquid (21) and the second liquid (22) can be easily prevented from being mixed with each other.

In a case where the second liquid (22) is a liquid that is hardly mixed with the first liquid (21), preferably, the second liquid (22) is a liquid having a specific gravity different from that of the first liquid (21). With this configuration, even when the second liquid (22) is introduced into a container containing the first liquid (21), the first liquid (21) and the second liquid (22) can be separated from each other in the up-down direction, due to the difference in specific gravity.

In the liquid sending method according to the first aspect described above, preferably, when a plurality of samples are each processed by use of the sample processing chip (200), the second liquid (22) is a liquid to be used in common among processes performed on the respective samples. With this configuration, the flow path that is provided with the sensor (12) for measuring the flow of the second liquid (22) need not be washed or replaced, for each sample. Thus, the number of the sensors (12) to be provided can be minimized, and work can be simplified.

In the liquid sending method according to the first aspect described above, preferably, when a plurality of samples are each processed by use of the sample processing chip (200), the first liquid (21) is a liquid that has a different liquid composition or a different source of a target component for each of the plurality of samples. With this configuration, if different flow paths (201) for the first liquids (21) respectively having different components are provided for the respective samples, the different samples can be inhibited from being mixed with one another.

In the liquid sending method according to the first aspect described above, preferably, the first liquid (21) is a solution that contains at least one of a sample, a reagent, and particles. With this configuration, while the flow of the solution containing at least one of the sample, the reagent, and the particles is accurately controlled, the solution can be sent.

In this case, preferably, the first liquid (21) is a solution that contains a nucleic acid derived from blood, magnetic particles, and a reagent for polymerase chain reaction. With this configuration, while the flow of the solution containing the nucleic acid derived from blood, the magnetic particles, and the reagent for polymerase chain reaction is accurately controlled, the solution can be sent.

In the liquid sending method according to the first aspect described above, preferably, the second liquid (22) is a liquid that contains an oil being in a liquid state at room temperature. The room temperature is a temperature about 20° C., and includes a temperature in a range of not lower than 0° C. and not higher than 40° C. With this configuration, when the first liquid (21) is processed at room temperature, the first liquid (21) can be easily sent by means of the second liquid (22) in a liquid state.

In the liquid sending method according to the first aspect described above, preferably, the first liquid (21) is introduced into the flow path (201) in the sample processing chip (200) at a flow rate of not less than 0.1 μL/minute and not greater than 5 mL/minute. With this configuration, the flow rate of the first liquid (21) of not less than 0.1 μL/minute and not greater than 5 mL/minute can be accurately controlled.

In this case, preferably, the first liquid (21) is introduced into the flow path (201) in the sample processing chip (200) at a flow rate of not less than 0.1 μL/minute and not greater than 1 mL/minute. With this configuration, by the first liquid (21) being sent at a flow rate of not greater than 1 mL/minute, a high throughput in IVD can be realized.

In the liquid sending method according to the first aspect described above, preferably, in addition to the introducing of the first liquid (21), a dispersion medium (23) for emulsion formation is introduced into the flow path (201) in the sample processing chip (200) to perform emulsion formation, and in the emulsion formation, dispersoids are formed from the first liquid (21) at a rate of not less than 600 droplets/minute and not greater than 600 million droplets/minute. An emulsion is a milky liquid in which minute particles, as dispersoids, of a liquid are dispersed in another liquid that is immiscible therewith. The emulsion includes a dispersion medium and dispersoids. The dispersion medium surrounds the dispersoids to form a continuous phase. The dispersoids are dispersed in the form of droplets, in the dispersion medium. With this configuration, an emulsion including the first liquid (21) as dispersoids can be formed while the flow of the first liquid (21) is accurately controlled, and thus, variation in the particle diameter of the dispersoids can be suppressed. In addition, emulsion droplets having a substantially uniform particle diameter can be efficiently formed at a rate of not less than 600 droplets/minute and not greater than 600 million droplets/minute.

In this case, preferably, in the emulsion formation, dispersoids are formed from the first liquid (21) at a rate of not less than 3000 droplets/minute and not greater than 18 million droplets/minute. With this configuration, emulsion droplets having a substantially uniform particle diameter can be efficiently formed at a rate of not less than 3000 droplets/minute and not greater than 18 million droplets/minute.

In the liquid sending method according to the first aspect described above, preferably, in addition to the introducing of the first liquid (21), a dispersion medium (23) for emulsion formation is introduced into the flow path (201) in the sample processing chip (200) to perform emulsion formation, and in the emulsion formation, dispersoids having a mean particle diameter of not less than 0.1 μm and not greater than 500 μm are formed from the first liquid (21). With this configuration, an emulsion including the first liquid (21) as dispersoids can be formed while the flow of the first liquid (21) is accurately controlled, and thus, variation in the particle diameter of the dispersoids can be suppressed. In addition, emulsion droplets having a substantially uniform particle diameter and having a mean particle diameter of not less than 0.1 μm and not greater than 500 μm can be efficiently formed.

In this case, preferably, in the emulsion formation, dispersoids having a mean particle diameter of not less than 0.1 μm and not greater than 200 μm are formed from the first liquid (21). With this configuration, an emulsion including dispersoids having a mean particle diameter of not greater than 200 μm which is suitable for bio-measurement can be efficiently formed.

In the liquid sending method according to the first aspect described above, preferably, the flow path (201) formed in the sample processing chip (200) has a cross-sectional area of not less than 0.01 μm$^2$ and not greater than 10 mm$^2$. The cross-sectional area of the flow path (201) is the cross-sectional area thereof in a cross section orthogonal to the flowing direction of the liquid in the flow path (201). With this configuration, even in a case where the flow is small and difficult to be maintained to be constant, the liquid can be sent with the flow finely controlled. Thus, even when the first liquid (21) in a small flow is sent into the flow path (201) having a small cross-sectional area of not less than 0.01 μm$^2$ and not greater than 10 mm$^2$, the liquid can be sent with the flow accurately controlled.

In this case, preferably, the flow path (201) formed in the sample processing chip (200) has a cross-sectional area of not less than 0.01 μm$^2$ and not greater than 1 mm$^2$. With this configuration, even when the first liquid (21) in a smaller flow is sent into the flow path (201) having a cross-sectional area of not greater than 1 mm$^2$, the liquid can be sent with the flow accurately controlled.

In the above-described configuration in which the flow path (201) formed in the sample processing chip (200) has a cross-sectional area of not less than 0.01 μm$^2$ and not greater than 1 mm$^2$, preferably, the flow path (201) formed in the sample processing chip (200) has a height of not less than 1 μm and not greater than 500 μm, and a width of not less than 1 μm and not greater than 500 μm. With this configuration, even when the first liquid (21) is sent into the small flow path (201) having a height of not less than 1 μm and not greater than 500 μm, and a width of not less than 1 μm and not greater than 500 μm, the liquid can be sent with the flow accurately controlled.

In this case, preferably, the flow path (201) formed in the sample processing chip (200) has a height of not less than 1 μm and not greater than 250 μm, and a width of not less than 1 μm and not greater than 250 μm. With this configuration, even when the first liquid (21) is sent into a smaller flow path (201) having a height of not less than 1 μm and not greater than 250 μm, and a width of not less than 1 μm and not greater than 250 μm, the liquid can be sent with the flow accurately controlled.

In the liquid sending method according to the first aspect described above, preferably, a plurality of types of liquids including the first liquid (21) are introduced into the flow path (201) in the sample processing chip (200). With this configuration, the relative amounts between the first liquid (21) and another liquid introduced into the sample processing chip (200) can be accurately controlled, and thus, the processing in the sample processing chip (200) can be accurately performed.

A liquid sending apparatus (100) according to a second aspect of the present invention is a liquid sending apparatus (100) configured to send liquid to a sample processing chip (200) having a flow path (201) formed therein, the liquid sending apparatus (100) including: a sensor (12) configured to measure a flow of a second liquid (22) which is different from a first liquid (21) which is introduced into the flow path (201) in the sample processing chip (200); a controller (10) programmed to control the flow of the second liquid (22) on the basis of the measured flow; and a liquid sending portion (11) configured to introduce the first liquid (21) into the flow path (201) in the sample processing chip (200) by means of the second liquid (22) of which flow is controlled.

As described above, the liquid sending apparatus (100) according to the second aspect is provided with: the sensor (12) configured to measure the flow of the second liquid (22) which is different from the first liquid (21) which is introduced into the flow path (201) in the sample processing chip (200); the controller (10) programmed to control the flow of the second liquid (22) on the basis of the measured flow; and the liquid sending portion (11) configured to introduce the first liquid (21) into the flow path (201) in the sample processing chip (200) by means of the second liquid (22) sent on the basis of the controlled flow. Thus, since the first liquid (21) is sent by means of the second liquid (22), the second liquid (22) can be inhibited from being compressed, different from a case where the first liquid (21) is sent by causing the pressure of gas to act thereon. Accordingly, the flow of the first liquid (21) can be accurately controlled. In addition, since feedback-control can be performed by measuring the flow of the second liquid (22), there is no need to provide a sensor in the flow path for the first liquid (21). Thus, also when a plurality of the first liquids (21) are each processed by use of the sample processing chip (200), there is no need to wash or replace the flow path provided with a sensor, for each processing. As a result, the problem of sample contamination when a plurality of samples are processed can be effectively solved. Thus, when processing of a liquid is performed by use of the sample processing chip (200) having the flow path (201) formed therein, the flow of the liquid, such as a sample specimen or a reagent, that is introduced into the flow path (201) in the chip can be accurately controlled while occurrence of sample contamination when a plurality of samples are processed is prevented. This effect is especially advantageous when the first liquid (21) is supplied to and processed in a micro flow path where fine flow control is performed.

In the liquid sending apparatus (100) according to the second aspect described above, preferably, the controller (10) is programmed to control a flow of the first liquid (21) which is introduced into the flow path (201) in the sample processing chip (200) by controlling the flow of the second liquid (22) caused by the liquid sending portion (11). With this configuration, since the flow of the first liquid (21) can be controlled through the control of the flow of the second liquid (22), which is liquid being less likely to be compressed when compared with gas, it is possible to accurately control the flow of the first liquid (21) without providing a sensor for measuring the flow to the flow path (201) for the first liquid (21).

In the liquid sending apparatus (100) according to the second aspect described above, preferably, the sensor measures the flow by measuring at least one of flow rate, flow velocity, and pressure. The flow rate is the volume or the mass of a liquid that passes per unit time. The flow velocity is a representative linear velocity of the liquid. The representative linear velocity is the mean velocity, the maximum velocity, or the like, for example. The pressure is the pressure of the liquid. With this configuration, by controlling the flow including at least one of the flow rate, the flow velocity, and the pressure of the second liquid (22), it is possible to accurately control the flow including at least one of the flow rate, the flow velocity, and the pressure of the first liquid (21).

In the liquid sending apparatus (100) according to the second aspect described above, preferably, the second liquid (22) is a liquid having immiscibility with the first liquid (21). In a case where the second liquid (22) has immiscibility with the first liquid (21), when the second liquid (22) comes into contact with the first liquid (21), a boundary is generated therebetween, and two phases are formed. For example, the second liquid (22) has solubility of less than 1 percent by volume with respect to the first liquid (21). That is, immiscibility encompasses not only a property of a substance allowing no portion thereof to be mixed with another substance at all but also a property of a substance allowing substantially no portion thereof to be mixed with another substance. That is, the second liquid (22) may be slightly mixed with the first liquid (21). With this configuration, even when the second liquid (22) is brought into contact with the first liquid (21), it is possible to suppress mixing of the second liquid (22) into the first liquid (21) to cause dilution of the first liquid (21), and mixing of impurities into the first liquid (21).

In this case, preferably, the first liquid (21) is a liquid serving as one of an aqueous phase and an oil phase, and the second liquid (22) is a liquid serving as another of the aqueous phase and the oil phase. With this configuration, if one of the first liquid (21) and the second liquid (22) is set as an oil phase, and the other of the first liquid (21) and the second liquid (22) is set as an aqueous phase, the first liquid (21) and the second liquid (22) can be easily prevented from being mixed with each other.

In a case where the second liquid (22) is a liquid that is less likely to be mixed with the first liquid (21), preferably, the second liquid (22) is a liquid that is a liquid having a specific gravity different from that of the first liquid (21). With this configuration, even when the second liquid (22) is introduced into a container containing the first liquid (21), the first liquid (21) and the second liquid (22) can be separated from each other in the up-down direction, due to the difference in specific gravity.

In the liquid sending apparatus (100) according to the second aspect described above, preferably, when a plurality of samples are each processed by use of the sample processing chip (200), the second liquid (22) is a liquid to be used in common among processes performed on the respective samples. With this configuration, the flow path that is provided with the sensor (12) for measuring the flow of the second liquid (22) need not be washed or replaced, for each sample. Thus, the number of the sensors (12) to be provided can be minimized, and work can be simplified.

In the liquid sending apparatus (100) according to the second aspect described above, preferably, when a plurality of samples are each processed by use of the sample processing chip (200), the first liquid (21) is a liquid that has a different liquid composition or a different source of a target component for each of the plurality of samples. With this configuration, if different flow paths (201) for the first liquids (21) respectively having different components are provided for the respective samples, the different samples can be inhibited from being mixed with one another.

In the liquid sending apparatus (100) according to the second aspect described above, preferably, the first liquid (21) is a solution that contains at least one of a sample, a reagent, and particles. With this configuration, while the flow of the solution containing at least one of the sample, the reagent, and the particles is accurately controlled, the solution can be sent.

In this case, preferably, the first liquid (21) is a solution that contains a nucleic acid derived from blood, magnetic particles, and a reagent for polymerase chain reaction. With this configuration, while the flow of the solution containing the nucleic acid derived from blood, the magnetic particles, and the reagent for polymerase chain reaction is accurately controlled, the solution can be sent.

In the liquid sending apparatus (100) according to the second aspect described above, preferably, the second liquid (22) is a liquid that contains an oil being in a liquid state at room temperature. The room temperature is a temperature about 20° C., and includes a temperature in a range of not lower than 0° C. and not higher than 40° C. With this configuration, when the first liquid (21) is processed at room temperature, the first liquid (21) can be easily sent by means of the second liquid (22) in a liquid state.

In the liquid sending apparatus (100) according to the second aspect described above, preferably, the liquid sending portion (11) introduces the first liquid (21) into the flow path (201) in the sample processing chip (200) at a flow rate of not less than 0.1 μL/minute and not greater than 5 mL/minute. With this configuration, the flow rate of the first liquid (21) of not less than 0.1 μL/minute and not greater than 5 mL/minute can be accurately controlled.

In this case, preferably, the liquid sending portion (11) introduces the first liquid (21) into the flow path (201) in the sample processing chip (200) at a flow rate of not less than 0.1 μL/minute and not greater than 1 mL/minute. With this configuration, by the first liquid (21) being sent at a flow rate of not greater than 1 mL/minute, a high throughput in IVD can be realized.

In the liquid sending apparatus (100) according to the second aspect described above, preferably, in addition to the introducing of the first liquid (21), a dispersion medium (23) for emulsion formation is introduced into the flow path (201) in the sample processing chip (200) to perform emulsion formation, and dispersoids are formed from the first liquid (21) at a rate of not less than 600 droplets/minute and not greater than 600 million droplets/minute. An emulsion is a milky liquid in which minute particles, as dispersoids, of a liquid are dispersed in another liquid that is immiscible therewith. With this configuration, an emulsion including the first liquid (21) as dispersoids can be formed while the flow of the first liquid (21) is accurately controlled, and thus, variation in the particle diameter of the dispersoids can be suppressed. In addition, emulsion droplets having a substantially uniform particle diameter can be efficiently formed at a rate of not less than 600 droplets/minute and not greater than 600 million droplets/minute.

In this case, preferably, in addition to the introducing of the first liquid (21), a dispersion medium (23) for emulsion formation is introduced into the flow path (201) in the sample processing chip (200) to perform emulsion formation, and dispersoids are formed from the first liquid (21) at a rate of not less than 3000 droplets/minute and not greater than 18 million droplets/minute. With this configuration, emulsion droplets having a substantially uniform particle diameter can be efficiently formed at a rate of not less than 3000 droplets/minute and not greater than 18 million droplets/minute.

In the liquid sending apparatus (100) according to the second aspect described above, preferably, in addition to the introducing of the first liquid (21), a dispersion medium (23) for emulsion formation is introduced into the flow path (201) in the sample processing chip (200) to perform emulsion formation, and dispersoids having a mean particle diameter of not less than 0.1 µm and not greater than 500 µm are formed from the first liquid (21). With this configuration, an emulsion including the first liquid (21) as dispersoids can be formed while the flow of the first liquid (21) is accurately controlled, and thus, variation in the particle diameter of the dispersoids can be suppressed. In addition, emulsion droplets having a substantially uniform particle diameter and having a mean particle diameter of not less than 0.1 µm and not greater than 500 µm can be efficiently formed.

In this case, preferably, in addition to the introducing of the first liquid (21), a dispersion medium (23) for emulsion formation is introduced into the flow path (201) in the sample processing chip (200) to perform emulsion formation, and dispersoids having a mean particle diameter of not less than 0.1 µm and not greater than 200 µm are formed from the first liquid (21). With this configuration, an emulsion including dispersoids having a mean particle diameter of not greater than 200 µm which is suitable for bio-measurement can be efficiently formed.

In the liquid sending apparatus (100) according to the second aspect described above, preferably, the flow path (201) formed in the sample processing chip (200) has a cross-sectional area of not less than 0.01 µm² and not greater than 10 mm². The cross-sectional area of the flow path (201) is the cross-sectional area thereof in a cross section orthogonal to the flowing direction of the liquid in the flow path (201). With this configuration, even in a case where the flow is small and difficult to be maintained to be constant, the liquid can be sent with the flow finely controlled. Thus, even when the first liquid (21) in a small flow is sent into the flow path (201) having a small cross-sectional area of not less than 0.01 µm² and not greater than 10 mm², the liquid can be sent with the flow accurately controlled.

In this case, preferably, the flow path (201) formed in the sample processing chip (200) has a cross-sectional area of not less than 0.01 µm² and not greater than 1 mm². With this configuration, even when the first liquid (21) in a smaller flow is sent into the flow path (201) having a cross-sectional area of not greater than 1 mm², the liquid can be sent with the flow accurately controlled.

In the above-described configuration in which the flow path (201) formed in the sample processing chip (200) has a cross-sectional area of not less than 0.01 µm² and not greater than 1 mm², preferably, the flow path (201) formed in the sample processing chip (200) has a height of not less than 1 µm and not greater than 500 µm, and a width of not less than 1 µm and not greater than 500 µm. With this configuration, even when the first liquid (21) is sent into the small flow path (201) having a height of not less than 1 µm and not greater than 500 µm, and a width of not less than 1 µm and not greater than 500 µm, the liquid can be sent with the flow accurately controlled.

In this case, preferably, the flow path (201) formed in the sample processing chip (200) has a height of not less than 1 µm and not greater than 250 µm, and a width of not less than 1 µm and not greater than 250 µm. With this configuration, even when the first liquid (21) is sent into a smaller flow path (201) having a height of not less than 1 µm and not greater than 250 µm, and a width of not less than 1 µm and not greater than 250 µm, the liquid can be sent with the flow accurately controlled.

In the liquid sending apparatus (100) according to the second aspect described above, preferably, a plurality of types of liquids including the first liquid (21) are introduced into the flow path (201) in the sample processing chip (200). With this configuration, the relative amounts between the first liquid (21) and another liquid introduced into the sample processing chip (200) can be accurately controlled, and thus, the processing in the sample processing chip (200) can be accurately performed.

The liquid sending apparatus (100) according to the second aspect described above preferably includes a first container (14a) disposed at an introduction passage between the sensor (12) and an inlet of the flow path (201) in the sample processing chip (200), the first container (14a) containing the first liquid (21), wherein the liquid sending portion (11) introduces the first liquid (21) into the flow path (201) in the sample processing chip (200) by causing the second liquid (22) to flow into the first container (14a). With this configuration, the first liquid (21) can be pushed in the first container (14a) by means of the second liquid (22), to be sent out of the first container (14a). Thus, the first liquid (21) can be accurately sent into the flow path (201) in the sample processing chip (200).

The liquid sending apparatus (100) according to the second aspect described above preferably includes a second container (13) disposed at an introduction passage between the liquid sending portion (11) and the sensor (12), the second container (13) containing the second liquid (22), wherein the liquid sending portion (11) sends the second liquid (22) by applying pressure to the second container (13). With this configuration, different from a case where pressure is applied to the liquid sending portion (11) through the second liquid (22), gas is caused to pass through the liquid sending portion (11), and thus, the second liquid (22) can be inhibited from remaining in and soiling the liquid sending portion (11) at the time of stop.

In the liquid sending apparatus (100) according to the second aspect described above, preferably, the first liquid (21) is a solution that contains a sample, and a plurality of sample containers each containing the first liquid (21) and a plurality of the sample processing chips (200) are provided. With this configuration, a plurality of samples can be efficiently processed by use of the plurality of the sample processing chips (200).

The liquid sending apparatus (100) according to the second aspect described above preferably includes a reservoir (14b) connected to an inlet of the flow path (201) in the sample processing chip (200), the reservoir (14b) containing the first liquid (21), wherein the liquid sending portion (11) introduces the first liquid (21) into the flow path (201) in the sample processing chip (200) through the inlet of the flow path (201) by causing the second liquid (22) to flow into the reservoir (14b). With this configuration, the first liquid (21) can be pushed in the reservoir (14b) by means of the second liquid (22), to be sent out of the reservoir (14b). Thus, the first liquid (21) can be accurately sent into the flow path (201) in the sample processing chip (200).

In the liquid sending apparatus (100) according to the second aspect described above, preferably, the first liquid (21) is a solution that contains a sample, and a plurality of the sample processing chips (200) each provided with a reservoir (14b) containing the first liquid (21) are provided. With this configuration, for each sample, the sample processing chip (200) provided with the reservoir (14b) can be prepared to perform processing. Thus, a plurality of samples can be efficiently processed while different samples are inhibited from being mixed with one another.

In the liquid sending apparatus (100) according to the second aspect described above, preferably, the sensor (12) is embedded in a flow path for the second liquid (22). With this configuration, the flow of the second liquid (22) can be accurately measured by the sensor (12) embedded in the flow path.

When processing of a liquid is performed by use of a sample processing chip having a flow path formed therein, the flow of the liquid, such as a sample specimen or a reagent, that is introduced into the flow path in the chip can be accurately controlled, and the problem of sample contamination when a plurality of samples are processed can be solved.

BRIEF DESCRIPTION OF THE DRAWINGS

FIG. 48 is a diagram describing how reaction in immunoassay proceeds;

FIG. 49 is a table showing one example of correspondence relationship between the steps, and the first liquid and the second liquid;

FIG. 50 is a diagram showing a liquid sending apparatus according to Examples 1 and 2;

FIG. 51 is a table showing an experiment condition of Example 1;

FIG. 52 is a table showing an experiment condition of Example 2;

FIG. 55 is a diagram showing a liquid sending apparatus according to Comparative Examples 1 and 2;

FIG. 56 is a table showing an experiment condition of Comparative Example 1;

FIG. 57 is a table showing an experiment condition of Comparative Example 2;

DETAILED DESCRIPTION OF THE PREFERRED EMBODIMENTS

Figure 1:
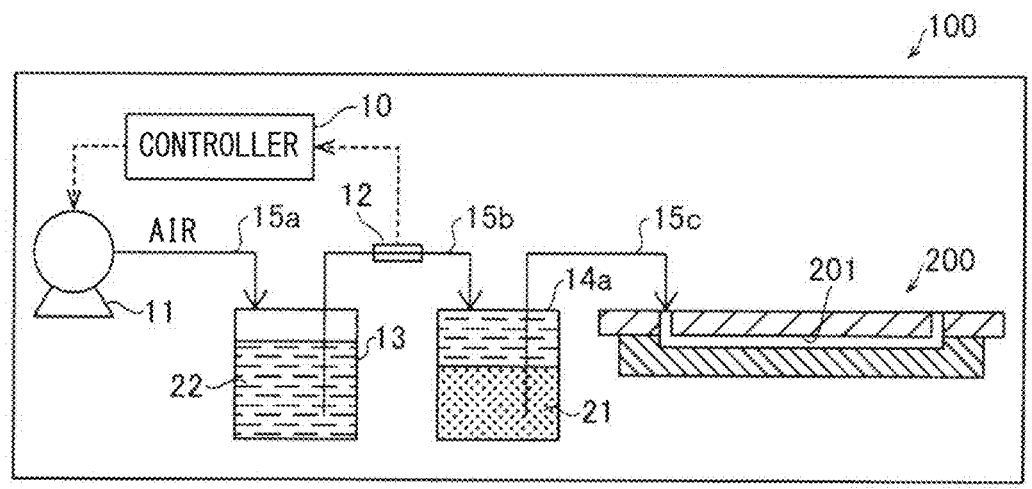
FIG. 1 is a diagram showing a first example of a liquid sending method.

Hereinafter, embodiments are described with reference to the drawings.

[Outline of Liquid Sending Method]

The outline of a liquid sending method according to the present embodiment is described with reference to FIG. 1.

The liquid sending method according to the present embodiment is a method for sending liquid to a sample processing chip 200 having a flow path 201 formed therein.

The sample processing chip 200 is a chip to be set in a liquid sending apparatus 100, and for performing sample processing including one or a plurality of process steps on a target component in a first liquid 21 supplied by the liquid sending apparatus 100. The sample processing chip 200 is configured to be able to receive the first liquid 21 containing a target component. The sample processing chip 200 is a cartridge-type sample processing chip which allows, by being set in the liquid sending apparatus 100, sample processing to be performed by the liquid sending apparatus 100.

The sample processing chip 200 is a microfluidic chip provided with fine flow paths for performing desired process steps, as described later. Each flow path is a micro flow path of which cross-sectional dimensions (width, height, inner diameter) are each 0.1 µm to 1000 µm, for example.

Into the sample processing chip 200, a liquid such as a body fluid or blood (whole blood, serum, or plasma) collected from a patient, or a sample obtained by subjecting the collected body fluid or blood to predetermined pretreatment is injected. The target component is, for example, nucleic acid such as DNA (deoxyribonucleic acid), a cell, an intracellular substance, an antigen or an antibody, a protein, a peptide, or the like. For example, when the target component is a nucleic acid, an extract of the nucleic acid extracted from blood or the like through predetermined pretreatment is injected into the sample processing chip 200.

The sample containing the target component and injected into the sample processing chip 200 is sent in the sample processing chip 200 by the liquid sending apparatus 100. While the sample is sent, processing on the target component through one or a plurality of steps is performed in a predetermined order. As a result of the target-component processing, a measurement specimen appropriate for analyzing the sample, or a liquid specimen appropriate for subsequent processing using another apparatus is generated in the sample processing chip 200.

In the liquid sending method of the present embodiment, the first liquid 21 is sent into the flow path 201 in the sample processing chip 200 by the liquid sending apparatus 100. As shown in FIG. 1, the liquid sending apparatus 100 includes a controller 10, a liquid sending portion 11, a sensor 12, a second container 13, and a first container 14a.

While accurately controlling a flow including at least one of the flow rate, the flow velocity, and the pressure of the first liquid 21, the liquid sending apparatus 100 sends the liquid into the flow path 201 in the sample processing chip 200. The flow path 201 in the sample processing chip 200 is a micro flow path, and the flow rate of the flowing-in liquid also becomes small. The liquid sending method of the present embodiment accurately controls such a flow rate.

In the present embodiment, a flow is obtained which includes at least one of the flow rate, the flow velocity, and the pressure of a second liquid 22 which is different from the first liquid 21 which is introduced into the flow path 201 in the sample processing chip 200. Specifically, the flow of the second liquid 22 is measured by the sensor 12 provided at a flow path 15b for the second liquid 22. Specifically, the sensor 12 measures at least one of the flow rate, the flow velocity, and the pressure, thereby measuring the flow. On the basis of the measured flow, the flow of the second liquid 22 is controlled. Specifically, on the basis of the obtained flow of the second liquid 22, the liquid sending portion 11 is feedback-controlled by the controller 10. Then, by means of the second liquid 22 sent on the basis of the controlled flow, the first liquid 21 is introduced into the flow path 201 in the sample processing chip 200.

Thus, since the first liquid 21 is sent by means of the second liquid 22, the second liquid 22 can be inhibited from being compressed, different from a case where the first liquid 21 is sent by causing the pressure of gas to act thereon. Accordingly, the flow of the first liquid 21 can be accurately controlled. In addition, since feedback-control can be performed by measuring the flow of the second liquid 22, there is no need to provide a sensor in the flow path for the first liquid 21. Thus, also when a plurality of the first liquids 21 are each processed by use of the sample processing chip 200, there is no need to wash or replace the flow path provided with a sensor, for each processing. As a result, the problem of sample contamination when a plurality of samples are processed can be effectively solved. Thus, when processing of a liquid is performed by use of the sample processing chip 200 having the flow path 201 formed therein, the flow of the liquid, such as a sample specimen or a reagent, that is introduced into the flow path 201 in the chip can be accurately controlled while occurrence of sample contamination when a plurality of samples are processed is prevented. This effect is especially advantageous when the first liquid 21 is supplied to and processed in a micro flow path where fine flow control is performed.

The flow of the first liquid 21 which is introduced into the flow path 201 in the sample processing chip 200 is controlled through the control of the flow of the second liquid 22. Thus, since the flow of the first liquid 21 can be controlled through the control of the flow of the second liquid 22, which is liquid being less likely to be compressed when compared with gas, it is possible to accurately control the flow of the first liquid 21 without providing a sensor for measuring the flow to the flow path 201 for the first liquid 21.

The second liquid 22 is a liquid that has immiscibility with the first liquid 21. Immiscibility encompasses not only a property of a substance allowing no portion thereof to be mixed with another substance at all but also a property of a substance allowing substantially no portion thereof to be mixed with another substance. This means that the second liquid 22 may be slightly mixed with the first liquid 21. Accordingly, even when the second liquid 22 is brought into contact with the first liquid 21, it is possible to suppress mixing of the second liquid 22 into the first liquid 21 to cause dilution of the first liquid 21, and mixing of impurities into the first liquid 21.

For example, the first liquid 21 is a liquid serving as one of an aqueous phase and an oil phase, and the second liquid 22 is a liquid serving as the other of the aqueous phase and the oil phase. Thus, if one of the first liquid 21 and the second liquid 22 is set as an oil phase, and the other of the first liquid 21 and the second liquid 22 is set as an aqueous phase, the first liquid 21 and the second liquid 22 can be easily prevented from being mixed with each other.

For example, the second liquid 22 is a liquid having a specific gravity different from that of the first liquid 21. Accordingly, even when the second liquid 22 is introduced into a container containing the first liquid 21, the first liquid 21 and the second liquid 22 can be separated from each other in the up-down direction, due to the difference in specific gravity.

When a plurality of samples are each processed by use of the sample processing chip 200, the second liquid 22 is a liquid to be used in common among processes performed on the respective samples. Thus, the flow path that is provided with the sensor 12 for measuring the flow of the second liquid 22 need not be washed or replaced, for each sample. Thus, the number of the sensors 12 to be provided can be minimized, and work can be simplified.

The second liquid 22 is a liquid that contains an oil being in a liquid state at room temperature. The room temperature is a temperature about 20° C., and includes a temperature in a range of not lower than 0° C. and not higher than 40° C. When the first liquid 21 is processed at room temperature, the first liquid 21 can be easily sent by means of the second liquid 22 in a liquid state.

Specifically, the second liquid 22 is a liquid different from the first liquid 21 which is introduced into the flow path in the chip. Since a sample solution or a reagent solution serving as the first liquid 21 is usually hydrophilic, examples of the second liquid 22 include hydrophobic liquids. Examples of the second liquid 22 include oils, and a mineral oil, a synthetic hydrocarbon oil, a diester oil, a polyester oil, a polyglycol oil, a phenyl ether oil, a silicone oil, a fluorine oil, or the like can be used. In particular, as the second liquid 22, n-hexadecane, a mineral oil, or an olefinic hydrocarbon or a silicone oil having a carbon number of not less than 10 and not greater than 20 is preferably used. When a lipophilic liquid is used as the first liquid 21, a hydrophilic liquid may be used as the second liquid 22.

The first liquid 21 is sent so as to be pushed out by the second liquid 22. In this case, preferably, there is no gas phase between the second liquid 22 and the first liquid 21. That is, preferably, a boundary layer is formed by the first liquid 21 and the second liquid 22 being in contact with each other. However, the first liquid 21 and the second liquid 22 may be present in a discontinuous manner in which air, another liquid, or the like is present between the first liquid 21 and the second liquid 22. That is, even when a small amount of air is present between the first liquid 21 and the second liquid 22, the amount compressed by pressure is small and always a constant amount compression is performed, and thus, the flow of the first liquid 21 is substantially equivalent to the flow of the second liquid 22. Even when another liquid is present between the first liquid 21 and the second liquid 22, liquid is less likely to be compressed, and thus, the flow of the first liquid 21 is substantially equivalent to the flow of the second liquid 22.

When a plurality of samples are each processed by use of the sample processing chip 200, the first liquid 21 is a liquid that has a different liquid composition or a different source of a target component for each of the plurality of samples. That is, the first liquid 21 is a liquid for which contamination with another sample is preferably not caused. If different flow paths 201 for the first liquids 21 respectively having different components are provided for the respective samples, the different samples can be inhibited from being mixed with one another.

The first liquid 21 is a solution that contains at least one of a sample, a reagent, and particles. While the flow of the solution containing at least one of the sample, the reagent, and the particles is accurately controlled, the solution can be sent. Thus, a first solution containing at least one of a sample, a reagent, and particles can be accurately processed.

The first liquid 21 is a solution that contains a nucleic acid derived from blood, magnetic particles, and a reagent for polymerase chain reaction. While the flow of a solution containing a nucleic acid derived from blood collected from a patient, magnetic particles, and a reagent for polymerase chain reaction is accurately controlled, the solution can be sent. Thus, a first solution containing a nucleic acid derived from blood collected from a patient, magnetic particles, and a reagent for polymerase chain reaction can be accurately processed.

In the example of the liquid sending method shown in FIG. 1, the second liquid 22 is contained in the second container 13. To the second container 13, air is sent under pressure through a flow path 15a by the liquid sending portion 11. By the air being sent under pressure, the second liquid 22 is sent from the second container 13 through the flow path 15b into the first container 14a. When the second liquid 22 is sent, the flow of the second liquid 22 is measured by the sensor 12 provided at the flow path 15b. The measured flow of the second liquid 22 is transmitted to the controller 10. The controller 10 feedback-controls the liquid sending portion 11 on the basis of the flow of the second liquid 22.

The first liquid 21 is contained in the first container 14a. The second liquid 22 is caused to flow from the second container 13 through the flow path 15b into the first container 14a. By the amount by which the second liquid 22 is caused to flow in, the first liquid 21 is sent from the first container 14a through a flow path 15c into the flow path 201 in the sample processing chip 200.

Figure 2:
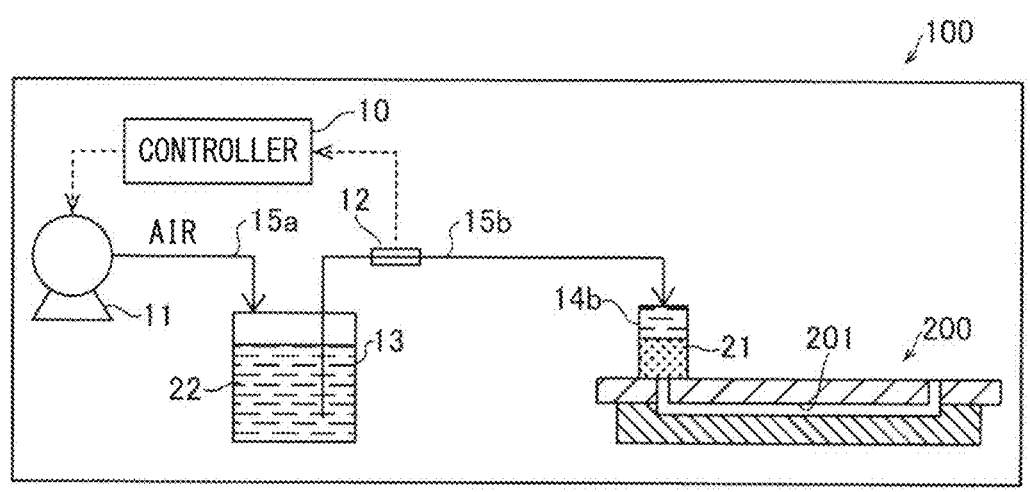
FIG. 2 is a diagram showing a second example of the liquid sending method.

In the example of the liquid sending method shown in FIG. 2, the second liquid 22 is contained in the second container 13. To the second container 13, air is sent under pressure through the flow path 15a by the liquid sending portion 11. By the air being sent under pressure, the second liquid 22 is sent from the second container 13 through the flow path 15b into a reservoir 14b. When the second liquid 22 is sent, the flow of the second liquid 22 is measured by the sensor 12 provided at the flow path 15b. The measured flow of the second liquid 22 is transmitted to the controller 10. The controller 10 feedback-controls the liquid sending portion 11 on the basis of the flow of the second liquid 22.

The first liquid 21 is contained in the reservoir 14b. The second liquid 22 is caused to flow from the second container 13 through the flow path 15b into the reservoir 14b. By the amount by which the second liquid 22 is caused to flow in, the first liquid 21 is sent from the reservoir 14b into the flow path 201 in the sample processing chip 200.

Figure 3:
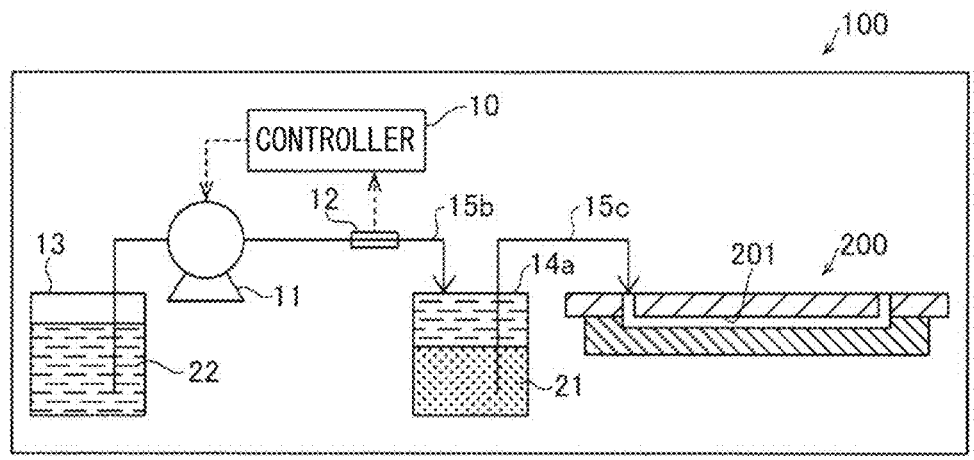
FIG. 3 is a diagram showing a third example of the liquid sending method.

In the example of the liquid sending method shown in FIG. 3, the second liquid 22 is contained in the second container 13. The second liquid 22 in the second container 13 is aspirated by the liquid sending portion 11 to be sent to the flow path 15b. When the second liquid 22 is sent, the flow of the second liquid 22 is measured by the sensor 12 provided at the flow path 15b. The measured flow of the second liquid 22 is transmitted to the controller 10. The controller 10 feedback-controls the liquid sending portion 11 on the basis of the flow of the second liquid 22.

The first liquid 21 is contained in the first container 14a. The second liquid 22 is caused to flow from the second container 13 through the flow path 15b into the first container 14a. By the amount by which the second liquid 22 is caused to flow in, the first liquid 21 is sent from the first container 14a through the flow path 15c into the flow path 201 in the sample processing chip 200.

Figure 4:
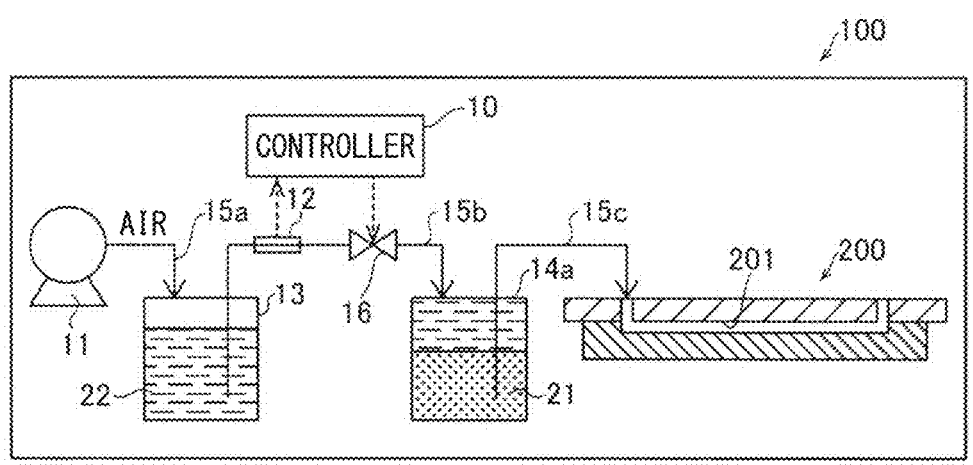
FIG. 4 is a diagram showing a fourth example of the liquid sending method.

In the example of the liquid sending method shown in FIG. 4, the second liquid 22 is contained in the second container 13. To the second container 13, air is sent under pressure through the flow path 15a by the liquid sending portion 11. By the air being sent under pressure, the second liquid 22 is sent from the second container 13 through the flow path 15b into the first container 14a. When the second liquid 22 is sent, the flow of the second liquid 22 is measured by the sensor 12 provided at the flow path 15b. The measured flow of the second liquid 22 is transmitted to the controller 10. The controller 10 feedback-controls a valve 16 on the basis of the flow of the second liquid 22. Accordingly, the flow of the second liquid 22 is controlled. That is, by the opening of the valve 16 being adjusted through the feedback-control, the flow of the second liquid 22 passing through the valve 16 is controlled.

The first liquid 21 is contained in the first container 14a. The second liquid 22 is caused to flow from the second container 13 through the flow path 15b into the first container 14a. By the amount by which the second liquid 22 is caused to flow in, the first liquid 21 is sent from the first container 14a through the flow path 15c into the flow path 201 in the sample processing chip 200.

With reference to FIG. 5 to FIG. 8, methods of sending the first liquid 21 according to the liquid sending method are described.

Figure 5:
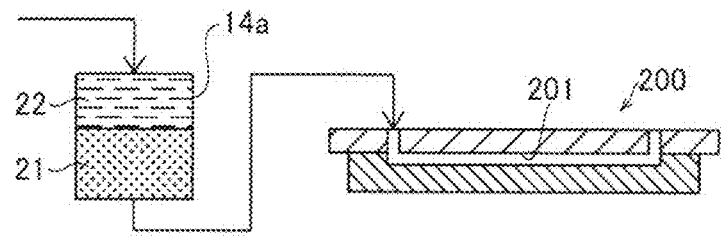
FIG. 5 is a diagram showing a first example of a container for a first liquid according to the liquid sending method.

In the example shown in FIG. 5, the first liquid 21 is contained in the first container 14a. The first liquid 21 has a greater specific gravity than the second liquid 22, and is located at the lower side of the first container 14a. In this case, the second liquid 22 is supplied from the upper part of the first container 14a, and the first liquid 21 is caused to flow out from the lower part of the first container 14a. Accordingly, the first liquid 21 and the second liquid 22 can be inhibited from being mixed with each other, and the first liquid 21 can be smoothly sent into the flow path 201 in the sample processing chip 200.

Figure 6:
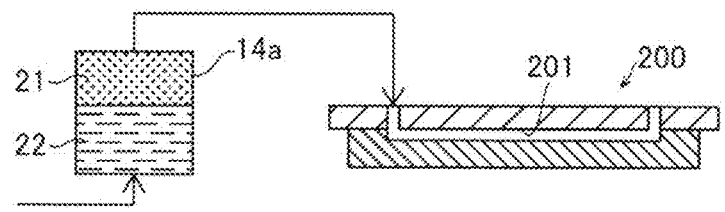
FIG. 6 is a diagram showing a second example of the container for the first liquid according to the liquid sending method.

In the example shown in FIG. 6, the first liquid 21 is contained in the first container 14a. The first liquid 21 has a smaller specific gravity than the second liquid 22, and is located at the upper side of the first container 14a. In this case, the second liquid 22 is supplied from the lower part of the first container 14a, and the first liquid 21 is caused to flow out from the upper part of the first container 14a. Accordingly, the first liquid 21 and the second liquid 22 can be inhibited from being mixed with each other, and the first liquid 21 can be smoothly sent into the flow path 201 in the sample processing chip 200.

Figure 7:
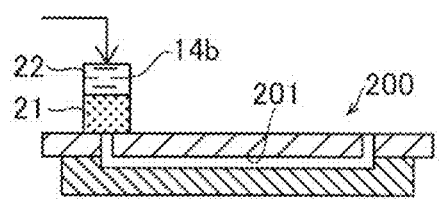
FIG. 7 is a diagram showing a third example of the container for the first liquid according to the liquid sending method.

In the example shown in FIG. 7, the first liquid 21 is contained in the reservoir 14b provided above the sample processing chip 200. The first liquid 21 has a greater specific gravity than the second liquid 22, and is located at the lower side of the reservoir 14b. In this case, the second liquid 22 is supplied from the upper part of the reservoir 14b, and the first liquid 21 is caused to flow out from the lower part of the reservoir 14b. Accordingly, the first liquid 21 and the second liquid 22 can be inhibited from being mixed with each other, and the first liquid 21 can be smoothly sent into the flow path 201 in the sample processing chip 200.

Figure 8:
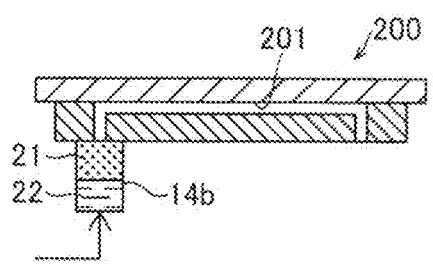
FIG. 8 is a diagram showing a fourth example of the container for the first liquid according to the liquid sending method.

In the example shown in FIG. 8, the first liquid 21 is contained in the reservoir 14b provided below the sample processing chip 200. The first liquid 21 has a smaller specific gravity than the second liquid 22, and is located at the upper side of the reservoir 14b. In this case, the second liquid 22 is supplied from the lower part of the reservoir 14b, and the first liquid 21 is caused to flow out from the upper part of the reservoir 14b. Accordingly, the first liquid 21 and the second liquid 22 can be inhibited from being mixed with each other, and the first liquid 21 can be smoothly sent into the flow path 201 in the sample processing chip 200.

Into the flow path 201 in the sample processing chip 200, a plurality of liquids including the first liquid 21 are introduced. For example, in addition to the introducing of the first liquid 21, a dispersion medium 23 for emulsion formation is introduced into the flow path 201 in the sample processing chip 200. Since the relative amounts between the first liquid 21 and another liquid introduced into the sample processing chip 200 can be accurately controlled, the processing in the sample processing chip 200 can be accurately performed.

(First Liquid)

The first liquid 21 contains various components in accordance with the details of the processing. Sending of the first liquid 21 can be performed for such a first liquid 21 which contains various components.

Figure 9:
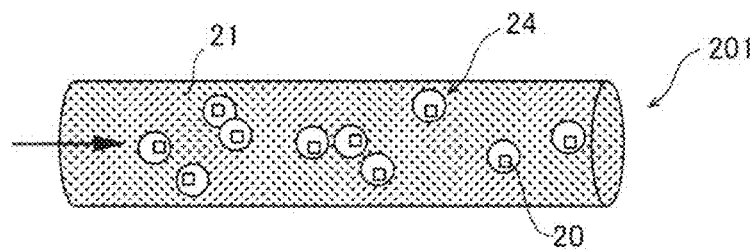
FIG. 9 is a diagram showing an example in which the first liquid contains droplets.

For example, as shown in FIG. 9, the first liquid 21 contains droplets 24. Inside each droplet 24, a component 20 as the processing target is encapsulated.

Figure 10:
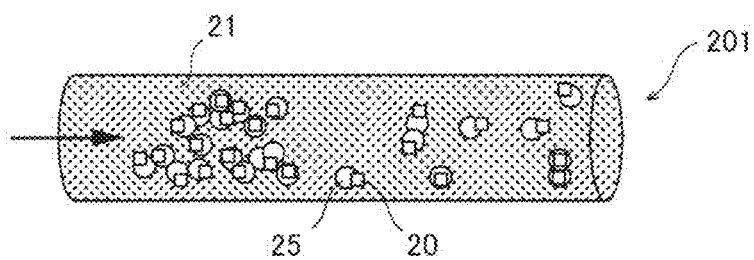
FIG. 10 is a diagram showing an example in which the first liquid contains a carrier.

For example, as shown in FIG. 10, the first liquid 21 contains a carrier 25. The carrier 25 is a solid carrier to which surface the component 20 as the processing target is bound.

Figure 11:
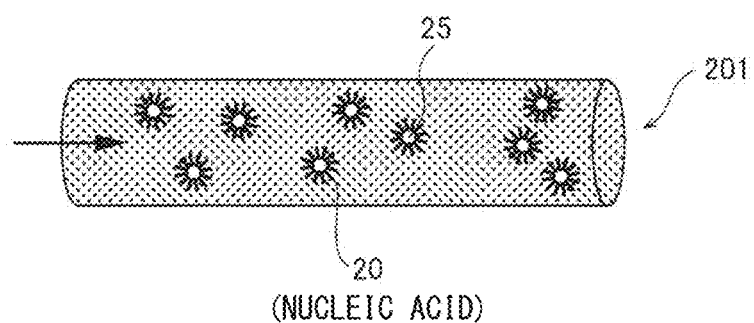
FIG. 11 is a diagram showing an example in which the first liquid contains the carrier bound to an amplification product of a nucleic acid.

For example, as shown in FIG. 11, the first liquid 21 contains a nucleic acid as the component 20. The carrier 25 including the nucleic acid is a carrier to which surface the nucleic acids are bound in such a manner as to cover the surface, the nucleic acids being amplification products obtained through a process of amplifying the nucleic acid.

(Flow Path)

The sample processing chip 200 includes: a fluid module 220 having the flow path 201 formed therein; and a base plate 210, for example. Into the flow path 201 in the sample processing chip 200, various types of fluids such as a liquid containing a target component 20, a liquid to be used in processing of the target component 20, and gas can be introduced. The flow path 201 has a tubular shape surrounded by the inner wall surface.

The flow path 201 in the sample processing chip 200 may have any structure as long as the liquid injected from the inlet portion of the sample processing chip 200 can flow therethrough. The flow path 201 has a shape in accordance with the processing to be performed in the flow path. The flow path 201 is formed so as to have a flow path width, a flow path height or flow path depth, a flow path length, and a volume that are in accordance with the processing to be performed in the flow path. The flow path 201 is formed as a passage or channel in an elongated tubular shape, for example. The channel can be in a linear shape, a curved shape, a zigzag shape, or the like. The flow path 201 may be in a shape in which flow path dimensions such as the flow path width and the height are varied (see FIG. 12), may be in a shape in which part or the entirety of the flow path extends in a planar manner (see FIG. 38), or may be in a chamber shape (not shown) in which the flowing-in liquid can be stored, for example.

Figure 12:
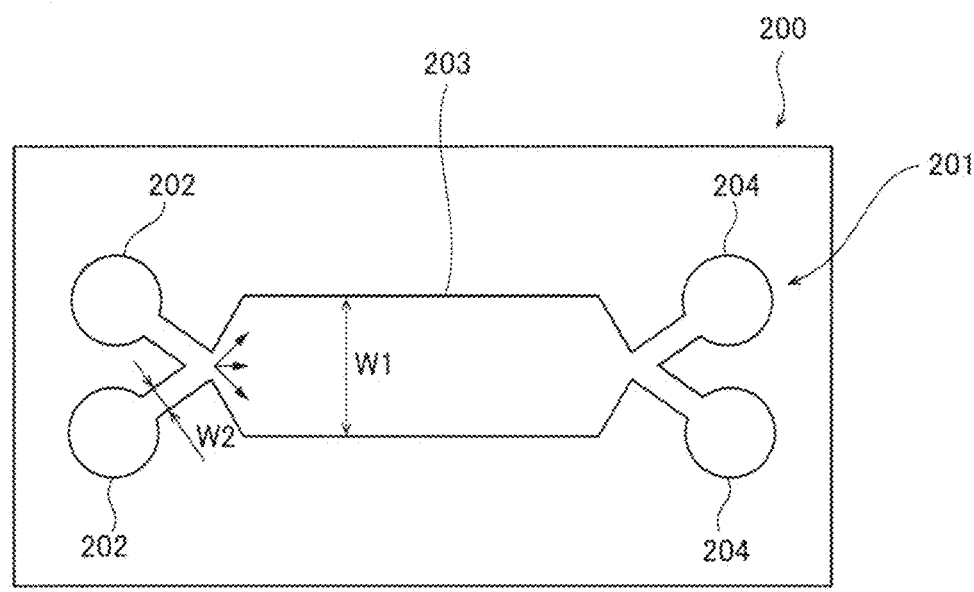
FIG. 12 is a schematic plan view showing a configuration example of a flow path.

As shown in FIG. 12, the flow path 201 has: a connection portion 202 provided at one end side; a channel 203 for performing processing on the first liquid 21; and a connection portion 204 provided at the other end side, for example. The connection portion 202, the channel 203, and the connection portion 204 may be provided in any numbers.

For example, the connection portion 202 is an inlet port for allowing a liquid to flow in. The first liquid 21 flows from the connection portion 202 into the channel 203. In the channel 203, processing on the first liquid 21 is performed. The first liquid 21 having been subjected to the processing flows from the channel 203 into the connection portion 204. The first liquid 21 is sent out through the connection portion 204 to another flow path 201 for performing the next processing or to the outside of the sample processing chip 200.

The channel 203 has a flow path width W1 which is greater than a flow path width W2 of the connection portion 202 or the connection portion 204, for example. That is, the channel 203 has a wide shape having a relatively great flow path width in the flow path 201. According to this configuration, the first liquid 21 can be widely distributed in the channel 203, and thus, the processing on the first liquid 21 can be efficiently performed.

Figure 13:
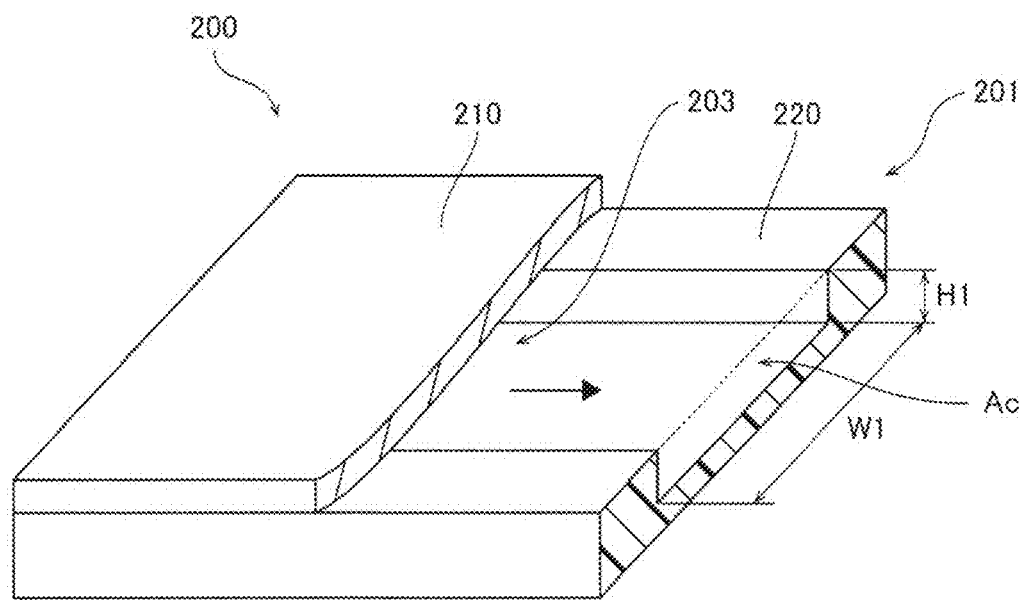
FIG. 13 is a schematic enlarged perspective cross-sectional view showing a cross section of a channel of the flow path shown in FIG. 12.

As shown in FIG. 13, for example, in the cross section of the channel 203, a width direction dimension W1 is greater than a height direction dimension H1. That is, the channel 203 that is flat and large in the width direction is formed. Accordingly, the first liquid 21 can be distributed in a flat manner in the channel 203 to be efficiently brought into contact with a process liquid. Thus, the processing on the first liquid 21 can be efficiently performed.

For example, the channel 203 (the flow path 201) has a cross-sectional area Ac of not less than 0.01 $\mu m^2$ and not greater than 10 $mm^2$. The "cross-sectional area of the channel 203" is the cross-sectional area thereof in a cross section orthogonal to the flowing direction of the liquid in the channel 203. Even in a case where the flow is small and is difficult to be maintained to be constant, the liquid can be sent with the flow finely controlled. Thus, even when the first liquid 21 in a small flow is sent into the flow path 201 having a small cross-sectional area of not less than 0.01 $\mu m^2$ and not greater than 10 $mm^2$, the liquid can be sent with the flow rate accurately controlled. Preferably, the channel 203 (the flow path 201) has the cross-sectional area Ac of not less than 0.01 $\mu m^2$ and not greater than 1 $mm^2$. More preferably, the channel 203 (the flow path 201) has the cross-sectional area Ac of not less than 0.01 $\mu m^2$ and not greater than 0.25 $mm^2$.

The flow path 201 formed in the sample processing chip 200 has a height of not less than 1 $\mu m$ and not greater than 500 $\mu m$, for example. Even when the first liquid 21 is sent into the small flow path 201 having a height of not less than 1 $\mu m$ and not greater than 500 $\mu m$, and a width of not less than 1 $\mu m$ and not greater than 500 $\mu m$, the liquid can be sent with the flow accurately controlled. Preferably, the flow path 201 has a height of not less than 1 $\mu m$ and not greater than 250 $\mu m$, and a width of not less than 1 $\mu m$ and not greater than 250 $\mu m$. More preferably, the flow path 201 has a height of not less than 1 $\mu m$ and not greater than 100 $\mu m$, and a width of not less than 1 $\mu m$ and not greater than 100 $\mu m$.

The flow path 201 is formed as a part of a fluid module which is a block body formed from resin, glass, or the like and having the flow path 201 formed therein. As the material forming the flow path 201 or the fluid module, a material appropriate for the processing to be performed in the flow path 201 is preferably employed. For example, polydimethylsiloxane (PDMS) and polymethyl methacrylate resin (PMMA) are each preferable as a hydrophobic material. Polycarbonate (PC) is preferable as a heat-resistant material. Polycarbonate, polystyrene (PS), or the like is preferable as a chemical-resistant material. Cycloolefin copolymer (COC) and cycloolefin polymer (COP) are each preferable for use in fluorescence detection or the like, as a material having low intrinsic fluorescence. Glass, polycarbonate, or the like is preferable in that the hydrophilicity thereof is high or hydrophilic processing is easy to be performed.

The flow of the fluid in the flow path 201 is roughly classified into laminar flow and turbulent flow. In the present embodiment, for example, when processing on the first liquid 21 is performed, the flow in the flow path 201 is in the form of a laminar flow.

The flow in the flow path 201 can be expressed by use of a Reynolds number Re. The Reynolds number Re is defined by the following formula (1).

$$Re = V \times d / v \quad (1)$$

where V[m/s] is the mean velocity of the flow in the flow path 201, d[m] is the inner diameter of the flow path 201, and v[$m^2$/s] is a coefficient of kinematic viscosity of the fluid.

In general, it is considered that when the Reynolds number Re is not greater than 2300, a laminar flow is formed. There is a tendency that the smaller the Reynolds number is, the smaller both the inner diameter of the flow path 201 and the flow velocity are.

For example, when processing on the first liquid 21 is performed, the Reynolds number of the flow in the flow path 201 is not greater than 2000. Preferably, when processing on the first liquid 21 is performed, the Reynolds number of the flow in the flow path 201 is not greater than 100. More preferably, when processing on the first liquid 21 is performed, the Reynolds number of the flow in the flow path 201 is not greater than 10. Further preferably, when processing on the first liquid 21 is performed, the Reynolds number of the flow in the flow path 201 is not greater than 1.

When the first liquid 21 is caused to flow in the flow path 201, the first liquid 21 is introduced into the flow path 201 in the sample processing chip 200 at a flow rate of not less than 0.1 μL/minute and not greater than 5 mL/minute, for example. The flow rate may be constant or varied in this range. Thus, the liquid sending method of the present embodiment can accurately control the flow rate of the first liquid 21 of not less than 0.1 μL/minute and not greater than 5 mL/minute. That is, since the flow rate of the second liquid 22 can be accurately measured by the sensor 12 in the range of not less than 0.1 μL/minute and not greater than 5 mL/minute, the flow rate of the first liquid 21 can be accurately controlled in the range of not less than 0.1 μL/minute and not greater than 5 mL/minute. Preferably, the first liquid 21 is introduced into the flow path 201 in the sample processing chip 200 at a flow rate of not less than 0.1 μL/minute and not greater than 1 mL/minute. Accordingly, a high throughput can be realized in IVD. More preferably, the first liquid 21 is introduced into the flow path 201 in the sample processing chip 200 at a flow rate of not less than 0.1 μL/minute and not greater than 200 μL/minute. Accordingly, during emulsion formation, droplets can be stably formed.

[Configuration Example of Sample Processing Chip]

Figure 14:
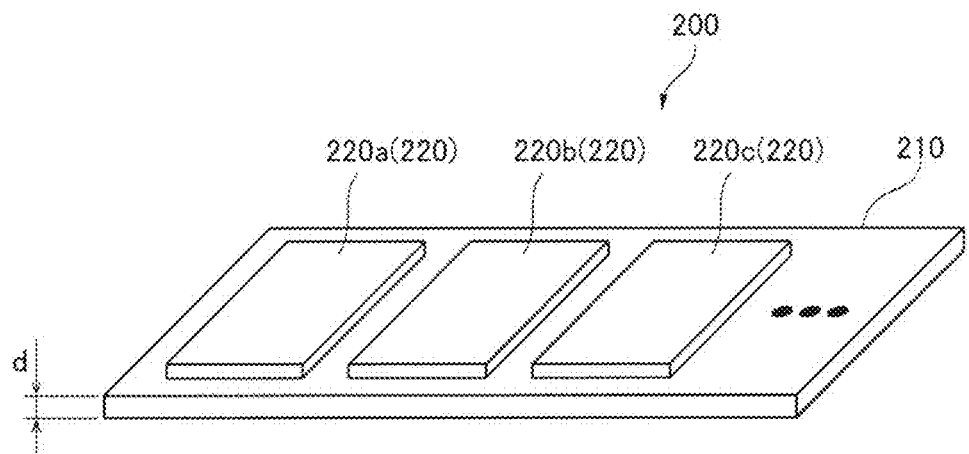
FIG. 14 is a perspective view showing a configuration example of a sample processing chip.

FIG. 14 shows a configuration example of the sample processing chip 200 of the present embodiment. A plurality of types of the fluid modules 220 having different functions are set on the base plate 210. In the example shown in FIG. 14, the first liquid 21 and the like are caused to sequentially flow through fluid modules 220a, 220b, and 220c, whereby an assay corresponding to a combination of the plurality of types of the fluid modules is performed. The fluid modules 220a, 220b, and 220c are different types of fluid modules, respectively. When the combination of the fluid modules 220 set on the base plate 210 is changed, various assays in accordance with the combination can be performed. The number of the fluid modules 220 set on the base plate 210 is not limited. The shape of the fluid module 220 may be different for each type.

Figure 15:
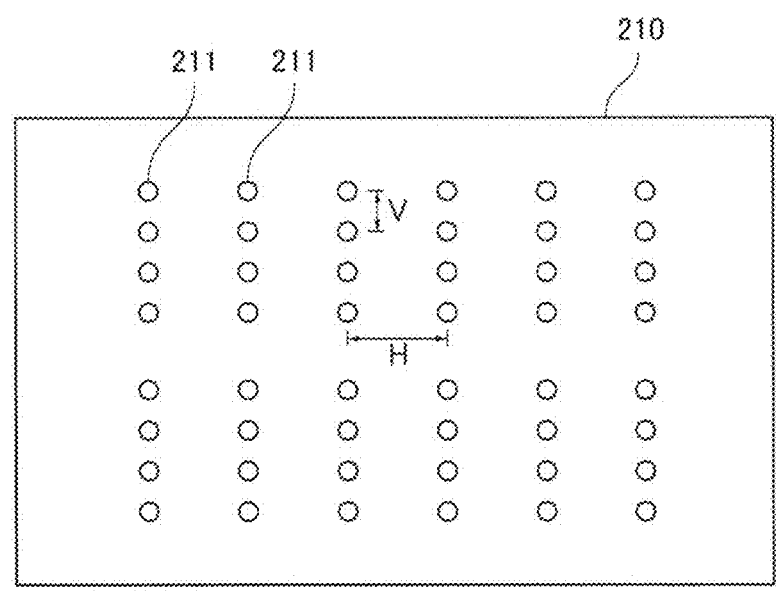
FIG. 15 is a plan view showing a configuration example of a base plate of the sample processing chip.

FIG. 15 shows a configuration example of the base plate 210. The base plate 210 has a plurality of base plate flow paths 211. The base plate 210 has a flat plate shape, and has a first face as the main surface, and a second face. The second face is the face at the reverse side of the first face. The base plate 210 is formed from resin or glass, for example.

The base plate 210 has a thickness d of not less than 1 mm and not greater than 5 mm, for example. Thus, the base plate 210 can be formed so as to have a sufficiently large thickness, compared with the flow path height (on the order of about 10 μm to 500 μm) of the flow path 201 formed in the fluid module 220. As a result, the base plate 210 can be easily ensured to have sufficient pressure resistance performance.

Each base plate flow path 211 is a through hole which penetrates the base plate 210 in the thickness direction thereof, for example. The base plate flow path 211 is connected to the flow path 201 in the fluid module 220. In addition, the base plate flow path 211 can function as a port for supplying a liquid or a reagent into the sample processing chip 200, or a port for collecting liquid from the sample processing chip 200.

In the example shown in FIG. 15, the base plate 210 has two sets of 4 rows×6 columns of the base plate flow paths 211. The number and the number of sets of the base plate flow paths 211 provided in the base plate 210 are not limited to those shown in the example in FIG. 15.

The base plate flow paths 211 are arranged at predetermined pitches, for example. In the example shown in FIG. 15, the base plate flow paths 211 are arranged at a pitch V in the vertical direction and at a pitch H in the horizontal direction. In this case, the fluid module 220 can be disposed on the base plate 210 at a desired position according to the pitch unit, so as to connect the flow path 201 to any desired base plate flow paths 211. The base plate flow paths 211 may be formed only at positions necessary for providing connection with various types of the fluid modules 220 disposed on the base plate 210.

Figure 16:
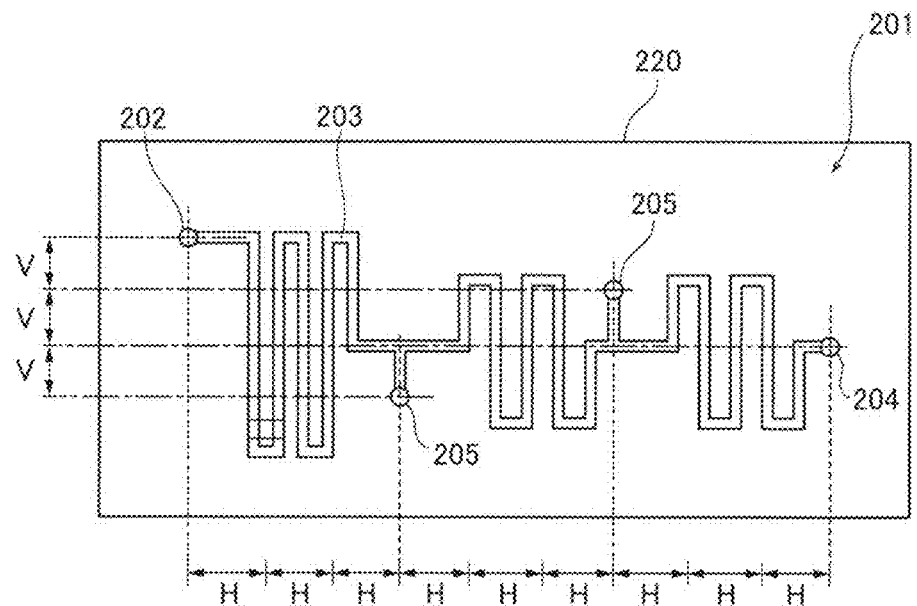
FIG. 16 is a plan view showing a configuration example of a fluid module.

FIG. 16 shows a configuration example of the fluid module 220. The connection portions 202, 204, and 205 are arranged on the fluid module 220 so as to match the pitches of the base plate flow paths 211 in the base plate 210. That is, the connection portions 202, 204, and 205 are arranged on the fluid module 220 at pitches of integer multiples of the pitches V and H of the base plate flow paths 211 in the base plate 210. The channel 203 is disposed so as to connect the connection portions 202, 204, and 205 arranged at predetermined pitches. A plurality of sets of the channel 203 and the connection portions 202, 204, and 205 arranged at predetermined pitches may be provided in the fluid module 220.

The fluid modules 220a to 220c may have different flow path shapes, respectively. Each fluid module 220 may be disposed not only on the first face but also on the second face. Alternatively, each fluid module 220 may be disposed only on the second face.

Figure 17:
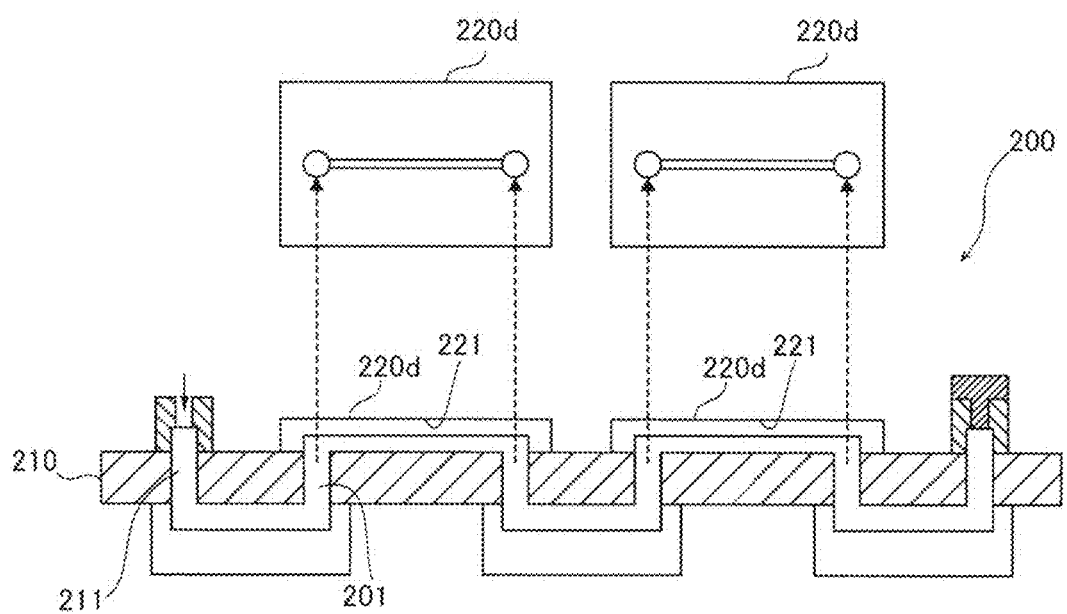
FIG. 17 is a longitudinal cross-sectional view showing a configuration example of the sample processing chip.

In the configuration example shown in FIG. 17, the sample processing chip 200 further includes fluid modules 220d. Each fluid module 220d is disposed at the second face which is at the reverse side of the first face of the base plate 210 where the fluid modules 220a to 220c are disposed. The fluid module 220d includes a flow path 221, and is a connection module having a function of connecting the fluid modules 220 with each other. The fluid module 220d serving as the connection module is not provided with a flow path for performing a process step on the first liquid 21. A flow path structure corresponding to a connection module may be formed in the base plate 210.

Each fluid module 220 (including the connection module) is connected to the base plate 210 through solid-phase welding, for example. As solid-phase welding, a method of subjecting surfaces to be joined to plasma processing to form OH radicals, thereby to join the surfaces by hydrogen bonds; a method of vacuum pressure welding; or the like can be employed, for example. Through solid-phase welding, the fluid module 220 and the base plate 210 can be firmly joined together. It should be noted that the fluid module 220 may be connected to the base plate 210 with an adhesive or the like.

In the example shown in FIG. 17, the base plate flow paths 211 in the base plate 210 function as ports for injecting liquid. In addition, the base plate flow paths 211 in the base plate 210 function as ports for collecting liquid. The ports may be provided in any number.

The first liquid 21 is injected into a base plate flow path 211 through a jig such as a connector. The jig such as a connector is connected to the end of a base plate flow path 211, among the base plate flow paths 211, at the opposite side to the end at the flow path 201 side. A desired base plate flow path 211 can be sealed by a plug being inserted into the connector.

[Configuration Example of Liquid Sending Apparatus]

Figure 18:
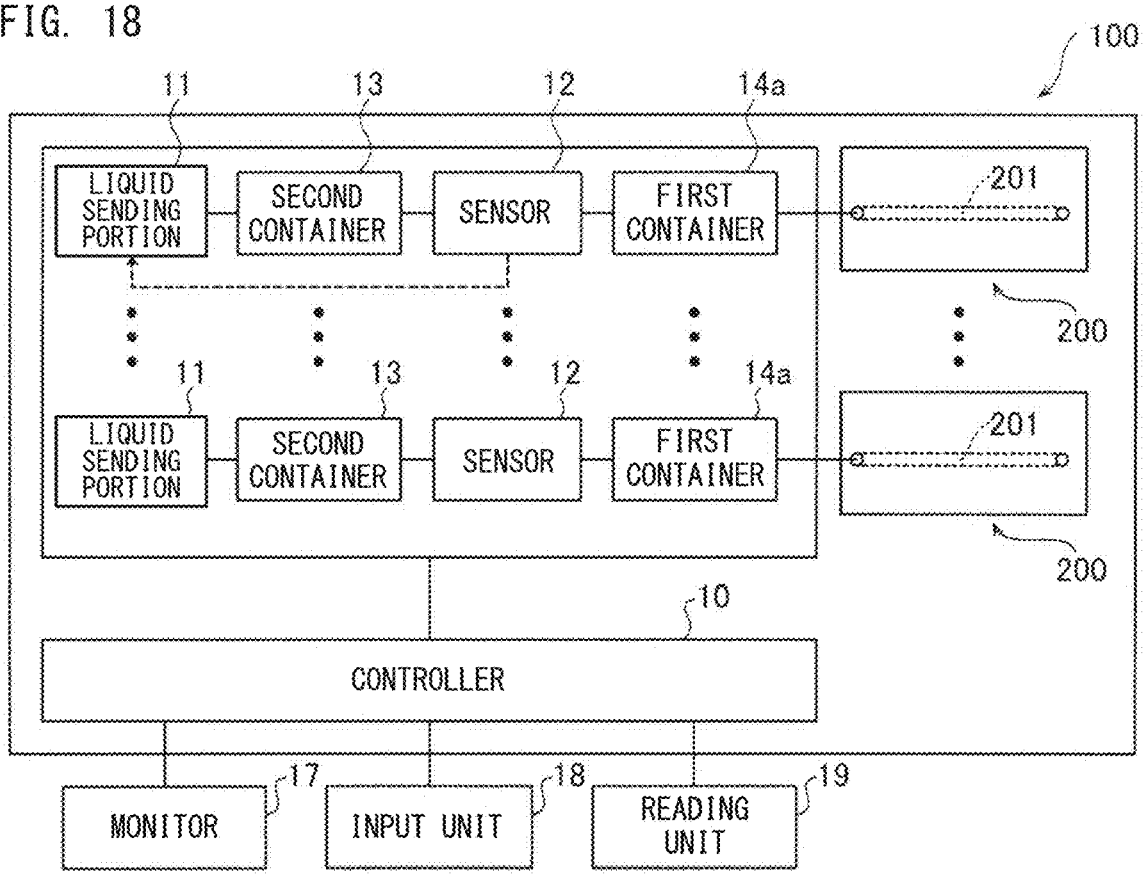
FIG. 18 is a block diagram showing a configuration example of a liquid sending apparatus.

FIG. 18 shows an outline of the liquid sending apparatus 100.

The liquid sending apparatus 100 is a liquid sending apparatus for sending liquid to the sample processing chip 200 having the flow path 201 formed therein. In the sample processing chip 200, sample processing on the first liquid 21 is performed. The details of the sample processing are determined in accordance with the sample processing chip 200 to be used. The liquid sending apparatus 100 can perform different types of sample processing in accordance with the type of the sample processing chip 200 to be used.

The liquid sending apparatus 100 includes the controller 10, the liquid sending portion 11, the sensor 12, the second container 13, and the first container 14*a*.

The controller 10 controls each section such that: the first liquid 21 is supplied into the flow path 201 in the sample processing chip 200; and processing on the first liquid 21 is performed.

When processing units to be used for various types of process steps are set in the liquid sending apparatus 100, the controller 10 may control the processing units. The units to be used for various types of process steps are, for example, a heater unit or a cooling unit for controlling the temperature of the liquid, a magnet unit for causing magnetic force to act on the liquid, a camera unit for taking images of the liquid, a detection unit for performing detection of the sample or the label in the liquid, and the like. These processing units are provided so as to correspond to at least any one of a plurality of the fluid modules 220, and are configured to operate when process steps are performed by means of the corresponding fluid module 220.

In the present embodiment, the controller 10 controls the flow of the second liquid 22 on the basis of a measurement result of the flow including at least one of the flow rate, the flow velocity, and the pressure. Specifically, the controller 10 measures, by means of the sensor 12, the flow including at least one of the flow rate, the flow velocity, and the pressure of the second liquid 22 which is different from the first liquid 21 which is introduced into the flow path 201 in the sample processing chip 200. Then, the controller 10 controls the liquid sending portion 11 on the basis of the measurement result. That is, on the basis of the measurement result obtained by the sensor 12, the controller 10 performs feedback-control such that the flow of the second liquid 22 takes a desired value. The feedback-control may be performed by use of at least one of proportional control, integral control, and derivative control.

Thus, since the first liquid 21 is sent by means of the second liquid 22, the second liquid 22 can be inhibited from being compressed, different from a case where the first liquid 21 is sent by causing the pressure of gas to act thereon. Accordingly, the flow of the first liquid 21 can be accurately controlled. In addition, since feedback-control can be performed by measuring the flow of the second liquid 22, there is no need to provide a sensor in the flow path for the first liquid 21. Thus, also when a plurality of the first liquids 21 are each processed by use of the sample processing chip 200, there is no need to wash or replace the flow path provided with a sensor, for each processing. As a result, the problem of sample contamination when a plurality of samples are processed can be effectively solved. Thus, when processing of a liquid is performed by use of the sample processing chip 200 having the flow path 201 formed therein, the flow of the liquid, such as a sample specimen or a reagent, that is introduced into the flow path 201 in the chip can be accurately controlled and the problem of sample contamination when a plurality of samples are processed can be solved. This effect is especially advantageous when the first liquid 21 is supplied to and processed in a micro flow path where fine flow control is performed.

The controller 10 controls the flow of the second liquid 22 sent by the liquid sending portion 11, thereby controlling the flow of the first liquid 21 which is introduced into the flow path 201 in the sample processing chip 200. Thus, since the flow of the first liquid 21 can be controlled through the control of the flow of the second liquid 22, which is liquid being less likely to be compressed when compared with gas, it is possible to accurately control the flow of the first liquid 21 without providing a sensor for measuring the flow to the flow path 201 for the first liquid 21.

The controller 10 can individually control the operation of each liquid sending portion 11. By individually controlling each liquid sending portion 11, the controller 10 can perform liquid sending control in accordance with the combination of the fluid modules 220 provided to the sample processing chip 200.

The liquid sending portion 11 sends the second liquid 22 on the basis of the controlled flow, thereby introducing the first liquid 21 into the flow path 201 in the sample processing chip 200. The liquid sending portion 11 is a pump, for example. The liquid sending portion 11 may send the second liquid 22 by applying pressure to gas, or may send the second liquid 22 not via gas.

The liquid sending portion 11 applies pressure to the second liquid 22. As a result of the liquid sending portion 11 applying positive pressure or negative pressure, the second liquid 22 is sent out from the second container 13. The liquid sending portion 11 is a pressure pump which supplies air pressure, for example. Other than this, as the liquid sending portion 11, a syringe pump, a diaphragm pump, or the like can be employed.

Each sensor 12 measures the flow including at least one of the flow rate, the flow velocity, and the pressure of the second liquid 22 which is different from the first liquid 21 which is introduced into the flow path 201 in the sample processing chip 200. The sensor 12 may be embedded in the flow path for the second liquid 22. Accordingly, the flow of the second liquid 22 can be accurately measured by the sensor 12 embedded in the flow path.

In the configuration shown in FIG. 18, the sensor 12 detects the flow rate (example of the unit: μL/minute) of the second liquid 22. The sensor 12 feedbacks the detection result of the flow rate to the liquid sending portion 11. The liquid sending portion 11 controls the pressure in accordance with the feedback from the sensor 12. Specifically, the sensor 12 performs feedback to the controller 10. The controller 10 controls the pressure of the liquid sending portion 11 for transferring liquid on the basis of the flow rate measured by the sensor 12. The sensor 12 may measure the flow velocity of the second liquid 22. The sensor 12 may measure the pressure of the second liquid 22.

Each second container 13 is configured to contain the second liquid 22. The second container 13 is disposed on the introduction passage between the liquid sending portion 11 and the sensor 12. The liquid sending portion 11 applies pressure to the second container 13, thereby sending the second liquid 22. Accordingly, different from a case where pressure is applied to the liquid sending portion 11 through the second liquid 22, gas is caused to pass through the liquid sending portion 11, and thus, the second liquid 22 can be inhibited from remaining in and soiling the liquid sending portion 11 at the time of stop.

Each first container 14a is configured to contain the first liquid 21. The first container 14a is disposed on the introduction passage between the sensor 12 and the inlet of the flow path 201 in the sample processing chip 200. The liquid sending portion 11 causes the second liquid 22 to flow into the first container 14a, thereby introducing the first liquid 21 into the flow path 201 in the sample processing chip 200. Accordingly, the first liquid 21 can be pushed in the first container 14a by means of the second liquid 22, to be sent out of the first container 14a. Thus, the first liquid 21 can be accurately sent into the flow path 201 in the sample processing chip 200.

Figure 19:
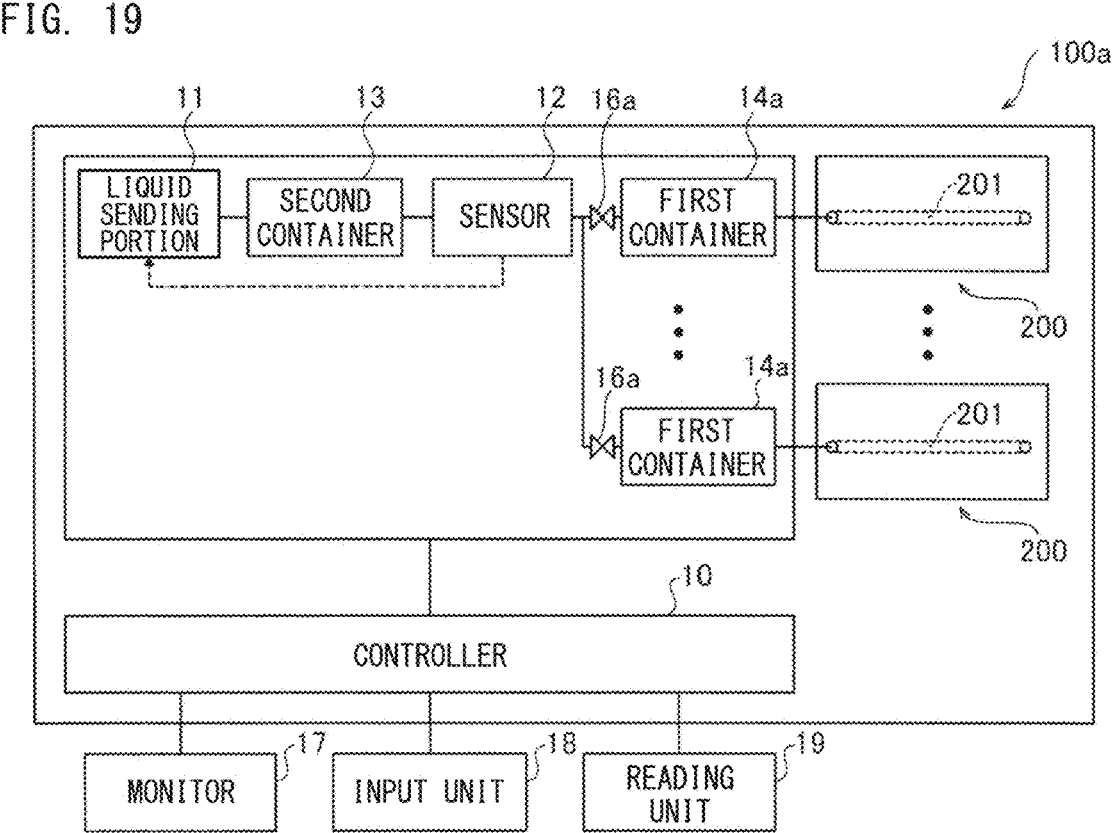
FIG. 19 is a block diagram showing another configuration example of the liquid sending apparatus.

The first liquid 21 is a solution that contains a sample. The first container 14a is a sample container that contains the first liquid 21. A plurality of the sample containers and a plurality of the sample processing chips 200 are provided. Accordingly, the plurality of samples can be efficiently processed by use of the plurality of the sample processing chips 200. The liquid sending portion 11, the second container 13, the sensor 12, and the first container 14a are provided for each of the plurality of the sample processing chips 200. It should be noted that, as in a liquid sending apparatus 100a shown in FIG. 19, the liquid sending portion 11, the second container 13, and the sensor 12 may be provided so as to be used in common among a plurality of the first containers 14a and a plurality of the sample processing chips 200. In this case, it is configured such that the first container 14a to which the second liquid 22 is sent can be selected through opening/closing of valves 16a.

In addition to these, the liquid sending apparatus 100 can include a monitor 17, an input unit 18, a reading unit 19, and the like. The controller 10 causes the monitor 17 to display a predetermined display screen in accordance with the operation of the liquid sending apparatus 100. The liquid sending apparatus 100 may be connected to an external computer (not shown), and may cause a screen to be displayed on the monitor of the computer. The input unit 18 is composed of, for example, a keyboard, a mouse, and the like, and has a function of receiving input of information. The reading unit 19 is composed of, for example, a code reader for bar code, two-dimensional code, or the like, or a tag reader for RFID tag or the like, and has a function of reading information given to the sample processing chip 200. The reading unit 19 can also read information of a sample container (not shown) containing the first liquid 21, or the like.

Figure 20:
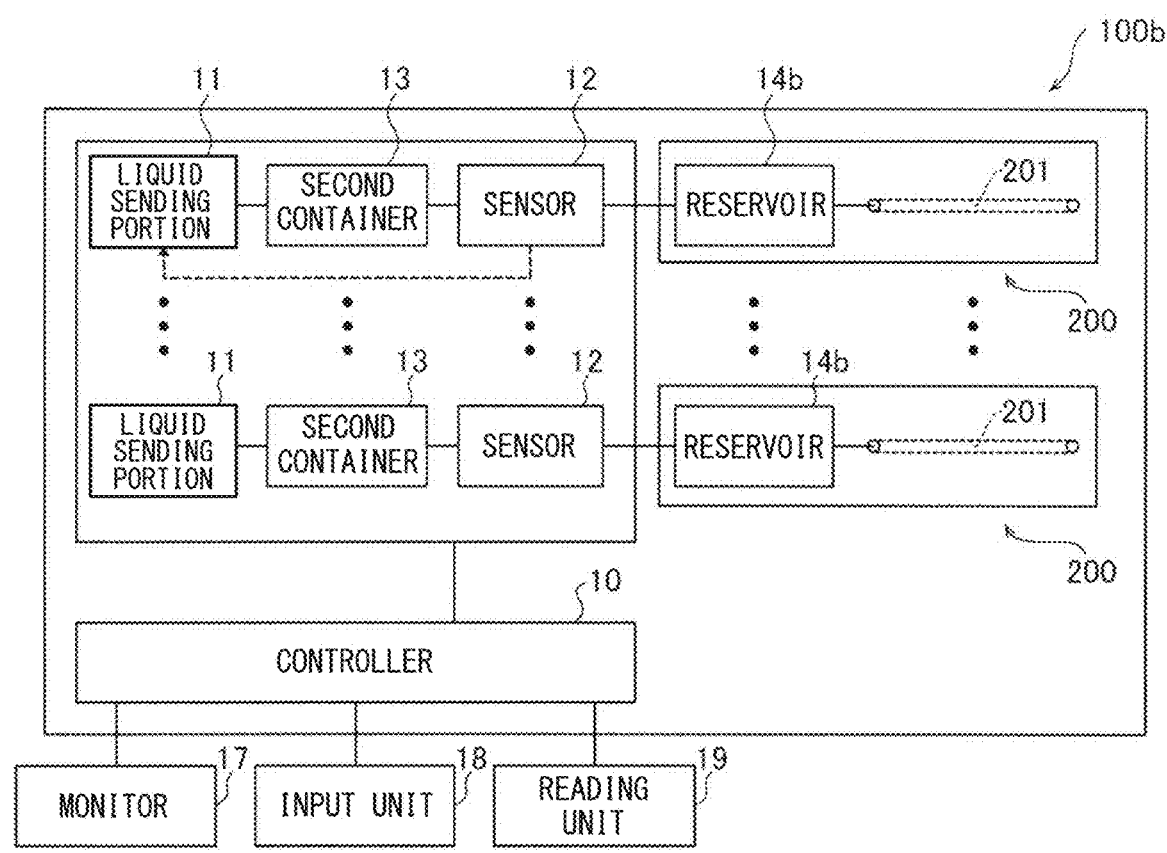
FIG. 20 is a block diagram showing still another configuration example of the liquid sending apparatus.

A liquid sending apparatus 100b of still another example shown in FIG. 20 includes the reservoir 14b containing the first liquid 21, instead of the first container 14a. The reservoir 14b is connected to the inlet of the flow path in the sample processing chip 200. The reservoir 14b may be integrally provided to the sample processing chip 200. The reservoir 14b is provided as a tubular liquid reservoir on the port through which the first liquid 21 is injected.

Each liquid sending portion 11 is configured to cause the second liquid 22 to flow into the reservoir 14b, thereby introducing the first liquid 21 into the flow path 201 in the sample processing chip 200 through the inlet of the flow path 201. Accordingly, the first liquid 21 can be pushed in the reservoir 14b by means of the second liquid 22, to be sent out of the reservoir 14b. Thus, the first liquid 21 can be accurately sent into the flow path 201 in the sample processing chip 200.

The first liquid 21 is a solution that contains a sample, for example. A plurality of the sample processing chips 200 each provided with the reservoir 14b containing the first liquid 21 are provided. Accordingly, for each sample, the sample processing chip 200 provided with the reservoir 14b can be prepared to perform processing. Thus, a plurality of samples can be efficiently processed while different samples are inhibited from being mixed with one another. The liquid sending portion 11, the second container 13, the sensor 12, and the reservoir 14b are provided for each of the plurality of the sample processing chips 200. It should be noted that the liquid sending portion 11, the second container 13, and the sensor 12 may be provided so as to be used in common among a plurality of the reservoirs 14b and a plurality of the sample processing chips 200.

Figure 21:
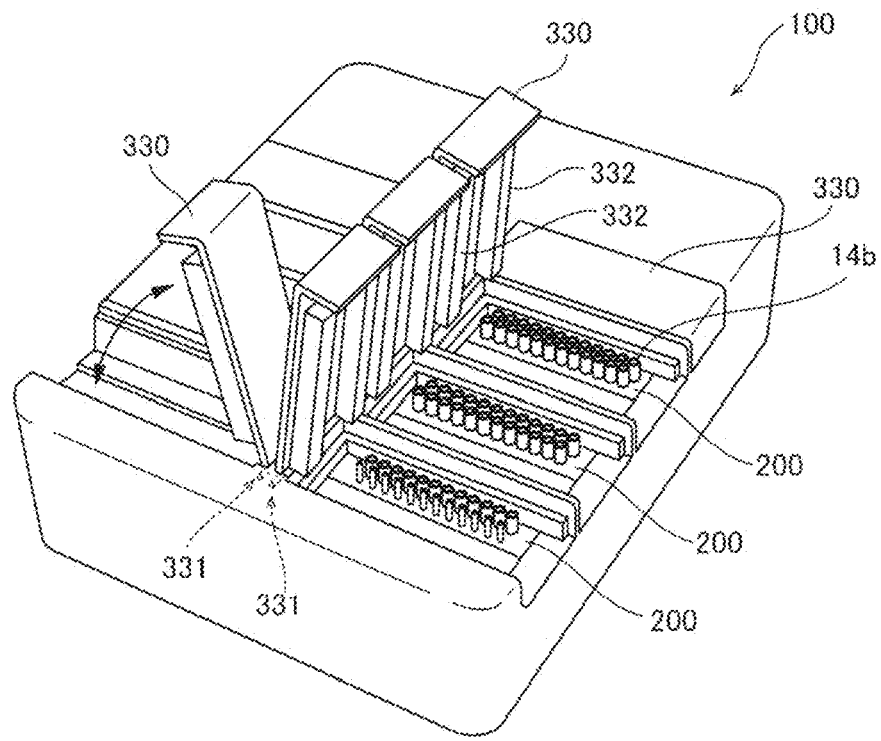
FIG. 21 is a perspective view showing a configuration example of the liquid sending apparatus.

FIG. 21 is a schematic diagram showing the external appearance of the liquid sending apparatus 100. In FIG. 21, the liquid sending apparatus 100 includes: setting portions on each of which a sample processing chip 200 is set; and a cover 330 corresponding to each setting portion. The liquid sending apparatus 100 includes: an apparatus body; and the covers 330 connected to the apparatus body. The setting portions are disposed on the upper face of the apparatus body in a box shape.

Each cover 330 includes a hinge 331 and a connector 332. That is, the connector 332 includes a connection hole to the reservoir 14b of the sample processing chip 200. When each connector 332 is connected to the reservoir 14b of the corresponding sample processing chip 200 set on the corresponding setting portion, sending of the second liquid 22 to the reservoir 14b is enabled.

Accordingly, with the sample processing chip 200 being set in the apparatus and by means of the connector 332 at the cover 330 side, the connection between the sample processing chip 200 and the liquid sending apparatus 100 can be easily and reliably established. Since the sample processing chip 200 is set in the apparatus, the liquid sending tube, the pressure passage, and the like for sending liquid can be inhibited from becoming unnecessarily long, whereby quick response of the liquid sending process can be realized and the controllability can be enhanced. The connector 332 may be detachably mounted to the cover 330, or may be fixed to the cover 330. A plurality of the connectors 332 may be provided.

Although not shown in detail in FIG. 21, the sample processing chip 200 provided with a plurality of channels is set in the setting portion. The connector 332 is provided at the lower face of the cover 330. The connector 332 is formed as a manifold capable of being connected at once to the reservoir 14b provided to each of the unit flow path structures of the plurality of channels. That is, the connector 332 integrally includes connection holes to the plurality of the reservoirs 14b which are provided by the number of the channels in the sample processing chip 200. When the cover 330 is closed, the connector 332 and the reservoir 14b provided to each of the unit flow path structures of the plurality of channels are connected to each other at once.

Thus, in the example shown in FIG. 21, the cover 330 is configured to be able to open/close with respect to the setting portion, and by the cover 330 being closed with respect to the setting portion, the connector 332 is connected to each of the reservoirs 14b. In the example shown in FIG. 21, the cover 330 is connected to the apparatus body by means of the hinge 331, and is opened/closed by being rotated about the hinge 331.

(Supply of First Liquid)

The liquid to be used as the first liquid 21 is not limited in particular as long as the liquid is the one that is used in sample processing performed in the sample processing chip 200. The first liquid 21 is preferably supplied to the reservoir 14b in the sample processing chip 200.

Figure 22:
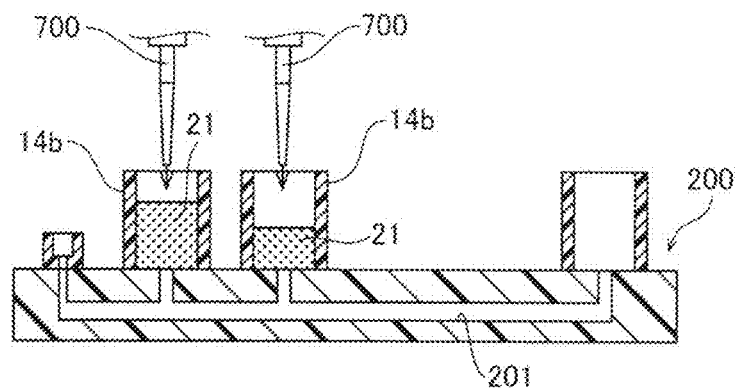
FIG. 22 is a diagram showing an injection example of the first liquid.

For example, in the example shown in FIG. 22, the first liquid 21 is supplied by each injection tool 700 to the corresponding reservoir 14b of the sample processing chip 200. That is, as shown in FIG. 22, before the first liquid 21 is sent, the first liquid 21 is injected by the injection tool 700 into the reservoir 14b. The injection tool 700 is a pipette, a syringe, a dispenser device, or the like, for example. Accordingly, similarly to the case of the injection of liquid into a general well plate, the operator can easily inject the first liquid 21 into the reservoir 14b by use of the injection tool 700 such as a pipette. Thus, convenience for the operator is improved. At this time, preferably, the first liquid 21 is injected such that no air is contained in an upper portion of the reservoir 14b. Accordingly, during liquid sending, trapping of an air layer between the first liquid 21 and the second liquid 22 can be inhibited. It should be noted that the injection of the first liquid 21 may be performed after or before the sample processing chip 200 is set at the setting portion of the liquid sending apparatus 100.

(Connection Structure to Sample Processing Chip)

Figure 23:
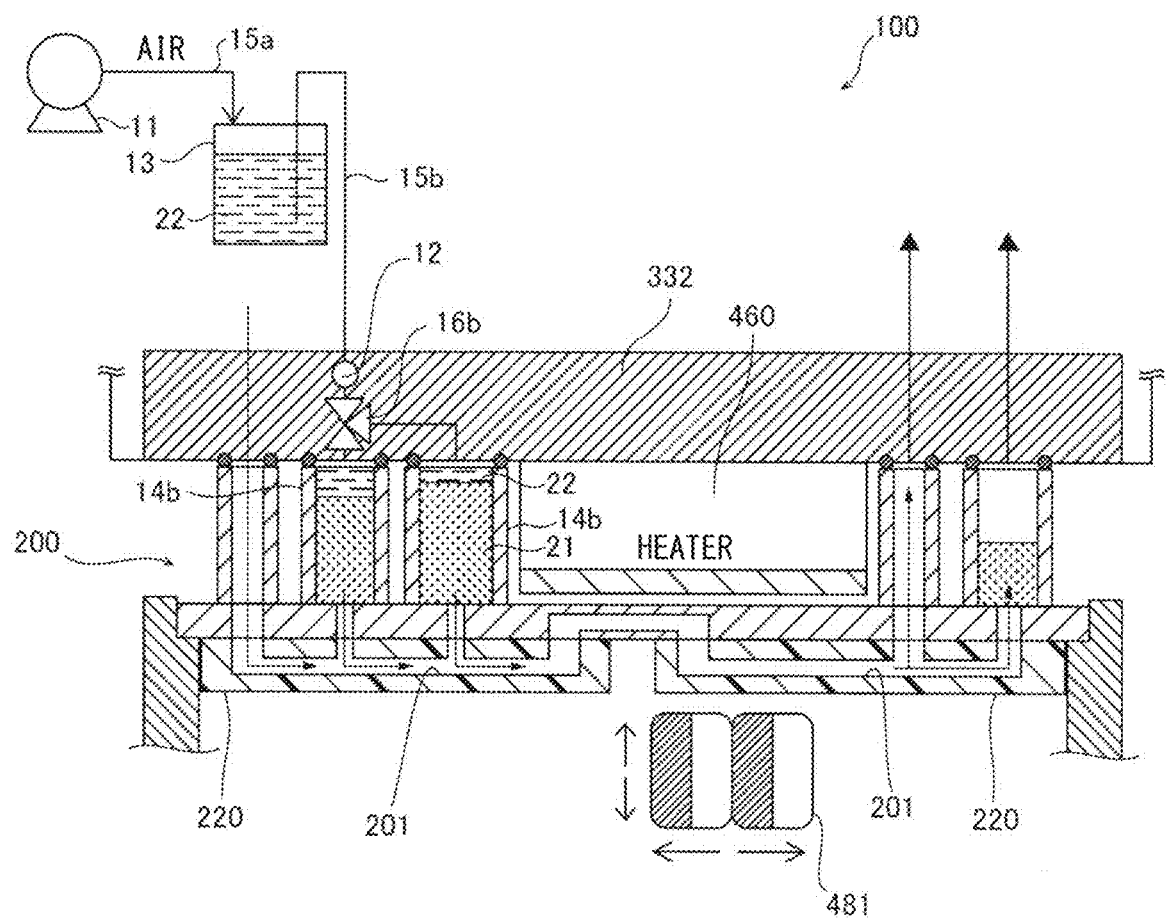
FIG. 23 is a longitudinal cross-sectional view showing a configuration example in which the liquid sending apparatus and the sample processing chip are connected to each other.

FIG. 23 shows the sample processing chip 200 set at a setting portion, and the connector 332 provided to the cover 330 that corresponds to the setting portion. FIG. 23 shows one unit flow path structure in the sample processing chip 200, for example. The manifold-type connector 332 is provided with a plurality of liquid sending tubes and a plurality of pressure passages. In a state where the cover 330 is closed, the liquid sending tubes and the pressure passages, and the reservoirs 14b in the sample processing chip 200 are connected to each another at once, through the connector 332.

In the example shown in FIG. 23, the connector 332 is provided with a valve 16b and a sensor 12. It should be noted that the valve 16b and the sensor 12 may be provided separately from the connector 332.

In FIG. 23, the space between the connector 332 and the upper face of each reservoir 14b is sealed by a sealing member such as an O ring or a gasket, for example.

(Configuration Example of Sensor)

Figure 24:
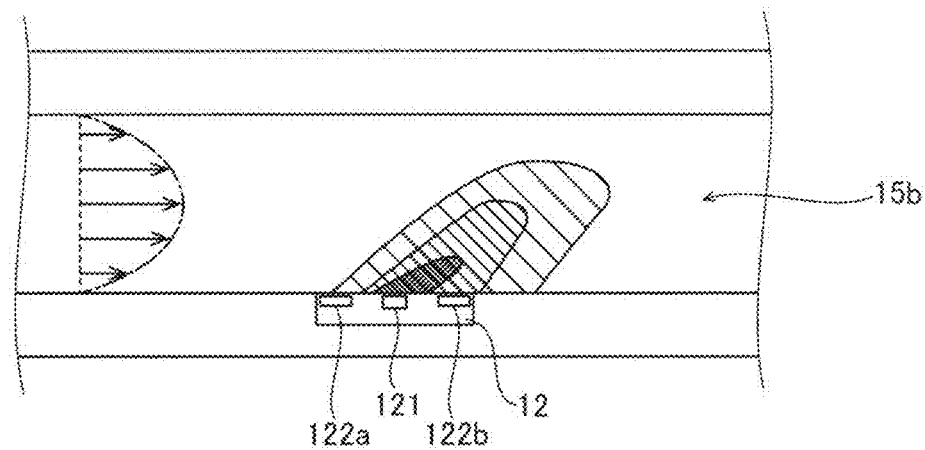
FIG. 24 is a cross-sectional view showing a configuration example of a sensor.

FIG. 24 shows a configuration example of the sensor 12 which measures the flow including at least one of the flow rate, the flow velocity, and the pressure of the second liquid 22.

In the example shown in FIG. 24, the sensor 12 includes a thermal flowmeter, for example. The sensor 12 is embedded in the flow path 15b for the second liquid 22. The sensor 12 includes a heat source 121 and heat measuring portions 122a and 122b. The heat measuring portions 122a and 122b are arranged along the liquid flowing direction so as to sandwich the heat source 121. That is, the heat measuring portions 122a and 122b are arranged such that one of the heat measuring portions 122a and 122b is disposed at the upstream side with respect to the heat source 121, and the other of the heat measuring portions 122a and 122b is disposed at the downstream side with respect to the heat source 121. The sensor 12 measures the flow rate of the liquid flowing in the flow path 15b on the basis of the difference in temperatures measured by the heat measuring portions 122a and 122b. That is, since the liquid flows from upstream to downstream, the heat generated by the heat source 121 also moves along the flow. Thus, heat is difficult to be conducted at upstream, but is easy to be conducted at downstream. In addition, the greater the flow rate is, the greater the difference between the temperature at upstream and the temperature at downstream becomes. The liquid flowing in the flow path 15b is preferably in the form of a laminar flow. The sensor 12 may be a differential pressure type flowmeter, instead of the thermal flowmeter. The sensor 12 may be a flowmeter that uses sound wave or laser. The sensor 12 may be an electromagnetic type flowmeter. The measured flow rate can be mutually converted between a volume flow rate and a mass flow rate by use of density, or can be converted into a flow velocity by use of the cross-sectional area of the flow path. The measured flow rate also can be converted into a pressure by use of the Bernoulli equation or the like.

(Configuration Example of Sample Holding Portion)

Figure 25:
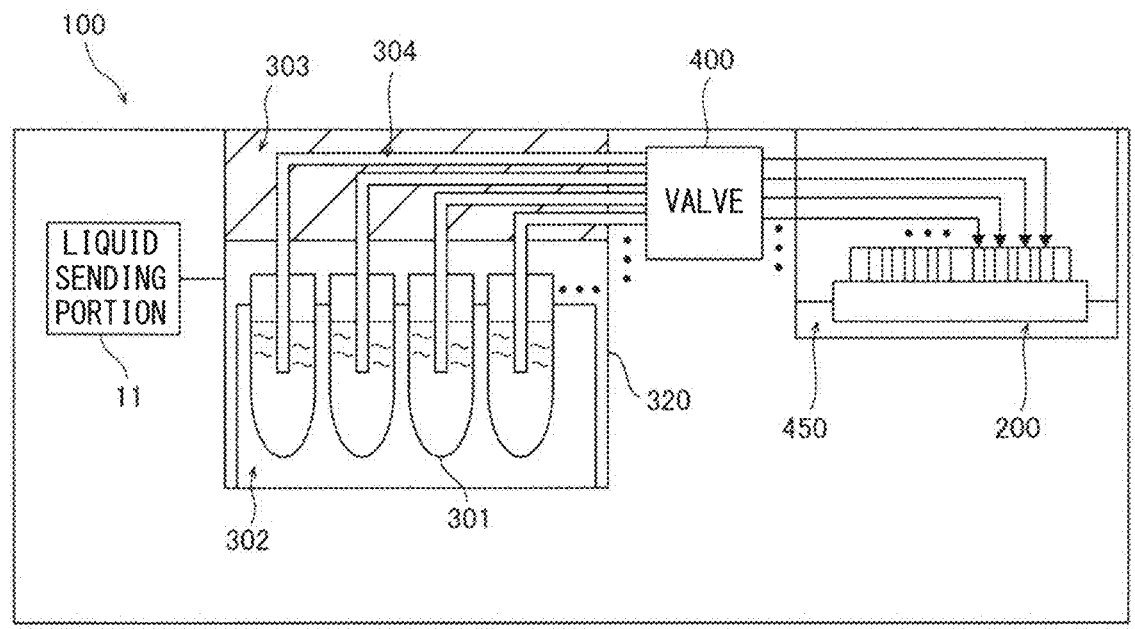
FIG. 25 is a longitudinal cross-sectional view showing a configuration example of a sample holding portion.

FIG. 25 shows a configuration example of a sample holding portion 320.

Each liquid container 301 for a sample, a reagent, or the like is disposed in a container setting portion 302 in the sample holding portion 320. A plurality of the container setting portions 302 may be provided, or a single container setting portion 302 may be provided, as shown in FIG. 25.

Liquid sending tubes 304 provided at the cover 303 of the container setting portion 302 are connected to the sample processing chip 200 through a valve 400. When the pressure in the sample holding portion 320 is increased and the valve 400 is opened, the liquid in each liquid container 301 is supplied to the sample processing chip 200 side.

(Configuration Example of Valve)

The valve 400 functions as a valve for introducing fluid into the flow path 201. A plurality of the valves 400 may be provided for each flow path.

Figure 26:
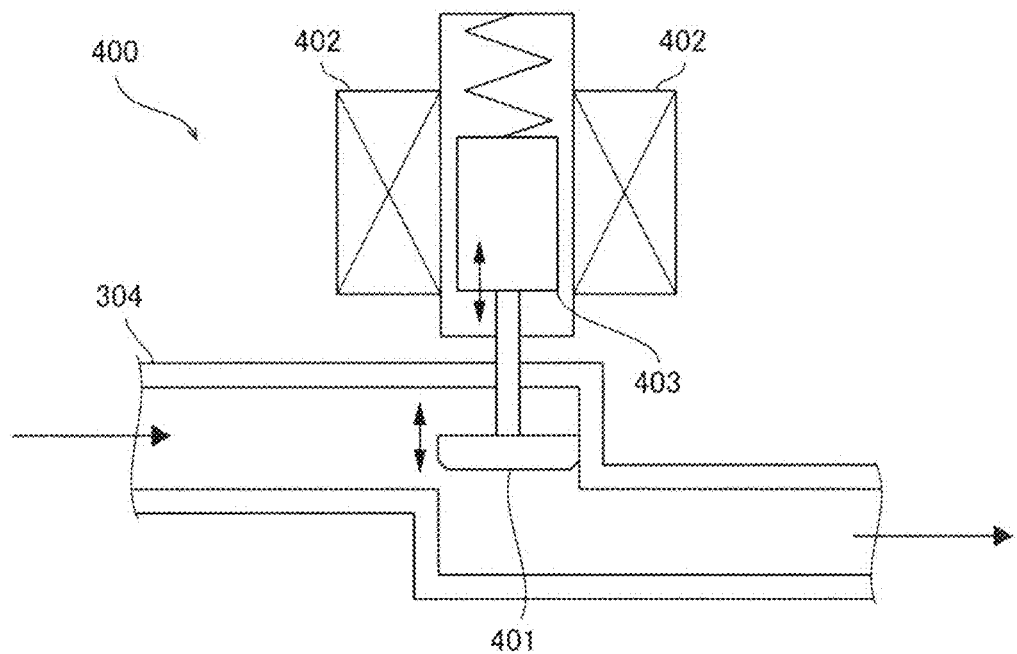
FIG. 26 is a cross-sectional view showing a configuration example of a valve.

FIG. 26 shows a configuration example of the valve 400. The valve 400 is an electromagnetic valve, for example. The valve 400 includes a valve 401, a coil 402, and a plunger 403. The valve 401 opens/closes the liquid sending tube 304. A plurality of the valves 400 are provided in the liquid sending apparatus 100. The controller 10 can control opening/closing of each valve 400 individually.

(Configuration Example of Cover of Setting Portion of Sample Processing Chip)

Figure 27:
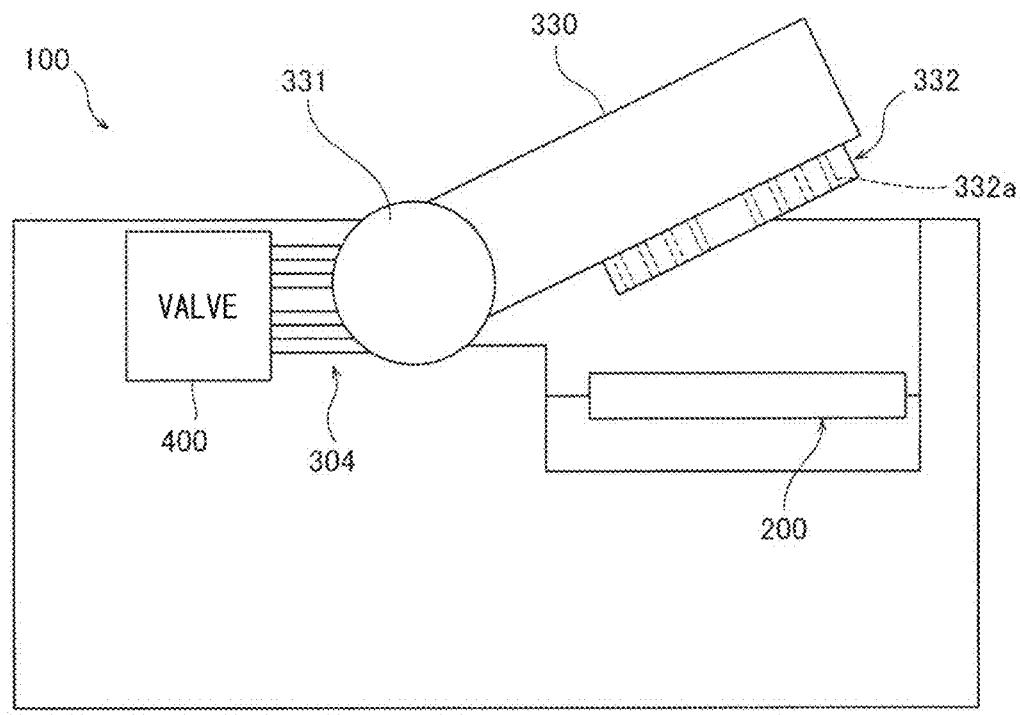
FIG. 27 is a longitudinal cross-sectional view showing a configuration example of a setting portion.

The setting portion for the sample processing chip 200 may be provided with a cover 330 that corresponds to the setting portion. FIG. 27 shows a configuration example of the cover 330 of the setting portion. The cover 330 is provided so as to cover the sample processing chip 200 set at the setting portion.

The cover 330 is connected to the liquid sending apparatus 100 by means of the hinge 331. The cover 330 is opened/closed through rotation of the hinge 331. The cover 330 may include the connector 332. When the cover 330 of the setting portion is simply closed, the sample processing chip 200 set at the setting portion and the connector 332 are connected to each other. The cover 330 may be detachable with respect to the liquid sending apparatus 100. In this case, the hinge 331 may not be provided.

(Configuration Example of Connector)

Figure 28:
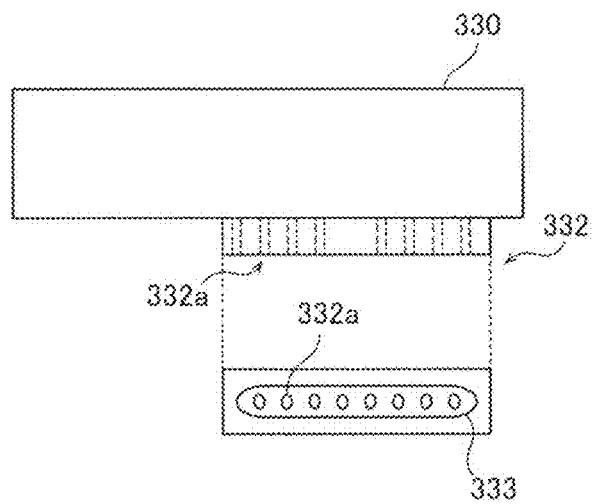
FIG. 28 is a diagram showing a configuration example of a connector.

FIG. 28 shows a configuration example of the connector 332. The connector 332 is provided to the cover 330. The connector 332 has holes 332a for providing access to the base plate flow paths 211 in the base plate 210. The connector 332 is set at a position that corresponds to the base plate flow paths 211 in the base plate 210. The connector 332 may be set only at a position that corresponds to a desired base plate flow path 211. The connector 332 may be formed as a manifold in which a plurality of the liquid sending tubes 304 are formed. In this case, when the cover 330 is closed, the liquid sending tubes 304 and all the ports in the sample processing chip 200 are connected to each other at once through the connector 332.

The liquid such as a sample or a reagent is injected into the sample processing chip 200 from a liquid sending tube 304 through a hole 332a. The liquid flowing in the sample processing chip 200 is collected from the sample processing chip 200 through a hole 332a. The connector 332 has a sealing member for inhibiting liquid leakage and foreign matter contamination, such as a gasket 333 at the contact face with the sample processing chip 200.

(Configuration Example of Fixing Tool)

Figure 29:
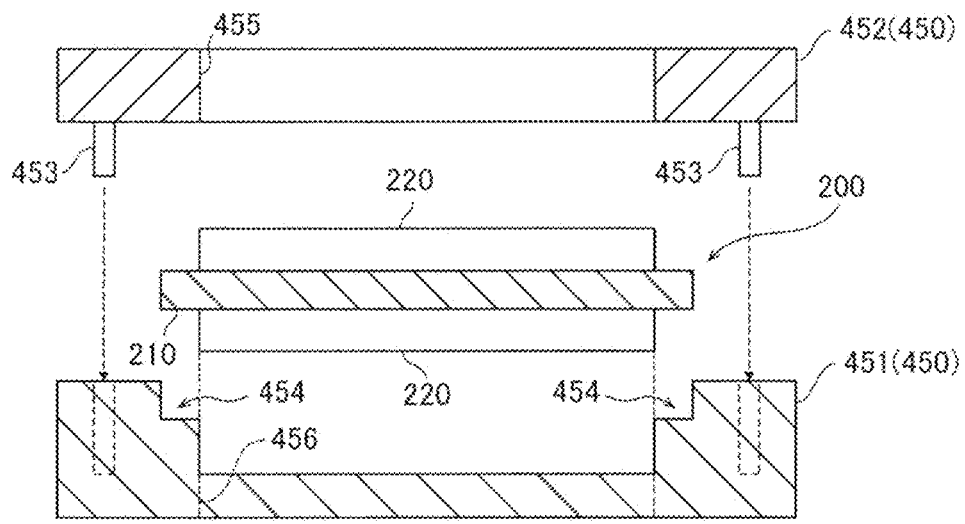
FIG. 29 is an exploded view showing a configuration example of a fixing tool.
Figure 30:
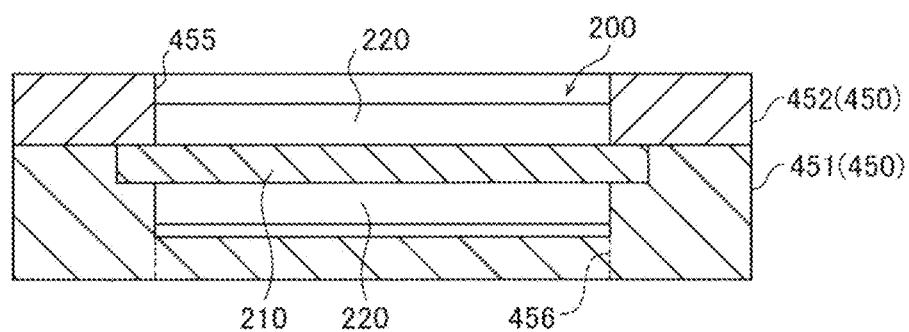
FIG. 30 is a diagram showing the fixing tool in a state where the sample processing chip is fixed.

FIG. 29 to FIG. 31 show an example of a fixing tool 450 to be used for setting the sample processing chip 200 to the liquid sending apparatus 100.

As shown in FIG. 29, the sample processing chip 200 is fixed by fixing tools 451 and 452, for example. The fixing tools 451 and 452 are fixed by a fitting member 453. The relative position between the sample processing chip 200 and the fixing tools 451 and 452 is determined by the positioning portion 454. The sample processing chip 200 is fixed by the fixing tools as shown in FIG. 30.

Figure 31A:
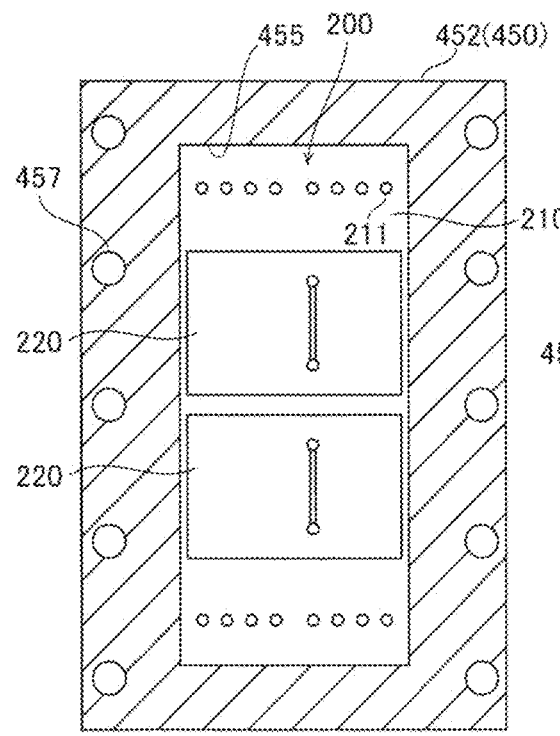
FIG. 31A is a top view of the fixing tool shown in FIG. 30.
Figure 31B:
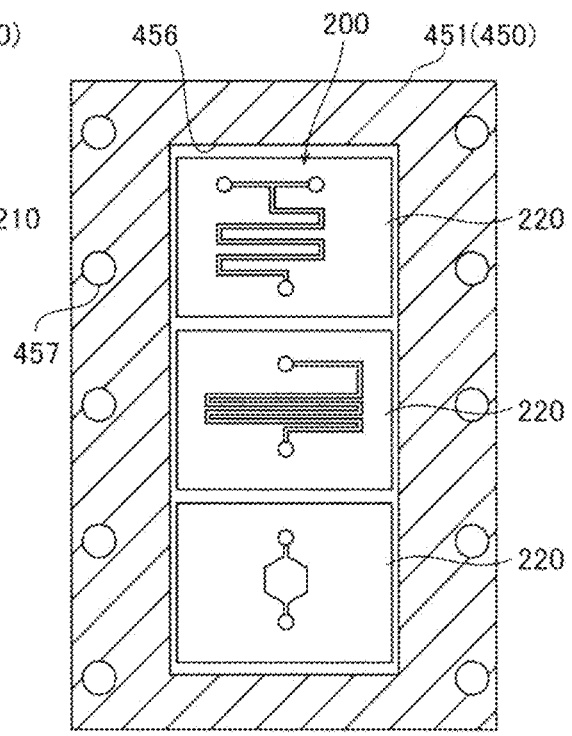
FIG. 31B is a bottom view of the fixing tool shown in FIG. 30.

As shown in FIG. 31A, the fixing tool 452 has an opening 455, which is a through-hole, at a place that corresponds to the base plate 210. The connector 332 and the like of the liquid sending apparatus 100 can access the base plate 210 from above through the opening 455. As shown in FIG. 31B, the fixing tool 451 has an opening 456, which is a through-hole, at a place that corresponds to the base plate 210 and the fluid modules 220. The base plate 210 and the fluid modules 220 can be accessed from below through the opening 456.

The fixing tool 452 may be fixed to the cover 330 of the setting portion. The fixing tools 451 and 452 may have mounting holes 457 for arranging various types of processing units provided in the liquid sending apparatus 100.

(Setting Example of Various Types of Processing Units)

Figure 32A:
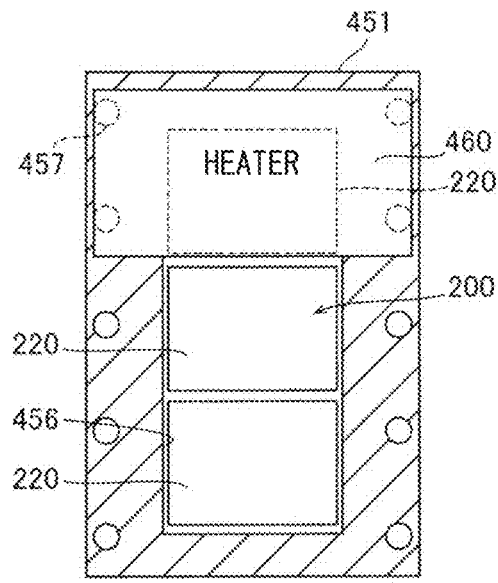
FIG. 32A is a bottom view showing an arrangement example of a heater unit.
Figure 32B:
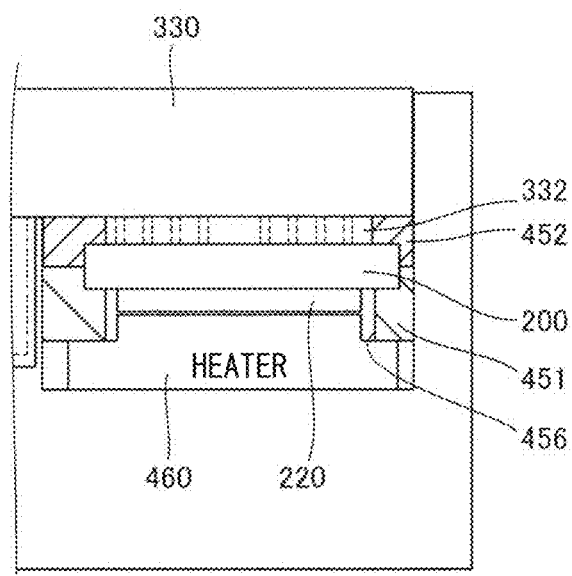
FIG. 32B is a schematic cross-sectional view showing an arrangement example of the heater unit in a setting portion.
Figure 33A:
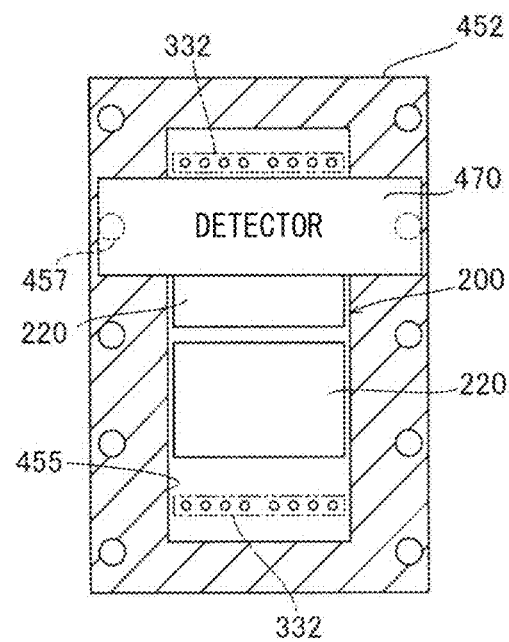
FIG. 33A is a top view showing an arrangement example of a detection unit.
Figure 33B:
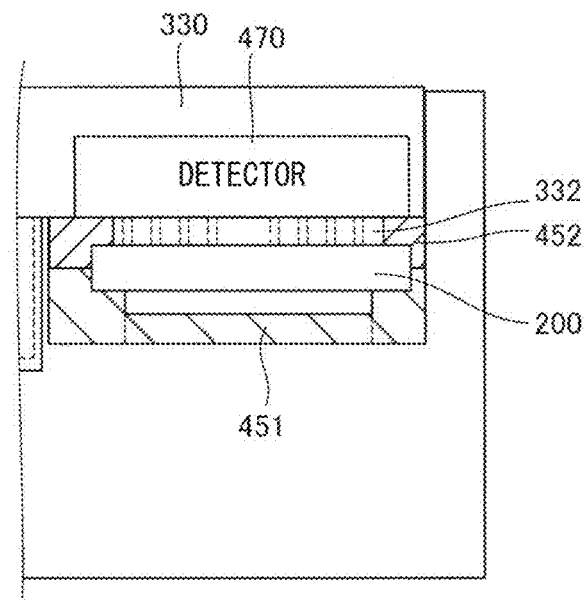
FIG. 33B is a schematic cross-sectional view showing an arrangement example of the detection unit in a setting portion.
Figure 34A:
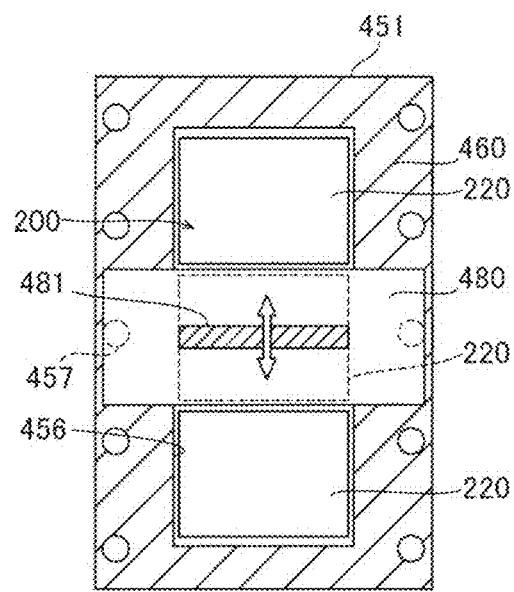
FIG. 34A is a bottom view showing an arrangement example of a magnet unit.
Figure 34B:
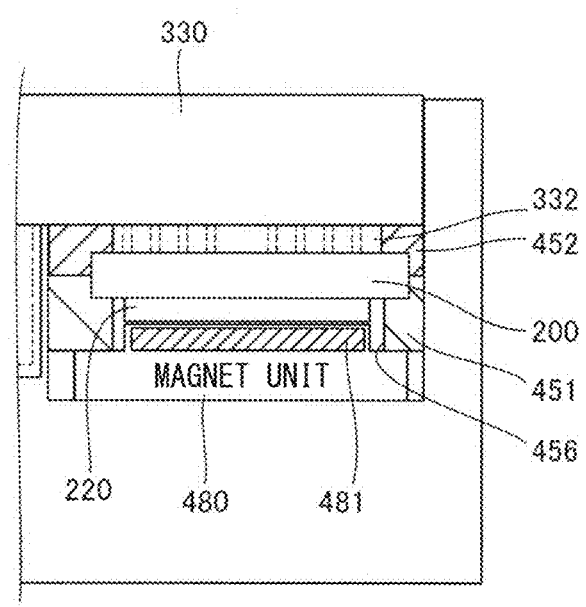
FIG. 34B is a schematic cross-sectional view showing an arrangement example of the magnet unit in a setting portion.

FIG. 32 to FIG. 34 show setting examples of processing units to be used in various types of process steps in the liquid sending apparatus 100.

For example, a heater unit (heater 460) for heating the liquid in the fluid module 220, a magnet unit 480 (see FIG. 34) for causing magnetic force to act on the liquid in the fluid module 220, a cooling unit (not shown) for cooling the liquid in the fluid module 220, a detection unit (detector 470, see FIG. 33) for detecting a target component in the sample processing chip 200, a camera unit (not shown) for taking images of the flow of the liquid in the fluid module 220, and the like are mounted to the fixing tool 451 or 452 through the mounting holes 457. The connector 332 may be mounted to the fixing tool 451 or 452. The units may be a composite unit having a plurality of functions among these functions. For example, a unit may be used that has a function of heating liquid and a function of causing magnetic force to act on liquid.

(Heater Unit)

FIG. 32 shows an arrangement example of the heater 460 in the liquid sending apparatus 100.

The heater 460 adjusts the temperature of the sample processing chip 200. For example, the heater 460 heats the sample processing chip 200 in order to amplify DNA by PCR in the fluid module 220.

The heater 460 is provided to the setting portion. For example, the heater 460 is mounted to the fixing tool 451 at the lower face of the sample processing chip 200. The heater 460 adjusts the temperature of the sample processing chip 200 from the lower face side of the sample processing chip 200 set at the setting portion. The heater 460 may be mounted to the cover 330 or the fixing tool 452 at the upper face side. The heater 460 is disposed at a position that corresponds to a fluid module 220 to be subjected to temperature adjustment. The heater 460 may be movable.

(Detection Unit)

FIG. 33 shows a configuration example of the detector 470 of the liquid sending apparatus 100.

The detector 470 detects fluorescence of a labeled substance bound to the target component, for example. The detector 470 is a photomultiplier, for example. The detector 470 is mounted to the fixing tool 452 at the upper face side of the sample processing chip 200. The detector 470 may be provided to the cover 330. The detector 470 detects fluorescence through the connector 332 connected to the sample processing chip 200. The detector 470 may be provided to the liquid sending apparatus 100, or the fixing tool 451 at the lower face side of the sample processing chip 200. In this case, the detector 470 detects fluorescence from the lower face side of the sample processing chip 200.

(Magnet Unit)

FIG. 34 shows a configuration example of the magnet unit 480 to be used in control of magnetic particles contained in the liquid in the sample processing chip 200.

The magnet unit 480 is mounted to the fixing tool 451 at the lower face side of the sample processing chip 200, for example. The magnet unit 480 may be provided to the liquid sending apparatus 100. The magnet unit 480 may be mounted to the cover 330 or the fixing tool 452 at the upper face side. The magnet unit 480 includes a magnet 481. The magnet 481 causes magnetic force to act on the magnetic particles contained in the liquid in the sample processing chip 200. The magnet unit 480 can move the magnet 481 in the longitudinal direction of the sample processing chip 200, for example.

Although not shown, the same applies to the camera unit and the cooling unit.

[Example of Assay that Uses Sample Processing Chip]

Next, a specific example of assay that uses the sample processing chip 200 is described.

(Emulsion PCR Assay)

An example is described in which an emulsion PCR assay is performed by use of the sample processing chip 200 described above.

Figure 35:
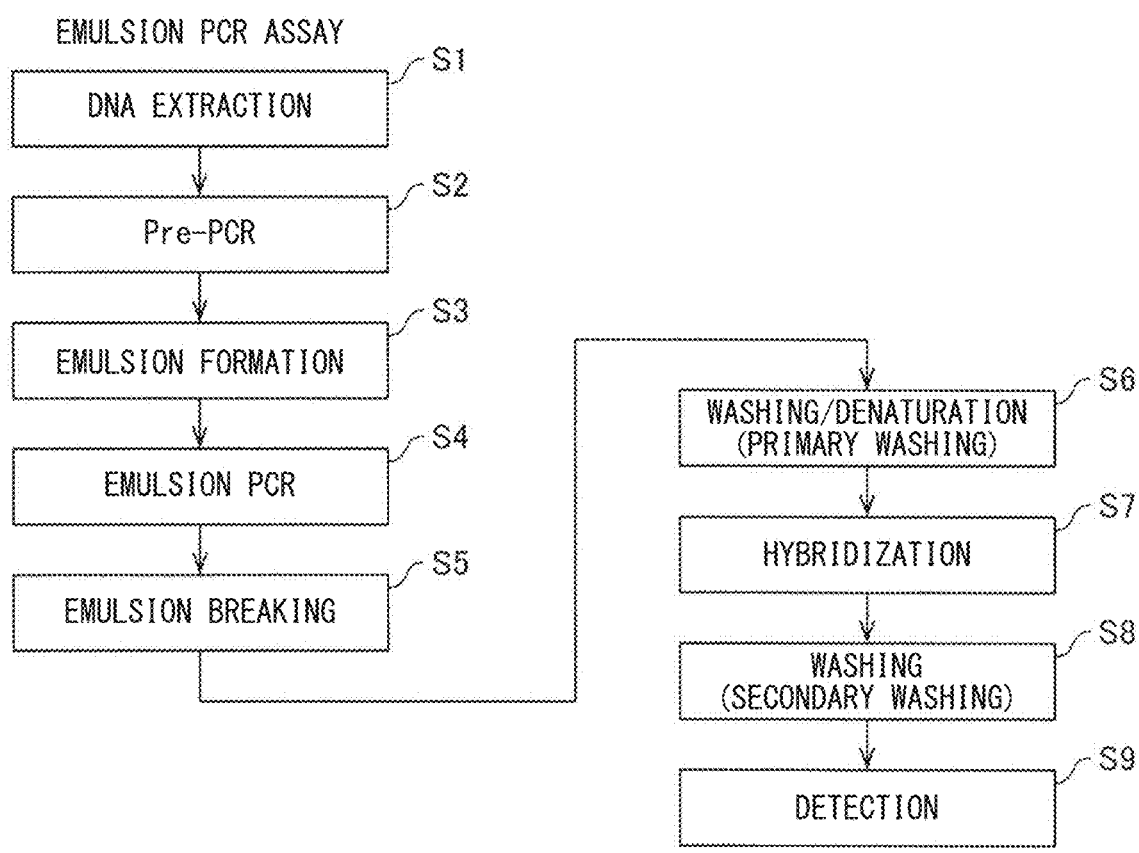
FIG. 35 is a flow chart showing one example of an emulsion PCR assay.

FIG. 35 shows an example of the flow of an emulsion PCR assay.

Figure 36:
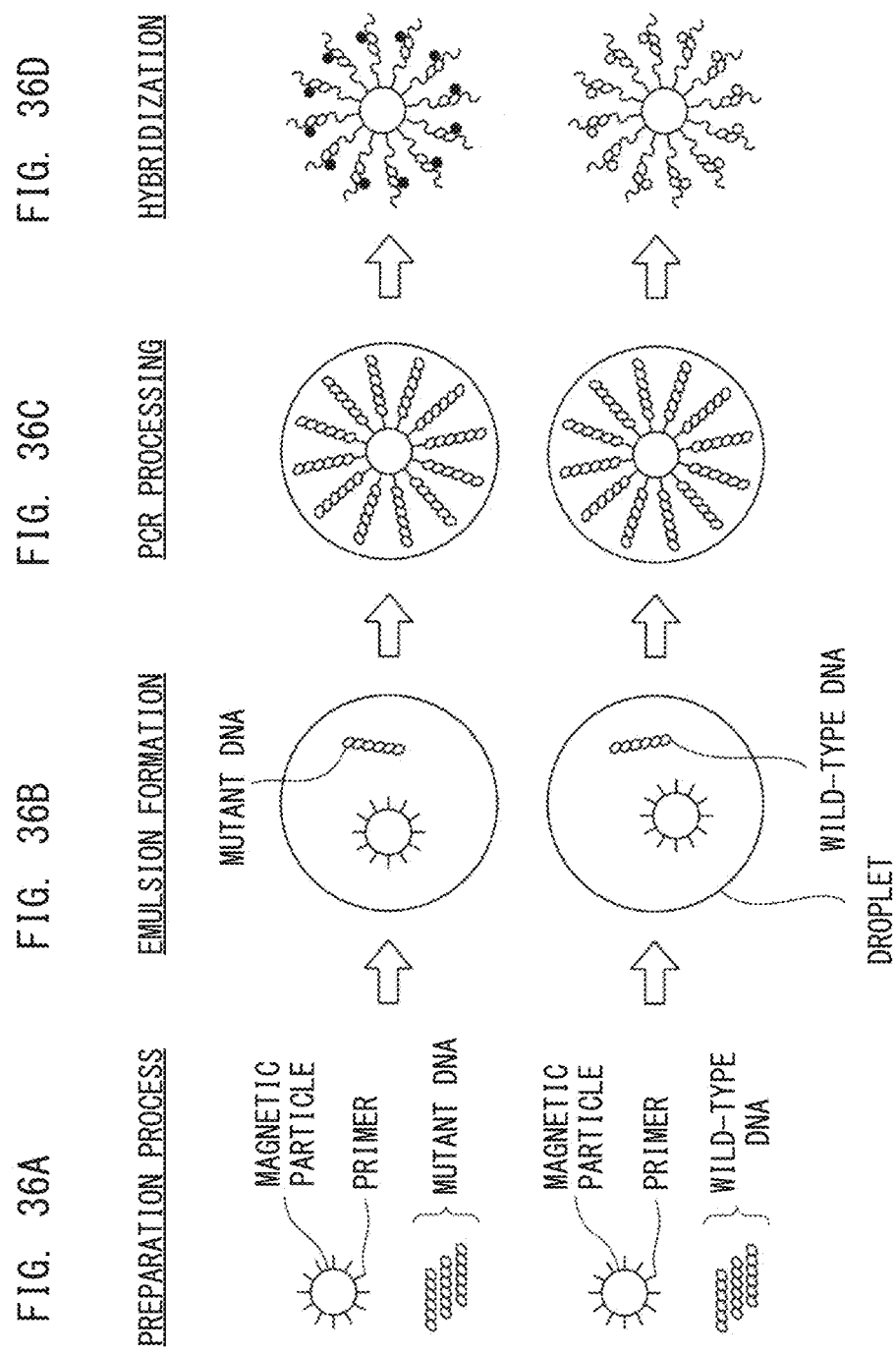
FIG. 36A is a diagram describing how reaction in the emulsion PCR assay proceeds.
FIG. 36B is a diagram describing how reaction in the emulsion PCR assay proceeds.
FIG. 36C is a diagram describing how reaction in the emulsion PCR assay proceeds.
FIG. 36D is a diagram describing how reaction in the emulsion PCR assay proceeds.

FIG. 36 is a diagram describing how the reaction proceeds in the emulsion PCR assay.

In step S1, DNA is extracted from a specimen such as blood, through pretreatment (see FIG. 36A). For the pretreatment, a dedicated nucleic acid extracting device may be used, or a pretreatment mechanism may be provided to the liquid sending apparatus 100.

In step S2, the extracted DNA is amplified by Pre-PCR processing (see FIG. 36A). The Pre-PCR processing is a process of preliminarily amplifying DNA contained in the extract obtained through pretreatment, to an extent that allows a successive emulsion forming process to be performed. In the Pre-PCR processing, the extracted DNA, and a PCR amplification reagent which contains a primer and a polymerase are mixed together, and DNA in the mixture is amplified through temperature control by a thermal cycler. The thermal cycler performs a thermal cycle process of repeating, a plurality of times, one cycle in which the temperature of the mixture is changed to a plurality of different temperatures.

Step S3 is an emulsion forming step of forming droplets in a dispersion medium, each droplet containing a mixture of: nucleic acid (DNA) serving as a target component; a reagent for amplification reaction of the nucleic acid; and a carrier for the nucleic acid. The reagent for amplification reaction of the nucleic acid contains substances necessary for PCR such as DNA polymerase. In step S3, an emulsion which encapsulates DNA and the reagent that contains magnetic particles, polymerase, and the like is formed (see FIG. 36B). An emulsion is a disperse system solution in which a liquid that does not mix with a dispersion medium is dispersed in the dispersion medium. That is, in step S3, droplets which each contain a mixture of: DNA; and a reagent that contains magnetic particles, polymerase, and the like are formed, and a large number of the droplets are dispersed in a dispersion medium. To the surface of the magnetic particle encapsulated in a droplet, the primer for nucleic acid amplification is attached. Each droplet is formed so as to contain about one magnetic particle and one target DNA molecule. The dispersion medium has immiscibility with the mixture. In this example, the mixture is water-based, and the dispersion medium is oil-based. The dispersion medium is an oil, for example.

Step S4 is an emulsion PCR step of amplifying the nucleic acid (DNA) in each droplet formed in the emulsion forming step. In step S4, through temperature control by the thermal cycler, DNA binds to the primer on the magnetic particle in each droplet of the emulsion, to be amplified (emulsion PCR) (see FIG. 36C). Accordingly, the target DNA molecule is amplified in the individual droplets. That is, in each droplet, an amplification product of the nucleic acid is formed. The amplified nucleic acid binds to the carrier through the primer in the droplet.

Step S5 is an emulsion breaking step of breaking each droplet containing the carrier (magnetic particle) which carries the amplification product of the nucleic acid (DNA) obtained through the emulsion PCR step. That is, after DNA is amplified on the magnetic particle in step S4, the emulsion is broken (demulsified) and the magnetic particles including the amplified DNA are taken out of the droplets (emulsion breaking) in step S5. For breaking the emulsion, one or a plurality of types of emulsion breaking reagents including alcohol, surfactant, and the like are used.

Step S6 is a washing step of collecting the carrier (magnetic particles) taken out of the droplets broken in the emulsion breaking step. In step S6, the magnetic particles taken out of the droplets are washed in a BF separation step (primary washing). The BF separation step is a process step in which the magnetic particles including the amplified DNA are caused to pass through a washing liquid in a state where the magnetic particles are collected by magnetic force, such that unnecessary substances attached to the magnetic particles are removed. In the primary washing step, a washing liquid that contains alcohol is used, for example. The alcohol removes the oil film on the magnetic particles, and denatures the amplified double-stranded DNA into single strands.

Step S7 is a hybridization step of causing the amplification product on the collected carrier (magnetic particles) through the washing step to react with a labeled substance. After the washing, in step S7, the DNA denatured into single strands on the magnetic particle is hybridized with the labeled substance for detection (hybridization) (see FIG. 36D). The labeled substance contains a substance that emits fluorescence, for example. The labeled substance is designed so as to specifically bind to the detection target DNA.

In step S8, the magnetic particle bound to the labeled substance is washed in another BF separation step (secondary washing). The secondary BF separation step is performed through a process similar to that of the primary BF separation step. In the secondary washing step, PBS (phosphate buffered saline) is used as the washing liquid, for example. PBS removes unreacted labeled substance that did not bind to DNA (including labeled substance non-specifically attached to the magnetic particles).

In step S9, DNA is detected via the hybridized labeled substance. DNA is detected by a flow cytometer, for example. In the flow cytometer, the magnetic particle including DNA bound to the labeled substance is caused to flow in a flow cell, and is irradiated with laser light. Fluorescence emitted from the labeled substance irradiated with laser light is detected.

DNA may be detected through image processing. For example, the magnetic particles including DNA bound to the labeled substance are dispersed on a flat slide, and an image of the dispersed magnetic particles is taken by a camera unit. On the basis of the taken image, the number of the magnetic particles emitting fluorescence is counted.

[Example of Sample Processing]

In the following, an assay example of sample processing which uses various types of the sample processing chips 200 is described. In the description below, transport of fluids such as a sample, various types of reagents, and the first liquid 21 to the sample processing chip 200, and the flow of such fluids in the sample processing chip 200 are controlled by the controller 10 of the liquid sending apparatus 100 in which the sample processing chip 200 is set.

(Emulsion PCR Assay)

Figure 37:
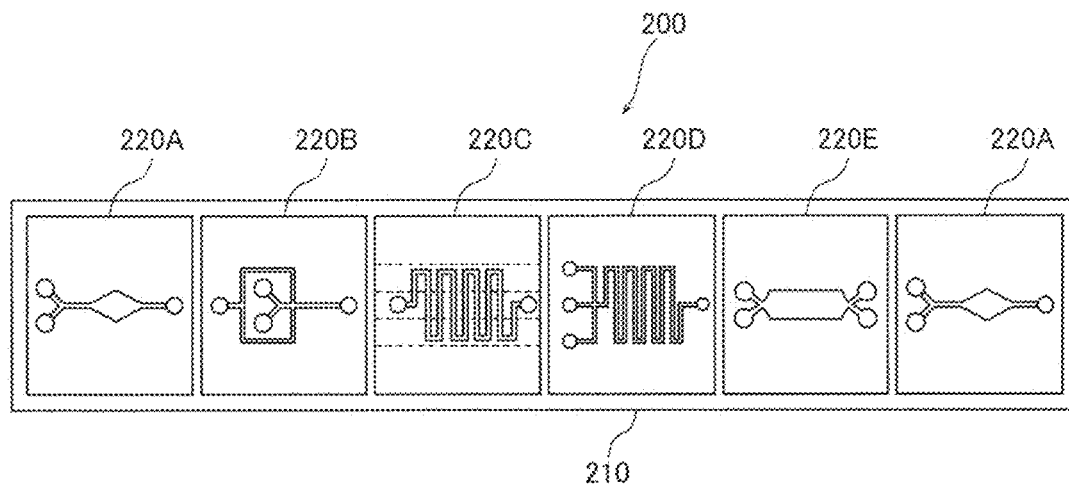
FIG. 37 is a diagram showing a configuration example of a sample processing chip to be used in the emulsion PCR assay.

FIG. 37 shows a configuration example of the sample processing chip 200 to be used in the emulsion PCR assay.

The sample processing chip 200 shown in FIG. 37 is configured as a combination of a plurality of types of fluid modules (220A to 220E) having different functions. Specifically, in the fluid module 220A, Pre-PCR processing is performed as the target-component processing. In the fluid module 220B, a droplet forming process is performed as the target-component processing. In the fluid module 220C, emulsion PCR is performed as the target-component processing. In the fluid module 220D, a droplet breaking process is performed as the target-component processing. In the fluid module 220E, a washing (primary washing) process is performed as the target-component processing. In the fluid module 220A, a hybridization process and a washing (secondary washing) process are performed as the target-component processing. DNA serving as the target component and liquid such as a reagent sequentially flow in each fluid module on the sample processing chip 200, whereby the emulsion PCR assay is performed. The fluid modules 220A to 220E may be integrated into a single fluid module 220 having formed therein the flow path 201 for performing each process.

(Pre-PCR)

Figure 38:
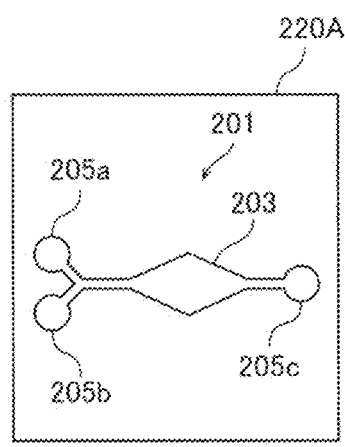
FIG. 38 is a diagram showing a configuration example of a fluid module to be used in Pre-PCR.

FIG. 38 shows a configuration example of the fluid module 220A to be used in the Pre-PCR. The flow path 201 of the fluid module 220A includes: a channel 203, connection portions 205a and 205b into each of which a reagent or a sample is injected; and a connection portion 205c from which liquid is discharged. For liquid flow velocity control, the channel 203 has a rhombic shape, for example.

The fluid module 220A is formed from a material having high heat-resistance such as polycarbonate, for example. The height of the channel 203 is set to be 50 μm to 500 μm, for example.

For example, DNA extracted through pretreatment is injected from the connection portion 205a, and the PCR amplification reagent is injected from the connection portion 205b. The temperature of the mixture of DNA and the reagent is controlled by the heater 460 while the mixture flows in the channel 203. Under the temperature control, DNA and the reagent react with each other, whereby DNA is amplified. The liquid containing the amplified DNA is transferred to the adjacent fluid module 220 via the connection portion 205c.

(Emulsion Formation)

Figure 39:
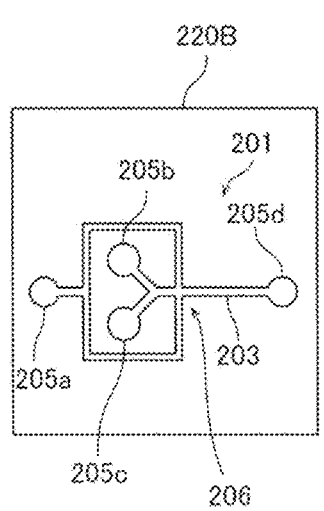
FIG. 39 is a diagram showing a configuration example of a fluid module to be used in emulsion formation.

FIG. 39 shows a configuration example of the fluid module 220B to be used in the emulsion formation. The flow path 201 of the fluid module 220B includes: a channel 203; connection portions 205a, 205b, and 205c into each of which a liquid such as the sample or a reagent is injected; and a connection portion 205d from which liquid is discharged. The channel 203 includes a crossing part 206 at which at least two channels cross each other. The width of each channel forming the crossing part 206 is several tens of micrometers. For example, the width of the channel is 20 μm. Only either the connection portion 205b or 205c may be provided to the fluid module 220B.

That is, in addition to the introducing of the first liquid 21, the dispersion medium 23 for emulsion formation is introduced into the flow path 201 in the sample processing chip 200, to perform emulsion formation.

The height of the channel 203 of the fluid module 220B is 10 μm to 20 μm, for example. In order to enhance wettability to oil, the wall surface of the channel 203 is treated with a hydrophobic material or fluorine, for example. The material of the fluid module 220B is PDMS, PMMA, or the like, for example.

For example, the liquid that contains DNA amplified in the Pre-PCR is injected from the connection portion 205b, and a liquid that contains magnetic particles and the PCR amplification reagent is injected from the connection portion 205c. The liquids respectively injected from the connection portions 205b and 205c are mixed with each other in the channel 203, to flow into the crossing part 206. The particle diameter of the magnetic particle is selected from a range of not less than 0.5 μm and not greater than 20 μm in terms of mean particle diameter, for example. The mean particle diameter denotes the number mean diameter measured by a light scattering method, for example. For sending liquids to the connection portions 205b and 205c, the flow rate of each of the liquids respectively injected from the connection portions 205b and 205c is controlled so as to be constant.

For example, in the emulsion formation, dispersoid droplets having a mean particle diameter of not less than 0.1 μm and not greater than 500 μm are formed from the first liquid 21. Since an emulsion including the first liquid 21 as dispersoid droplets can be formed while the flow of the first liquid 21 is accurately controlled, variation in the particle diameter of droplets can be suppressed. In addition, emulsion droplets having a substantially uniform particle diameter and having a mean particle diameter of not less than 0.1 μm and not greater than 500 μm can be efficiently formed. Preferably, in the emulsion formation, dispersoid droplets having a mean particle diameter of not less than 0.1 μm and not greater than 200 μm are formed from the first liquid 21. More preferably, in the emulsion formation, dispersoid droplets having a mean particle diameter of not less than 0.1 μm and not greater than 100 μm are formed from the first liquid 21. Accordingly, an emulsion suitable for bio-measurement can be formed.

For example, an oil for emulsion formation is injected from the connection portion 205a. The injected oil is divided into a plurality of passages in the channel 203, to flow into the crossing part 206 via the branched plurality of passages, for example. For sending the oil into connection portion 205a, the flow rate of the liquid injected from the connection portion 205a is controlled so as to be constant. In accordance with the flow rate of the liquid that forms the dispersoids, the flow rate of the oil serving as the dispersion medium 23 is controlled.

Figure 40:
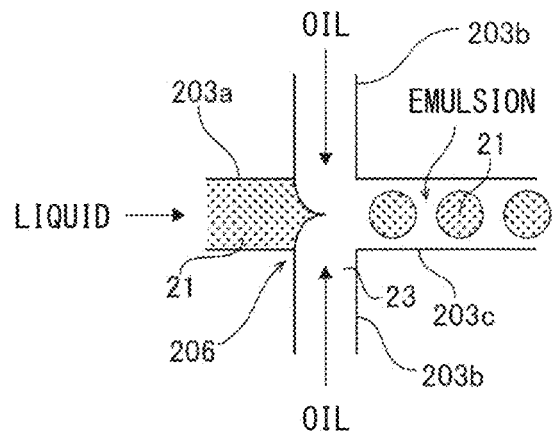
FIG. 40 is an enlarged view showing a first example of a crossing part in which an emulsion is formed.

FIG. 40 shows an example in which an emulsion is formed at the crossing part 206. For example, the first liquid 21 that contains the mixture of DNA and the reagent flows into the crossing part 206 into which the oil flows from the up-down directions in FIG. 40. The first liquid 21 is cut into droplets by the shear force that occurred by the first liquid 21 being nipped by the oil at the crossing part 206. The cut droplets are each covered by the oil that has flowed into the crossing part 206, whereby an emulsion is formed. The specimen flow in the form of an emulsion is transferred to the adjacent fluid module 220 via the connection portion 205d.

For example, the first liquid 21 forming the dispersoids flows into the crossing part 206 at a constant flow rate selected from a range of 0.4 μL/minute to 7 μL/minute, and the oil flows into the crossing part 206 at a constant flow rate selected from a range of 1 μL/minute to 50 μL/minute. The flow rate is controlled by the controller 10. For example, when the first liquid 21 is caused to flow into the crossing part 206 at a flow rate of 2 μL/minute (about 5200 mbar), and the oil is caused to flow into the crossing part 206 at a flow rate of 14 μL/minute (about 8200 mbar), droplets are formed at about 10 million droplets/minute.

For example, in the emulsion formation, dispersoid droplets of the first liquid 21 are formed at a rate of not less than 600 droplets/minute and not greater than 600 million droplets/minute. Since an emulsion including the first liquid 21 as dispersoid droplets can be formed while the flow of the first liquid 21 is accurately controlled, variation in the particle diameter of droplets can be suppressed. In addition, emulsion droplets having a substantially uniform particle diameter can be efficiently formed at a rate of not less than 600 droplets/minute and not greater than 600 million droplets/minute. Preferably, in the emulsion formation, dispersoid droplets of the first liquid 21 are formed at a rate of not less than 1000 droplets/minute and not greater than 600 million droplets/minute. More preferably, in the emulsion formation, dispersoid droplets of the first liquid 21 are formed at a rate of not less than 3000 droplets/minute and not greater than 18 million droplets/minute. Further preferably, in the emulsion formation, dispersoid droplets of the first liquid 21 are formed at a rate of not less than 5000 droplets/minute and not greater than 9 million droplets/minute.

Figure 41:
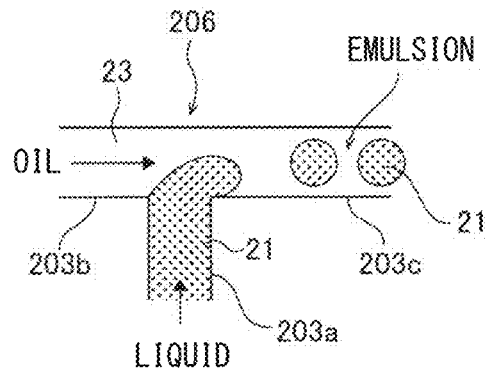
FIG. 41 is an enlarged view showing a second example of the crossing part in which an emulsion is formed.

In the example shown in FIG. 40, the crossing part 206 is formed in a shape of a cross composed of four channels 203 in total, i.e., one channel 203a into which the mixture flows, two channels 203b into which the oil flows, and one channel 203c from which the emulsion flows out. The crossing part 206 may be formed in a T-shape composed of three channels 203 as shown in FIG. 41.

(PCR)

Figure 42:
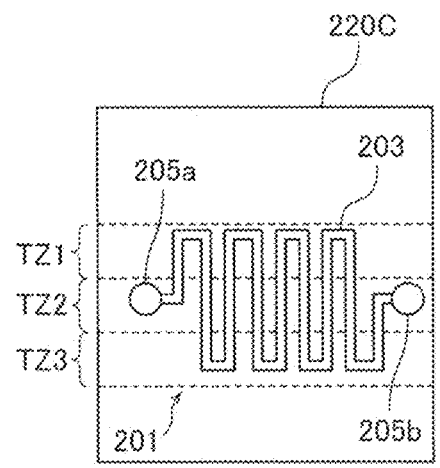
FIG. 42 is a diagram showing a configuration example of a fluid module to be used in emulsion PCR.

FIG. 42 shows a configuration example of the fluid module 220C to be used in the emulsion PCR. The flow path 201 of the fluid module 220C includes: a channel 203; a connection portion 205a into which a liquid flows; and a connection portion 205b from which liquid is discharged.

The fluid module 220C is formed from a material having high heat-resistance such as polycarbonate, for example. The height of the channel 203 is set to be 50 μm to 500 μm, for example.

The channel 203 has a structure in which the channel 203 passes, a plurality of times, a plurality of temperature zones TZ1 to TZ3 formed by the heater 460. The number of the temperature zones TZ may be a number other than three. The number of times by which the channel 203 passes the temperature zones TZ1 to TZ3 corresponds to the number of thermal cycles. Although depicted in a simplified manner in FIG. 42, the number of thermal cycles of the emulsion PCR is set to be about 40 cycles, for example. The channel 203 is formed in a shape in which the channel 203 reciprocates or meanders by the number of times that corresponds to the number of cycles. As shown in FIG. 42, DNA in each droplet is amplified while flowing in the channel 203.

(Emulsion Breaking)

Figure 43:
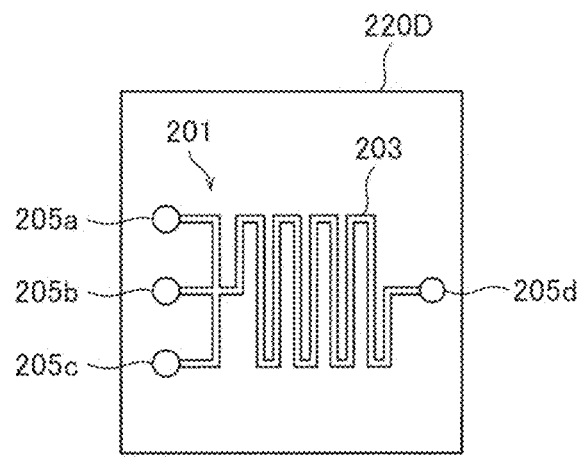
FIG. 43 is a diagram showing a configuration example of a fluid module to be used in emulsion breaking.

FIG. 43 shows a configuration example of the fluid module 220D to be used in the breaking of the emulsion. The flow path 201 of the fluid module 220D includes: a channel 203; connection portions 205a, 205b, and 205c into each of which the emulsion or an emulsion breaking reagent flows; and a connection portion 205d from which liquid is discharged.

The fluid module 220D is formed from a material having high chemical-resistance such as polycarbonate or polystyrene, for example. The height of the channel 203 is set to be 50 μm to 500 μm, for example.

For example, the emulsion having been subjected to the emulsion PCR step flows in from the connection portion 205b, and the emulsion breaking reagent flows in from the connection portions 205a and 205c. The emulsion and the emulsion breaking reagent are mixed to each other while flowing in the channel 203, and the droplets in the emulsion are broken. That is, in the target-component processing, droplets containing the carrier having bound thereto the amplification product of the nucleic acid, and a reagent for breaking the droplets are mixed to each other, whereby the droplets are broken. Accordingly, by the droplets and the reagent for breaking the droplets simply being mixed to each other, the droplets can be easily broken. The channel 203 is configured in a shape that allows mixing of the liquids to be promoted. For example, the channel 203 is formed such that liquid reciprocates a plurality of times in the width direction of the sample processing chip 200. The magnetic particles taken out of the droplets are transferred to the adjacent fluid module 220 via the connection portion 205d.

In the fluid module 220D, as a result of the droplet breaking process being performed as the target-component processing, particles and the magnetic particles serving as the carrier are dispersed in the process liquid in the channel 203. The magnetic particles are those having been taken out of the droplets through the breaking, and have bound thereto the nucleic acid which is the amplification product of the nucleic acid. The process liquid in the channel 203 is a mixture including the oil, the emulsion breaking reagent, the liquid having flowed out of the droplets as a result of the breaking (liquid encapsulated in the droplets together with DNA and PCR amplification reagent), and the like.

(Washing (Primary Washing))

Figure 44:
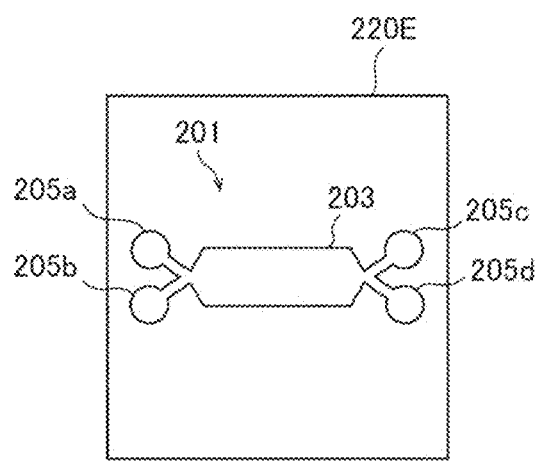
FIG. 44 is a diagram showing a configuration example of a fluid module to be used in a washing step (primary washing)

FIG. 44 shows a configuration example of the fluid module 220E to be used in the washing step (primary washing). The flow path 201 of the fluid module 220E includes: connection portions 205a and 205b into each of which a liquid flows, and connection portions 205c and 205d from each of which liquid is discharged; and a channel 203.

The channel 203 has a shape that linearly extends in a predetermined direction, such as a substantially rectangular shape, for example. The channel 203 has a wide shape that allows sufficient magnetic collection of magnetic particles or dispersion thereof to be performed. The connection portions 205a and 205b at the flow-in side are disposed at one end side of the channel 203, and the connection portions 205c and 205d at the discharge side are disposed at the other end side of the channel 203.

The fluid module 220E is formed from a material having high chemical-resistance such as polycarbonate or polystyrene, for example. The height of the channel 203 is set to be 50 μm to 500 μm, for example.

Figure 45:
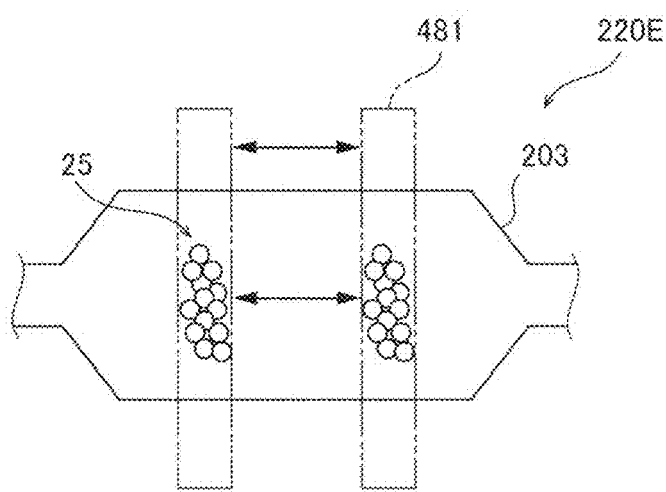
FIG. 45 is a diagram showing an operation example of washing/concentrating magnetic particles by use of a fluid module.

FIG. 45 shows an example of operation of washing/concentrating the magnetic particles in the fluid module 220E. The liquid containing the magnetic particles flows from the connection portion 205a toward the connection portion 205c. The magnetic particles in the liquid are concentrated by the magnetic force of the magnet 481. The magnet 481 can reciprocate in the longitudinal direction of the channel 203. The magnetic particles follow the reciprocating movement of the magnet 481, and are gathered while reciprocating in the channel 203.

The washing liquid is supplied from the connection portion 205b. The washing liquid continuously flows from the connection portion 205b toward the connection portion 205d. The connection portion 205d functions as a drain for discharging the washing liquid.

In the primary washing step, a washing liquid that contains alcohol is used. Through the primary washing using the washing liquid, the oil film on each magnetic particle is removed, and the amplified double-stranded DNA is denatured into single strands.

(Hybridization)

In the fluid module 220A having the same configuration as shown in FIG. 38, the magnetic particles are mixed with a reagent containing a labeled substance, and are subjected to thermal cycles. For example, the liquid containing the magnetic particles is transferred from the connection portion 205a, and the reagent containing the labeled substance is injected from the connection portion 205b. Through the thermal cycles, DNA on the magnetic particles and the labeled substance are bound to each other.

(Washing (Secondary Washing))

The secondary washing step after the hybridization (binding) with the labeled substance may be performed in the fluid module 220A. For example, in FIG. 38, in a state where the magnetic particles are collected in the channel 203 by the magnet 481 (see FIG. 45), a washing liquid is injected from the connection portion 205b. In the secondary washing step, PBS is used as the washing liquid. Through the secondary washing using the washing liquid, unreacted labeled substance that did not bind to DNA (including the labeled substance non-specifically attached to magnetic particles) is removed. The magnetic particles including the labeled substance after the secondary washing are discharged from the connection portion 205c. In this case, similarly to the fluid module 220E (see FIG. 44), the fluid module 220A is preferably provided with a connection portion 205 for draining at the discharge side.

At the downstream side of the fluid module 220A for performing hybridization, the fluid module 220E for performing the secondary washing may be added.

(Modification of Primary Washing, Hybridization, and Secondary Washing)

As another configuration example, a configuration may be employed in which the primary washing, the hybridization, and the secondary washing are performed in a single fluid module 220E (see FIG. 44). In this case, the specimen having been subjected to the emulsion breaking is introduced from the connection portion 205a into the channel 203, and the magnetic particles are collected by the magnet 481. Then, the alcohol-containing washing liquid for the primary washing, the labeled reagent for the hybridization, and the washing liquid (PBS) for the secondary washing are sequentially injected from the connection portion 205b, to perform the respective step processes. In this case, there is no need to provide the fluid module 220A at the downstream side of the fluid module 220E.

(Detection)

The magnetic particles including the labeled substance after the secondary washing are detected by means of a flow cytometer or image analysis, for example. For detection by a flow cytometer, the magnetic particles including the labeled substance are collected from the liquid sending apparatus 100, and then transferred to a separately-provided flow cytometer, for example. With respect to the magnetic particles including the labeled substance, fluorescence and the like based on the label are detected by the detector 470 of the liquid sending apparatus 100. Images of the magnetic particles including the labeled substance are taken by the camera unit of the liquid sending apparatus 100, and the taken images are analyzed by the liquid sending apparatus 100 or a computer connected to the liquid sending apparatus 100.

(Single Cell Analysis)

Figure 46:
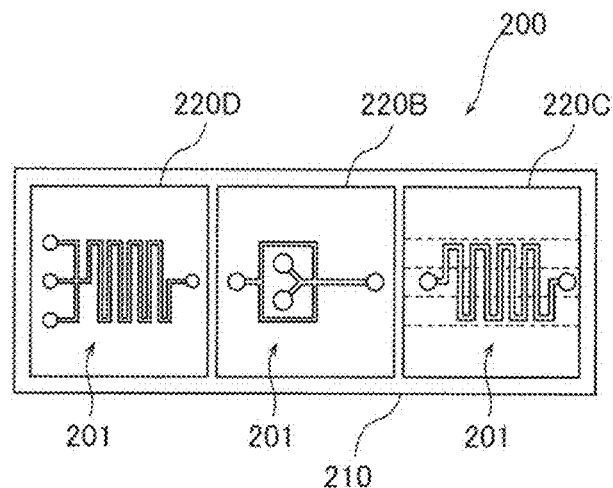
FIG. 46 is a diagram showing a configuration example of a sample processing chip to be used in single cell analysis.

An example of performing a single cell analysis by use of the sample processing chip 200 described above is provided. The single cell analysis is a technique of performing analysis per cell, with each individual cell in a specimen such as blood being set as an analysis target. FIG. 46 shows a configuration example of the sample processing chip 200 to be used in the single cell analysis.

The sample processing chip 200 is configured as a combination of a fluid module 220D for mixing liquids, a fluid module 220B for emulsion formation, and a fluid module 220C for PCR amplification, for example.

The single cell analysis includes: a step (first step) of mixing cells each serving as a target component with a reagent for causing amplification reaction of the nucleic acid in each cell; a step (second step) of forming, in a dispersion medium, droplets each containing a mixture of a cell lysis reagent and the liquid obtained through the mixing performed in the first step; and a step (third step) of amplifying in each droplet, the nucleic acid eluted from the cell in the droplet in the second step.

The configuration (material, channel height, etc.) of the fluid module 220D is the same as the configuration illustrated in FIG. 43, and detailed description thereof is omitted. A sample such as blood is injected from the connection portion 205b of the fluid module 220D, and a PCR amplification reagent is injected from the connection portions 205a and 205c. The cells contained in the sample and the PCR amplification reagent are mixed with each other while flowing in the channel 203.

The configuration (material, channel height, etc.) of the fluid module 220B is the same as the configuration illustrated in FIG. 39, and detailed description thereof is omitted. A mixture of the cells, the PCR amplification reagent, and a fluorescent dye is injected from the connection portion 205b of the fluid module 220B. A cell lysis reagent is injected from the connection portion 205c. An oil for emulsion formation is injected from the connection portion 205a. The mixture of the cells, the PCR amplification reagent, and the cell lysis reagent becomes droplets each covered by the oil in the crossing part 206, whereby an emulsion is formed. The droplets each encapsulating the mixture are transferred to the adjacent fluid module 220C via the connection portion 205d. The cell in each droplet is lysed by the cell lysis reagent while the emulsion is transferred to the fluid module 220C. From the lysed cell, DNA in the cell is eluted into the droplet containing the PCR amplification reagent.

The configuration of the fluid module 220C (material, channel height, etc.) is the same as the configuration illustrated in FIG. 42, and detailed description thereof is omitted. The emulsion having been transferred to the fluid module 220C is subjected to thermal cycles while flowing in the channel 203 of the fluid module 220C. Through the thermal cycles, DNA eluted from the cell in each droplet is amplified. Alternatively, protein eluted from the cell in the droplet may be detected through enzyme-substrate reaction or the like.

(Immunoassay (Digital ELISA))

Figure 47:
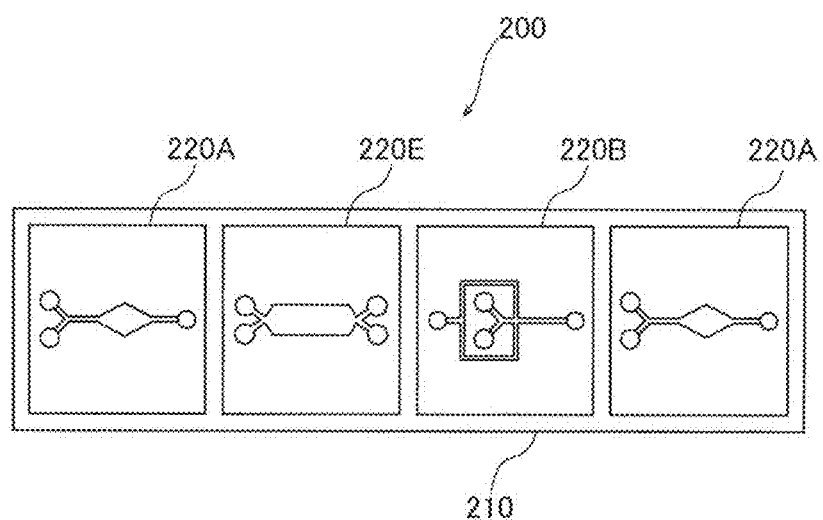
FIG. 47 is a diagram showing a configuration example of a sample processing chip to be used in immunoassay.

An example of performing immunoassay by use of the sample processing chip 200 described above is provided. In immunoassay, protein such as antigen or antibody contained in blood or the like is set as a target component. FIG. 47 shows a configuration example of the sample processing chip 200 to be used in Digital ELISA (Enzyme-Linked ImmunoSorbent Assay).

The sample processing chip 200 is configured as a combination of a fluid module 220A for temperature control, a fluid module 220E for BF separation, a fluid module 220B for emulsion formation, and a fluid module 220A for temperature control.

FIG. 48 shows the outline of Digital ELISA. ELISA is a technique in which: an antigen (or an antibody) serving as a target component, and a labeled substance are caused to be carried by a magnetic particle to form an immune complex; and the target component is detected on the basis of the label in the immune complex. Digital ELISA is a technique of performing absolute quantification of the target component concentration in a sample, by dispersing the sample diluted to a limiting dilution (a dilution that causes 1 or 0 target component to be contained in each micro partition) into micro partitions, and then by directly counting the number of micro partitions having positive signals based on the label. In the case of FIG. 48, each of individual droplets in the emulsion is a micro partition. By use of the sample processing chip 200, the assay shown in the example in FIG. 48 is performed.

More specifically, the Digital ELISA assay includes: a step (first step) of forming an immune complex in which a target component (antigen or antibody) and a carrier are bound to each other through antigen-antibody reaction; a step (second step) of causing the immune complex formed through the first step and a labeled substance to react with each other; a step (third step) of forming, in a dispersion medium, droplets each containing the immune complex having the labeled substance bound thereto through the second step and a substrate for detecting the labeled substance; and a step (fourth step) of causing the substrate to react with the labeled substance in each droplet formed through the third step.

The configuration (material, channel height, etc.) of the fluid module 220A is the same as the configuration illustrated in FIG. 38, and detailed description thereof is omitted. A sample containing an antigen is injected from the connection portion 205a of the fluid module 220A, and a reagent containing a primary antibody and magnetic particles is injected from the connection portion 205b. The sample and the reagent are mixed with each other in the channel 203. The mixture is subjected to temperature control in the channel 203, whereby an immune complex containing the antigen, the primary antibody, and the magnetic particle is generated. The temperature is controlled to be about 40° C. to about 50° C., more preferably, about 42° C. The liquid containing the generated complex is transferred to the adjacent fluid module 220E through the connection portion 205c.

The configuration (material, channel height, etc.) of the fluid module 220E is the same as the configuration illustrated in FIG. 44, and detailed description thereof is omitted. In the channel 203 of the fluid module 220E, the complex containing the magnetic particle is collected by the magnet 481 and washed (primary BF separation). After the primary BF separation, influence of the magnetic force by the magnet 481 is eliminated and the immune complex is dispersed. The dispersed immune complex is caused to react with an enzyme-labeled antibody. After the reaction, the immune complex is collected by the magnet 481 and washed again (secondary BF separation). After the washing, the immune complex is transferred to the adjacent fluid module 220B.

The configuration (material, channel height, etc.) of the fluid module 220B is the same as the configuration illustrated in FIG. 39, and detailed description thereof is omitted. The complex is injected from the connection portion 205b of the fluid module 220B, and a reagent that contains a fluorescent/luminescent substrate is injected from the connection portion 205c. An oil for emulsion formation is injected from the connection portion 205a. In the crossing part 206, the liquid containing the immune complex, and the reagent containing the fluorescent/luminescent substrate are made into droplets while being covered with the oil, to form an emulsion. The emulsion is transferred from the connection portion 205d to the adjacent fluid module 220A.

The emulsion transferred to the fluid module 220A is heated in the channel 203, and the substrate and the immune complex react with each other in each individual droplet, whereby fluorescence is generated. The detector 470 of the liquid sending apparatus 100 detects the fluorescence. As a result, detection per one molecule of the target component encapsulated in each individual droplet is enabled.

In the fluid module 220A, the magnetic particles, which are particles, are each bound to the antigen or antibody serving as the target component, and are dispersed in the mixture of the sample and the reagent serving as the process liquid. In the fluid module 220E, the magnetic particles, which are particles, are dispersed in a washing liquid serving as the process liquid. In the fluid module 220B, the droplets, which are particles, are dispersed in the oil serving as the process liquid. In the fluid module 220A, the droplets, which are particles, are dispersed in the oil serving as the process liquid.

(Combination of First Liquid and Second Liquid)

With reference to FIG. 49, one example of the correspondence relationship between the steps, and the first liquid 21 and the second liquid 22 is described.

As shown in FIG. 49, in the step of Pre-PCR, a mixture that contains a DNA sample and a PCR amplification reagent is used as the first liquid 21. In this case, the first liquid 21 is sent into the flow path 201 in the sample processing chip 200 at a flow rate of 2 µL/minute, for example. In addition, in the step of Pre-PCR, a mixture that contains a mineral oil is used as the second liquid 22. In the step of Pre-PCR, the first liquid 21 serves as an aqueous phase and the second liquid 22 serves as an oil phase.

In the steps of emulsion formation and emulsion PCR, a mixture that contains the DNA amplified through the step of Pre-PCR, the magnetic particles, and the PCR amplification reagent is used as the first liquid 21. In this case, the first liquid 21 is sent into the flow path 201 in the sample processing chip 200 at a flow rate of 2 µL/minute, for example. In the steps of emulsion formation and emulsion PCR, a mixture that contains a mineral oil is used as the second liquid 22. In the steps of emulsion formation and emulsion PCR, the first liquid 21 serves as an aqueous phase and the second liquid 22 serves as an oil phase.

In the steps of emulsion breaking and hybridization, a mixture of droplets each containing the DNA sample amplified through the step of emulsion PCR is used as the first liquid 21. The first liquid 21 in this case is sent into the flow path 201 in the sample processing chip 200 at a flow rate of 2 µL/minute, for example. In the steps of emulsion breaking and hybridization, a reagent which contains a labeled probe is used as the first liquid 21. The first liquid 21 in this case is sent into the flow path 201 in the sample processing chip 200 at a flow rate of 20 µL/minute, for example. In the steps of emulsion breaking and hybridization, a mixture that contains a mineral oil is used as the second liquid 22.

Description of Example

Next, Examples performed in order to confirm the effects of the liquid sending method of the present embodiment are described. In the present embodiment, experiments were performed in which the first liquid 21 as dispersoids was introduced together with the dispersion medium 23 into the flow path 201 in the sample processing chip 200, to form an emulsion.

The configuration used in Examples is shown in FIG. 50. In Examples 1 and 2, a mixture that contained DNA amplified through Pre-PCR, magnetic particles, and a PCR amplification reagent was supplied as the first liquid 21 to the channel 203a. The first liquid 21 was supplied to the channel 203a by being pushed out by a mixture containing a mineral oil serving as the second liquid 22. In Examples 1 and 2, as shown in FIG. 51 and FIG. 52, a mixture containing a mineral oil was supplied to the channel 203b, as a continuous phase for forming an emulsion. The channel 203a and the channel 203b were configured to cross each other at the crossing part 206. The cross-sectional area of the crossing part 206 was 400 µm² (20 µm×20 µm). The formed emulsion was caused to pass through the channel 203c. The formed emulsion was observed by use of KEYENCE BZ-X700 Fluorescence Microscope.

In Example 1, the first liquid 21 was supplied from the first container 14a serving as a sample container. That is, the second liquid 22 of which flow rate was controlled was caused to flow into the first container 14a containing the first liquid 21, whereby the flow rate of the first liquid 21 was controlled. In Example 1, the flow rate of the second liquid 22 was controlled to be 3.25 µL/minute such that the flow rate of the first liquid 21 became 3.25 µL/minute. The flow rate of the continuous phase was controlled so as to be 6.5 µL/minute. The control of the flow rate of the continuous phase was performed by feedback-control by use of a sensor 12a, similarly to the control of the flow rate of the second liquid 22. That is, the continuous phase was contained in a container 13a, and pressure was applied to the container 13a by a liquid sending portion 11a, whereby the continuous phase was sent. Then, the flow rate of the continuous phase was measured by the sensor 12a, whereby the liquid sending portion 11a was feedback-controlled.

In Example 2, the first liquid 21 was supplied from the reservoir 14b on the sample processing chip 200. That is, the second liquid 22 of which flow rate was controlled was caused to flow into the reservoir 14b containing the first liquid 21, whereby the flow rate of the first liquid 21 was controlled. In Example 2, the flow rate of the second liquid 22 was controlled to be 3.6 μL/minute such that the flow rate of the first liquid 21 became 3.6 μL/minute. The flow rate of the continuous phase was controlled so as to be 3.9 μL/minute. The control of the flow rate of the continuous phase was performed by feedback-control by use of the sensor 12a, similarly to the control of the flow rate of the second liquid 22.

Figure 53A:
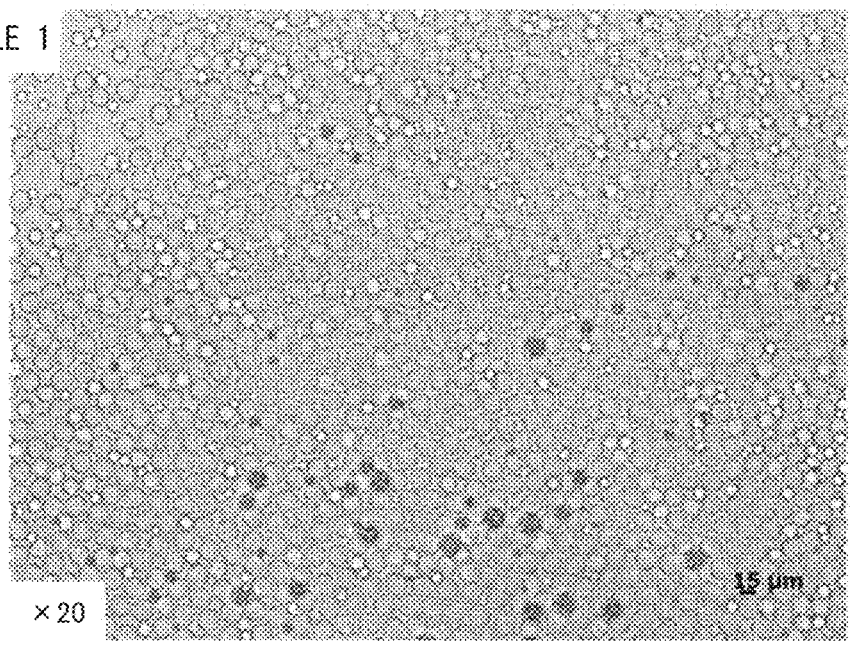
FIG. 53A is a diagram for describing the result of the experiment of Example 1.
Figure 53B:
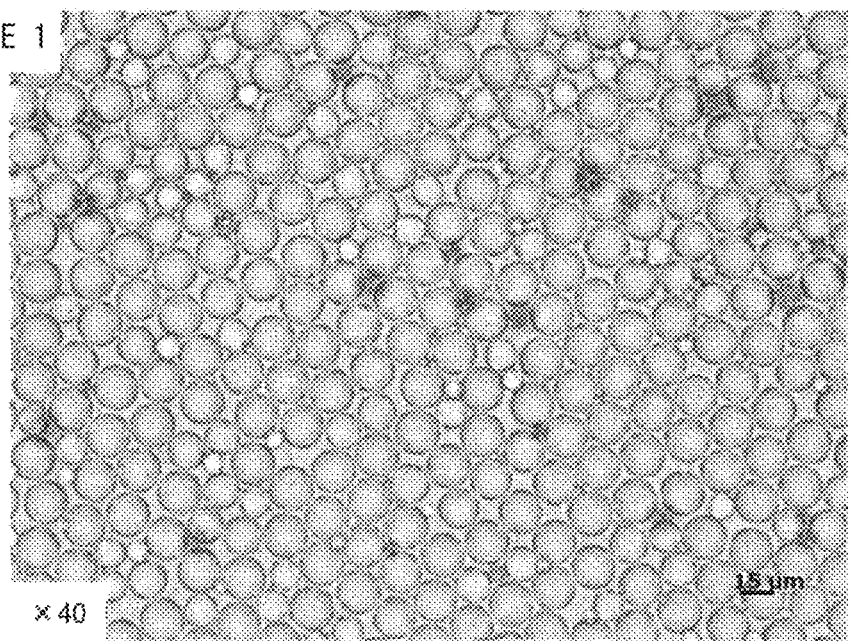
FIG. 53B is a diagram for describing the result of the experiment of Example 1.

In Example 1, as shown in FIGS. 53A and 53B, an emulsion that had dispersoids having a particle diameter of about 15 μm was able to be formed. In Example 1, the emulsion was able to be formed, without variation of the particle diameter of the dispersoids. That is, by the flow rate of the first liquid 21 being accurately controlled, an emulsion that had dispersoids having a substantially uniform particle diameter was able to be formed.

Figure 54A:
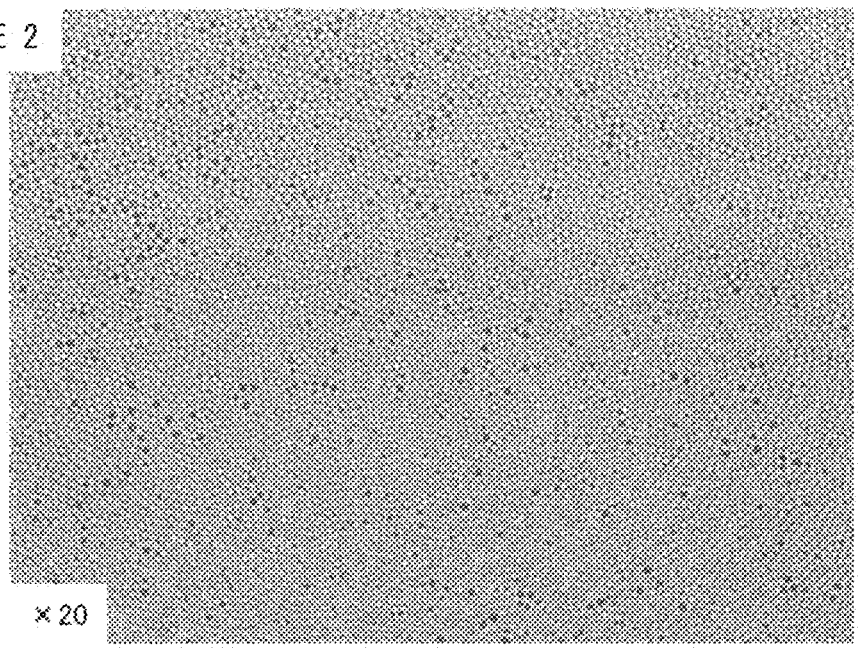
FIG. 54A is a diagram for describing the result of the experiment of Example 2.
Figure 54B:
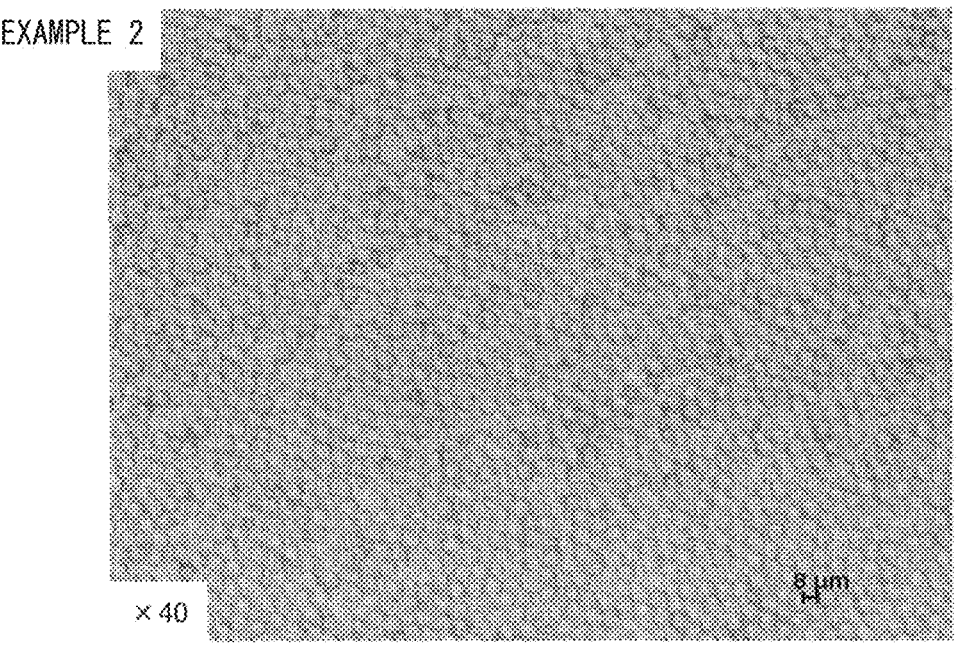
FIG. 54B is a diagram for describing the result of the experiment of Example 2.

In Example 2, as shown in FIGS. 54A and 54B, an emulsion that had dispersoids having a particle diameter of about 8 μm was able to be formed. In Example 2, the emulsion was able to be formed, without variation of the particle diameter of the dispersoids. That is, by the flow rate of the first liquid 21 being accurately controlled, an emulsion that had dispersoids having a substantially uniform particle diameter was able to be formed.

Comparative Example

In Comparative Examples, experiments were performed in which the first liquid as dispersoids was introduced together with the dispersion medium into the flow path 201 in the sample processing chip 200, to form an emulsion.

The configuration used in Comparative Examples is shown in FIG. 55. In Comparative Examples 1 and 2, a mixture that contained DNA amplified through Pre-PCR, magnetic particles, and a PCR amplification reagent was supplied as the first liquid to a channel 505a. The first liquid was supplied to the channel 505a by being pushed out by air supplied by the pump 502. In Comparative Examples 1 and 2, as shown in FIG. 56 and FIG. 57, a mixture containing a mineral oil was supplied to a channel 505b, as a continuous phase for forming an emulsion. The channel 505a and the channel 505b were configured to cross each other at a crossing part 507. The cross-sectional area of the crossing part 507 was 400 μm² (20 μm×20 μm). The formed emulsion was caused to pass through a channel 505c. The formed emulsion was observed by use of KEYENCE BZ-X700 Fluorescence Microscope.

In Comparative Examples 1 and 2, the first liquid was supplied from a sample container 504. That is, air of which pressure was controlled was caused to flow into the sample container 504 containing the first liquid, whereby the flow rate of the first liquid was controlled. That is, the pressure of the air flowing into the sample container 504 was controlled through feedback-control by use of the sensor 503. Similarly to the control of the flow rate of the first liquid, the control of the flow rate of the continuous phase was performed, by use of a sensor 503a, by feedback-controlling the pressure of the air which pushes out the continuous phase. That is, the continuous phase was contained in a container 504a, and pressure was applied to the container 504a by a pump 502a, whereby the continuous phase was sent. Then, the pressure of the air for pushing out the continuous phase was measured by the sensor 503a, whereby the pump 502a was feedback-controlled.

In Comparative Example 1, the pressure for the first liquid was controlled so as to be 1500 mbar. In addition, the pressure of the fluid of the continuous phase was controlled so as to be 1500 mbar. However, since the flow rate of the liquid could not be controlled, the flow rate of the first liquid was unstable. In addition, the flow rate of the continuous phase was unstable.

In Comparative Example 2, the pressure for the first liquid was controlled so as to be 1000 mbar. The pressure of the fluid of the continuous phase was controlled so as to be 1500 mbar. However, since the flow rate of the liquid could not be controlled, the flow rate of the first liquid was unstable. In addition, the flow rate of the continuous phase was unstable.

Figure 58:
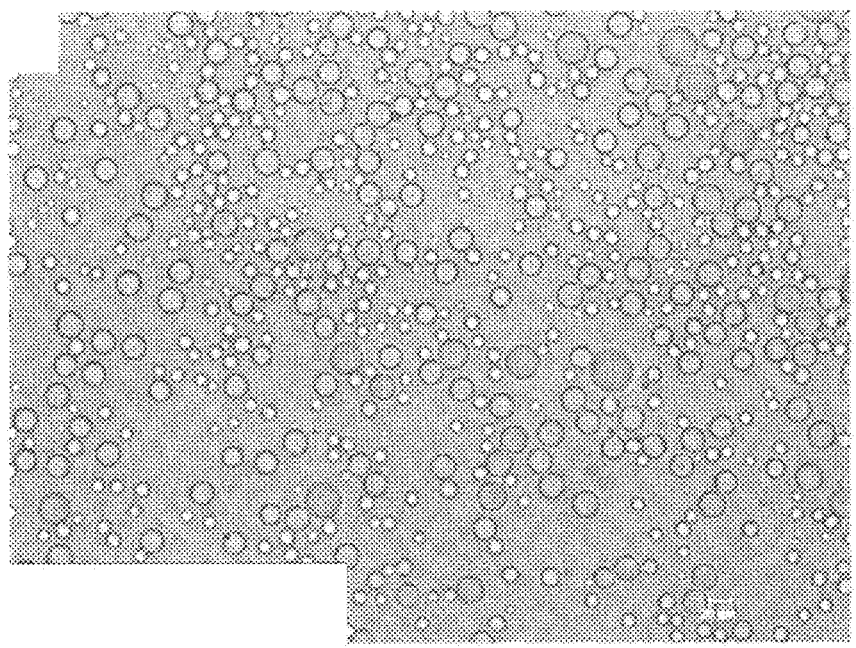
FIG. 58 is a diagram for describing the result of the experiment of Comparative Example 1.
Figure 59:
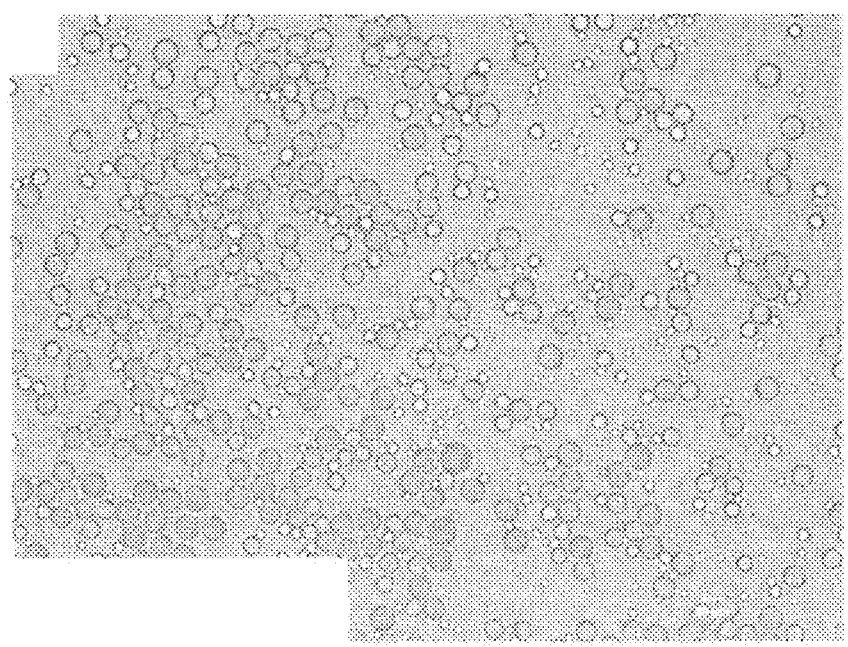
FIG. 59 is a diagram for describing the result of the experiment of Comparative Example 2.
Figure 60:
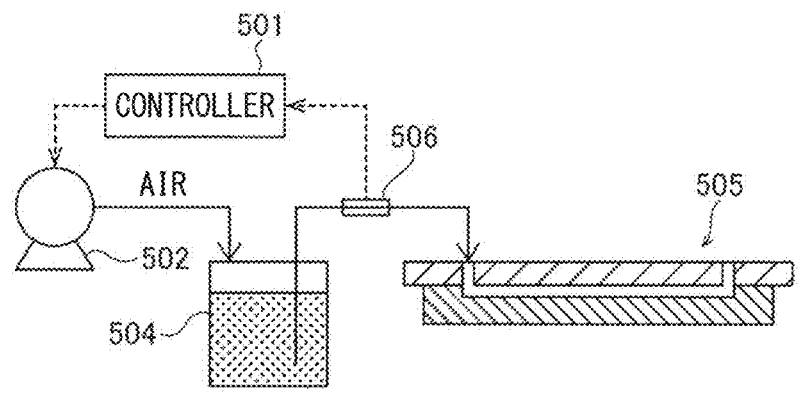
FIG. 60 is a diagram for describing a liquid sending method according to conventional art.
Figure 61:
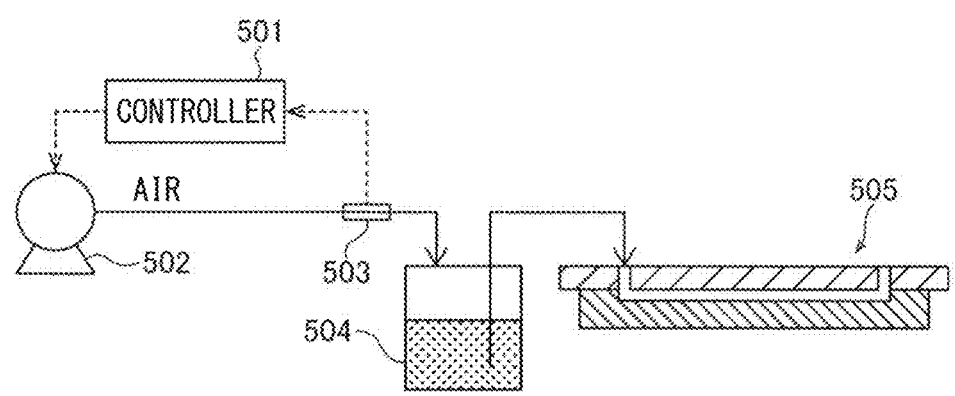
FIG. 61 is a diagram for describing another liquid sending method according to conventional art.

In Comparative Examples 1 and 2, with respect to the continuous phase and the first liquid, the fluid of which flow rate was measured was gas, which allows a change in volume due to a slight change in pressure, and thus, the flow velocity of the first liquid and the continuous phase to be introduced was not able to be accurately controlled. In Comparative Examples 1 and 2, since the flow rate of the liquids to be introduced was not able to be controlled, there was a case where no emulsion was formed. As shown in FIG. 58 and FIG. 59, even when an emulsion was formed, the particle diameters of the dispersoids were not uniform. A result was obtained indicating that: when an emulsion is formed according to Comparative Examples 1 and 2, the uniformity of the size of the formed dispersoid droplets is poor; and the dependence on the pressure values is small.

It should be noted that the embodiment disclosed herein is merely illustrative in all aspects and should not be considered as being restrictive. The scope of the present invention is defined by the scope of the claims rather than by the description of the above-described embodiment, and includes meaning equivalent to the scope of the claims and all changes (modifications) within the scope.

What is claimed is:

1. A liquid sending method for sending liquid to a sample processing chip having a flow path therein, the method comprising:
   introducing a first liquid accommodated in a first container into the flow path in the sample processing chip by supplying, to the first container, a second liquid accommodated in a second container that is fluidically connected to the first container, wherein the second liquid is supplied to the first container by air sent under pressure to the second container, and the first liquid is different from the second liquid;
   measuring a flow rate of the second liquid while the second liquid flows;
   controlling the flow rate of the second liquid based on a measurement of the flow rate of the second liquid;
   introducing a dispersion medium for emulsion formation into the flow path in the sample processing chip to perform the emulsion formation; and
   forming droplets containing the first liquid at a rate of not less than 600 droplets/minute and not greater than 600 million droplets/minute.

2. The liquid sending method of claim 1, wherein
   a flow of the first liquid which is introduced into the flow path in the sample processing chip is controlled by the controlling of the flow of the second liquid.

3. The liquid sending method of claim 1, wherein
   the measuring of the flow is measuring at least one of flow rate, flow velocity, and pressure.

4. The liquid sending method of claim 1, wherein
the second liquid is a liquid having immiscibility with the first liquid.

5. The liquid sending method of claim 4, wherein
the first liquid is at least one of a first aqueous phase or a first oil phase, and
the second liquid is at least one of a second aqueous phase or a second oil phase.

6. The liquid sending method of claim 4, wherein
the second liquid is a liquid having a specific gravity different from that of the first liquid.

7. The liquid sending method of claim 1, wherein
the first liquid is a solution that contains a nucleic acid derived from blood, magnetic particles, and a reagent for polymerase chain reaction.

8. The liquid sending method of claim 1, wherein
the second liquid is a liquid that contains an oil being in a liquid state at room temperature.

9. The liquid sending method of claim 1, wherein
the first liquid is introduced into the flow path in the sample processing chip at a flow rate of not less than 0.1 μL/minute and not greater than 5 mL/minute.

10. The liquid sending method of claim 1, wherein
the droplets have a mean particle diameter of not less than 0.1 μm and not greater than 500 μm.

11. The liquid sending method of claim 1, wherein
the flow path formed in the sample processing chip has a cross-sectional area of not less than 0.01 μm$^2$ and not greater than 10 mm$^2$.

12. The liquid sending method of claim 1, wherein
the flow path formed in the sample processing chip has a height of not less than 1 μm and not greater than 500 μm, and a width of not less than 1 μm and not greater than 500 μm.

13. The liquid sending method of claim 1, wherein
a plurality of types of liquids including the first liquid are introduced into the flow path in the sample processing chip.

* * * * *